US011179477B2

(12) United States Patent
Kirn et al.

(10) Patent No.: US 11,179,477 B2
(45) Date of Patent: Nov. 23, 2021

(54) METHOD OF USING ADENO-ASSOCIATED VIRUS WITH VARIANT CAPSID

(71) Applicant: 4D MOLECULAR THERAPEUTICS INC., Emeryville, CA (US)

(72) Inventors: David H. Kirn, Emeryville, CA (US); Melissa Kotterman, Emeryville, CA (US); David Schaffer, Emeryville, CA (US)

(73) Assignee: 4D MOLECULAR THERAPEUTICS INC., Emeryville, CA (US)

( * ) Notice: Subject to any disclaimer, the term of this patent is extended or adjusted under 35 U.S.C. 154(b) by 0 days.

(21) Appl. No.: 16/952,002

(22) Filed: Nov. 18, 2020

(65) Prior Publication Data

US 2021/0069349 A1 Mar. 11, 2021

Related U.S. Application Data

(62) Division of application No. 16/300,446, filed as application No. PCT/US2017/032542 on May 12, 2017.

(60) Provisional application No. 62/454,612, filed on Feb. 3, 2017, provisional application No. 62/384,590, filed on Sep. 7, 2016, provisional application No. 62/378,106, filed on Aug. 22, 2016, provisional application No. 62/336,441, filed on May 13, 2016.

(51) Int. Cl.
| | |
|---|---|
| *A61K 48/00* | (2006.01) |
| *A61P 27/02* | (2006.01) |
| *C12N 15/86* | (2006.01) |
| *A61K 9/00* | (2006.01) |
| *C07K 14/005* | (2006.01) |

(52) U.S. Cl.
CPC ........ *A61K 48/0016* (2013.01); *A61K 9/0019* (2013.01); *A61K 9/0048* (2013.01); *A61K 48/0025* (2013.01); *A61K 48/0058* (2013.01); *A61K 48/0075* (2013.01); *A61P 27/02* (2018.01); *C07K 14/005* (2013.01); *C12N 15/86* (2013.01); *C07K 2319/00* (2013.01); *C12N 2750/14122* (2013.01); *C12N 2750/14143* (2013.01)

(58) Field of Classification Search
CPC .. C07K 14/005; C07K 2319/00; C12N 15/86; C12N 2750/14143; C12N 2750/14122; A61K 48/0016; A61K 48/0058
See application file for complete search history.

(56) References Cited

U.S. PATENT DOCUMENTS

| | | | |
|---|---|---|---|
| 2003/0078411 A1 | 4/2003 | Patel et al. | |
| 2006/0127358 A1* | 6/2006 | Muzyczka | C12N 15/86 424/93.2 |
| 2014/0294771 A1 | 10/2014 | Schaffer et al. | |
| 2015/0232953 A1* | 8/2015 | Schaffer | A61K 48/0075 506/2 |

FOREIGN PATENT DOCUMENTS

| | | | | |
|---|---|---|---|---|
| AU | 2017261812 B2 | 11/2017 | | |
| CA | 2941640 A1 | 9/2015 | | |
| CA | 3029833 A1 | 2/2018 | | |
| JP | 2005-512569 A | 5/2005 | | |
| JP | 2014-518614 A | 8/2014 | | |
| RU | 2301260 C2 | 6/2007 | | |
| WO | 2009/012176 A2 | 1/2009 | | |
| WO | 2010/093784 A2 | 8/2010 | | |
| WO | 2012/145601 A2 | 10/2012 | | |
| WO | 2014/103957 A2 | 7/2014 | | |
| WO | 2015/134643 A1 | 9/2015 | | |
| WO | 2015/164757 A1 | 10/2015 | | |
| WO | 2017/218842 A1 | 6/2017 | | |
| WO | WO-2017218842 A1 * | 12/2017 | ........... | C07K 14/015 |
| WO | 2018/022905 A2 | 2/2018 | | |
| WO | WO-2018022905 A2 * | 2/2018 | .............. | A61P 27/02 |

OTHER PUBLICATIONS

Choi et al Curr Gene Ther. June ; 5(3): 299-310 (Year: 2005).*
Michelfelder et al PLoS ONE ;4:e 5122,pp. 1-13 (Year: 2009).*
Varadi et al (Gene Ther. 19(8):800-9 (Year: 2012).*
Vandenberghe et al Cold Spring Harbor Perspect Med, 5, 1017442, 1-9 (Year: 2015).*
Moore et al Expert. Opinion Biol. Therp, 1235-1244 (Year: 2017).*
MacDonald et al TVST, 9(3), 1-9 (Year: 2020).*
Fisher et al Molecular Therapy, 25, 1854-1865 (Year: 2017).*
Deng et al Human Gene Therapy. 26(9):593-602 (Year: 2015).*
Martinez-Fernandez et al Expert Opin Orphan Drugs. ; 6(3): 167-177 (Year: 2018).*

(Continued)

*Primary Examiner* — Anoop K Singh
(74) *Attorney, Agent, or Firm* — Much Shelist, PC; Christopher M. Cabral

(57) ABSTRACT

Provided herein are variant adeno-associated virus (AAV) capsid proteins having one or more modifications in amino acid sequence relative to a parental AAV capsid protein, which, when present in an AAV virion, confer increased infectivity of one or more types of retinal cells as compared to the infectivity of the retinal cells by an AAV virion comprising the unmodified parental AAV capsid protein. Also provided are recombinant AAV virions and pharmaceutical compositions thereof comprising a variant AAV capsid protein as described herein, methods of making these rAAV capsid proteins and virions, and methods for using these rAAV capsid proteins and virions in research and in clinical practice, for example in, e.g., the delivery of nucleic acid sequences to one or more cells of the retina for the treatment of retinal disorders and diseases.

6 Claims, 38 Drawing Sheets

Specification includes a Sequence Listing.

(56) References Cited

OTHER PUBLICATIONS

Asur, P., et al., "Directed Evolution of Adeno-Associated Virus for Enhanced Gene Delivery and Gene Targeting in Human Pluripotent Stem Cells," Molecular Therapy, vol. 20, No. 2, pp. 329-338, (Nov. 22, 2011).
Jang, J. H., et al., An Evolved Adeno-Associated Viral Variant Enhances Gene Delivery and Gene Targeting in Neural Stem Cells, Molecular Therapeutics, vol. 19, No. 4, pp. 667-675 (Jan. 11, 2011).
Mondego, J. M., et al., "A Genome Survey of Moniliophthora Pemiciosa Gives New Insights into Witches' Broom Disease of Cacao," BMC Genomics, vol. 18, No. 9, pp. 1-25 (Nov. 18, 2008).
Xiao, W., et al., "Gene Therapy Vectors Based on Adeno-Associated Virus Type 1." Journal of Virology, vol. 73, No. 5, pp. 3994-4003 (May 1999).
International Search Report of PCT/US2017/32542 dated Oct. 24, 2017.
Written Opinion of PCT/US2017/32542 dated Oct. 24, 2017.
Australian Patent Application No. 2017261812—allowed claims.
Australian Patent Application No. 2017261812—First Examination Report dated Feb. 13, 2019.
Australian Patent Application No. 2017261812—Response to first Examination Report filed Mar. 14, 2019.
Australian Patent Application No. 2017261812—Notice of Acceptance dated Apr. 9, 2019.
Japanese Patent Application No. 2018-564723—Allowed claims.
Japanese Patent Application No. 2018-564723—Notice of Reasons for Rejection dated Apr. 15, 2019.
Japanese Patent Application No. 2018-564723—Response to official action filed Jul. 1, 2018.
Japanese Patent Application No. 2018-564723—Notice of Allowance dated Jun. 10, 2019.
Muller, O., et al., "Random peptide libraries displayed on adeno-associated virus to select for targeted gene therapy vectors," Nature Biotechnology, vol. 21, No. 9, pp. 1040-1046 (Sep. 2003).
Naumer, M., et al., "Development and Validation of Novel AAV2 Random Libraries Displaying Peptides of Diverse Lengths and at Diverse Capsid Positions," Human Gene Therapy, vol. 23, pp. 492-507 (May 2012).
Waterkamp, D. A., et al., "Isolation of Targeted AAV2 Vectorws from Novel Virus Display Libraries," J. Gene Med, vol. 8, pp. 1307-1319 (Sep. 6, 2006 published online).
Petrs-Silva, H., et al., "High-efficiency Transduction of the Mouse Retina by Tyrosine-Mutant AAV Serotype Vectors," Mol. Therapy, vol. 17, No. 3, pp. 463-571 (Mar. 2009).
Park, T.K., et al., "Intravitreal Delivery of AAV8 Retinoschisin Results in Cell Type-Specific Gene Expression and Retinal Rescue in the Rs1—KO Mouse," Gene Therapy, vol. 16, No. 7, pp. 916-926 (Jul. 2009).
Search Report of Brazil Patent Application No. BR112018072849-7 dated Jun. 20, 2020.
Technical Examination Report (Notice of Allowance) of Brazil Patent Application No. BR 110218072849-7 dated Oct. 6, 2020.
Allowed Claims of Brazil Patent Application No. BR 110218072849-7.
Official action of Canadian Patent Application No. 3,023,592 dated Jul. 29, 2019.
Official action of Canadian Patent Application No. 3,023,592 dated Dec. 16, 2019.
Official action of Canadian Patent Application No. 3,023,592 dated May 21, 2020.
Official action of Canadian Patent Application No. 3,023,592 dated Jul. 9, 2020.
Notice of Allowance of Canadian Patent Application No. 3,023,592 dated Jul. 29, 2020.
Allowed claims of Canadian Patent Application No. 3,023,592.
Official action of New Zealand Patent Application No. 748395 dated Sep. 27, 2019.
Notice of Acceptance of New Zealand Patent Application No. 748395 dated Dec. 9, 2019.
Allowed claims of New Zealand Patent Application No. 748395.
Search report of Russian Patent Application No. 2018142768 dated Nov. 19, 2019.
Official action of Russian Patent Application No. 2018142768 dated Nov. 19, 2019.
Official action of Russian Patent Application No. 2018142768 dated Mar. 17, 2020.
Decision to Grant of Russian Patent Application No. 2018142768 dated Apr. 20, 2020.
Allowed claims of Russian Patent Application No. 2018142768.
Beltran, W. A., et al., "Gene Therapy Rescues Photoreceptor Blindness in Dogs and Paves the Way for Treating Human X-linked Retinitis Pigmentosa," PNAS, vol. 109, No. 6, pp. 2132-2137 (Feb. 7, 2012).
Boye, S., et al., "The Human Rhodopsin Kinase Promoter in an AAV5 Vector Confers Rod-and Cone-Specific Expression in the Primate Retina," Human Gene Therapy, vol. 23, pp. 1101-1115 (Oct. 2012).
Choi, V., et al., "AAV Hybrid Serotypes: Improved Vectors for Gene Delivery," Curr Gene Ther., vol. 5, No. 3, pp. 299-310 (Jun. 2005).
Deng, Wen-Tao, et al., "Stability and Safety of an AAV Vector for Treating RPGR-ORF15 X-Linked Retinitis Pigmentosa," Human Gene Therapy, vol. 26, No. 9, pp. 593-602 (Jun. 15, 2015 published online).
Garoon, R., et al., "Update on Ocular Gene Therapy and Advances in Treatment of Inherited Retinal Diseases and Exudative Macular Degeneration," Current Opinion, vol. 27, No. 3, pp. 268-273 (May 2016).
Gorbatyuk, M., et al., "Suppression of Mouse Rhodopsin Expression in Vivo by AAV Mediated siRNA Delivery," Vision Res, vol. 49, No. 9, pp. 1202-1208 (Apr. 2007).
Jacobson, S., et al., "Gene Therapy for Leber Congenital Amaurosis Caused by RPE65 Mutations," Arch Ophthalmol, vol. 130, No. 1 pp. 1-16 (Jan. 2012).
MacLaren, R. E., et al., "Retinal Gene Therapy in Patients with Choroideremia: Initial Findings from a Phase ½ Clinical Trial," The Lancet, vol. 383, Issue 9923, pp. 1129-1137 (Mar. 29, 2014).
Michelfelder, S., et al., "Successful Expansion but Not Complete Restriction of Tropism of Adeno-Associated Virus by In Vivo Biopanning of Random Virus Display Peptide Libraries," PLoS One, vol. 4, Issue 4, e5122 (Apr. 9, 2009).
Moore, N., et al., "Gene Therapy for Age-Related Macular Degeneration," Expert Opinion on Biological Therapy, vol. 17, No. 10, pp. 1235-1244 (Jul. 20, 2017).
D'Donnell, J., et al., "Adeno-Associated Virus-2 and its Primary Cellular Receptor—Cryo-EM Structure of a Heparin Complex," Virology, vol. 385, No. 2, pp. 434-443 (Mar. 15, 2009).
Peden, M., et al., "Ab-Externo AAV-Mediated Gene Delivery to the Suprachoroidal Space Using a 250 Micron Flexible Microcatheter," PLOS One, vol. 6, Issue 2, e17140 (Feb. 2011).
Vandenberghe, L., et al., "Dosage Thresholds for AAV2 and AAV8 Photoreceptor Gene Therapy in Monkey," Gene Therapy, vol. 3, Issue 88, (Jun. 22, 2011).
Vandenberghe, L. H., et al., "Novel Adeno-Associated Viral Vectors for Retinal Gene Therapy," Gene Therapy, vol. 19, pp. 162-168 (Feb. 2012) (Published on-line Oct. 13, 2011).
Vandenberghe, L. H., "What is Next for Retinal Gene Therapy?" Cold Spring Harbor Perspectives in Medicine, Cold Spring Harbor Laboratory Press pp. 1-10 (Apr. 15, 2015).
Varadi, K., et al. "Novel Random Peptide Libraries Displayed on AAV Serotype 9 for Selection of Endothelial Cell-Directed Gene Transfer Vectors," Gene Therapy, vol. 19, pp. 800-809 (Aug. 2012).
Xie, Q., et al., The Atomic Structure of Adeno-Associated Virus (AAV-2), a Vector for Human Gene Therapy, PNAS, vol. 99, No. 16, pp. 10405-10410 (Aug. 6, 2002).

* cited by examiner

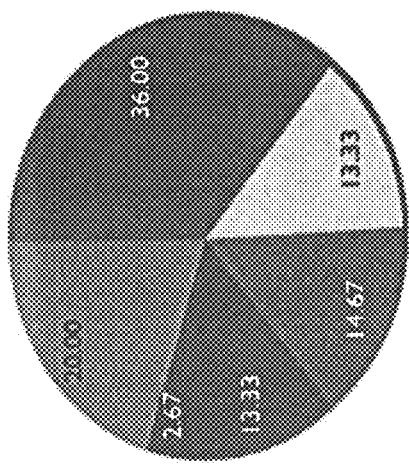
FIGURE 4A  Round 3
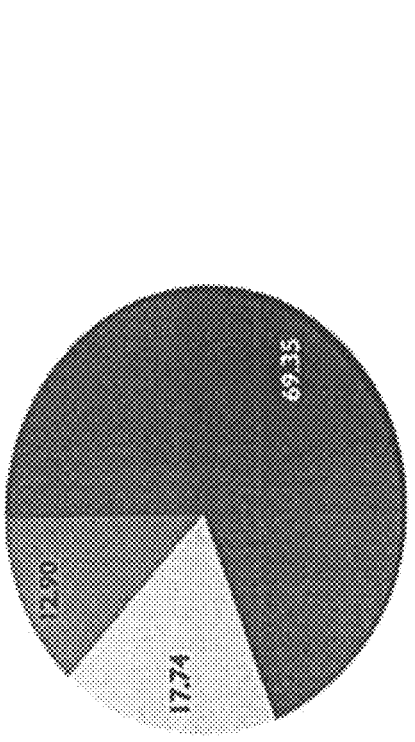
FIGURE 4B  Round 4
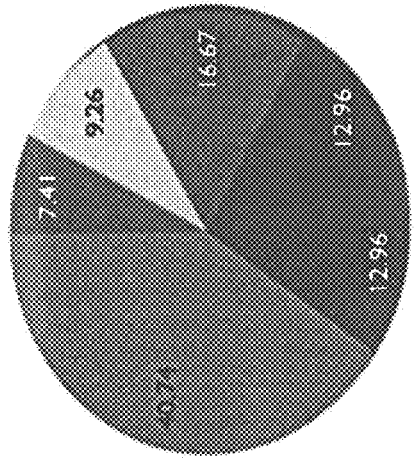
FIGURE 4C  Round 5
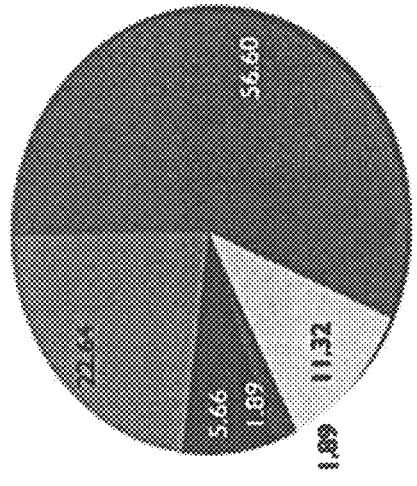
FIGURE 4D  Round 6

FIGURE 6 (cont'd)

| | 200/198 | 210/208 | 220/218 | 230/228 |
|---|---|---|---|---|
| AAV1 (SEQ ID NO: 1)  | A  G P T T  A S G G G A P  A D N N E G A D G V G N A S G N W H |
| AAV2 (SEQ ID NO: 2)  | G  G T N T  A T G G G A P  A D N N E G A D G V G N S S G N W H |
| AAV3A (SEQ ID NO: 3) | S  G S N T  A S G G G A P  A D N N E G A D G V G N S S G N W H |
| AAV3B (SEQ ID NO: 4) | S  G S N T  A S G G G A P  A D N N E G A D G V G N S S G N W H |
| AAV4 (SEQ ID NO: 5)  | S D D S  R A A A G G A  —  B G G Q G A D G V G N A S G N W H |
| AAV5 (SEQ ID NO: 6)  | S  G A D T  S A G G G P  G D N N Q G A D G V G N A S G N W H |
| AAV6 (SEQ ID NO: 7)  | A  G P T T  A S G G G A P  A D N N E G A D G V G N A S G N W H |
| AAV7 (SEQ ID NO: 8)  | S  G S G T  A A G G G A P  A D N N E G A D G V G N A S G N W H |
| AAV8 (SEQ ID NO: 9)  | G  G P N T  A A G G G A P  A D N N E G A D G V G N A S G N W H |
| AAV9 (SEQ ID NO: 10) | G  G S T  A A G G G A P  A D N N E G A D G V G S S G N W H |
| AAV10 (SEQ ID NO: 11)| G  G S G T  A A G G G A P  A D N N E G A D G V G S S G N W H |

FIGURE 6 (cont'd)

| | 238 | 248 | 258 |
|---|---|---|---|
| AAV1 (SEQ ID NO: 1) | CDSTWLGDR | TTSTRTWAL | PTYNNHLYKQISS | 240 / 250 / 260 |
| AAV2 (SEQ ID NO: 2) | CDSTWLGDR | TTSTRTWAL | PTYNNHLYKQISS | 238 / 248 / 258 |
| AAV3A (SEQ ID NO: 3) | CDSTWLGDR | TTSTRTWAL | PTYNNHLYKQISS | 238 / 248 / 258 |
| AAV3B (SEQ ID NO: 4) | CDSQWLGDR | TTSTRTWAL | PTYNNHLYKQISS | 238 / 248 / 258 |
| AAV4 (SEQ ID NO: 5) | CDSTWLGHQ | TTSTRTW.L | PTYNHLYKRLGE | 232 / 242 / 252 |
| AAV5 (SEQ ID NO: 6) | CDSTWLGDR | TKSTRTWAL | PTYNHLYKRLGE | 228 / 238 / 248 |
| AAV6 (SEQ ID NO: 7) | CDSTWLGDR | TTSTRTWAL | PSYNHQYRELKS | 238 / 248 / 258 |
| AAV7 (SEQ ID NO: 8) | CDSTWLGDR | TTSTRTWAL | PTYNNHLYKQISS | 239 / 249 / 259 |
| AAV8 (SEQ ID NO: 9) | CDSTWLGDR | TTSTRTWAL | PTYNNHLYKQISS | 239 / 249 / 259 |
| AAV9 (SEQ ID NO: 10) | CDSTWLGDR | TTSTRTWAL | PTYNNHLYKQISN | 238 / 248 / 258 |
| AAV10 (SEQ ID NO: 11) | CDSTWLGDR | TTSTRTWAL | PTYNNHLYKQISN | 239 / 249 / 259 |

FIGURE 6 (cont'd)

| | | |
|---|---|---|
| AAV1 (SEQ ID NO: 1) | A--STGASNDNHYFGYSTPWGYFDFNRFHCHFSP | 270 280 290 |
| AAV2 (SEQ ID NO: 2) | Q--SGASNDNHYFGYSTPWGYFDFNRFHCHFSP | 266 276 286 |
| AAV3A (SEQ ID NO: 3) | Q--SGASNDNHYFGYSTPWGYFDFNRFHCHFSP | 266 276 286 |
| AAV3B (SEQ ID NO: 4) | Q--SGASNDNHYFGYSTPWGYFDFNRFHCHFSP | 266 276 286 |
| AAV4 (SEQ ID NO: 5) | SNQSNTYNGFSTPWGYFDFNRFHCHFSP | 257 267 277 |
| AAV5 (SEQ ID NO: 6) | GSMDG-SNANAYFGYSTPWGYFDFNRFHSHWSP | 258 267 277 |
| AAV6 (SEQ ID NO: 7) | A--STGASTNDNTYFGYSTPWGYFDFNRFHCHFSP | 267 277 287 |
| AAV7 (SEQ ID NO: 8) | T--TAGSTNDNTYFGYSTPWGYFDFNRFHCHFSP | 268 278 288 |
| AAV8 (SEQ ID NO: 9) | GTSGGATNDNTYFGYSTPWGYFDFNRFHCHFSP | 269 279 289 |
| AAV9 (SEQ ID NO: 10) | GTSGGSSNDNAYFGYSTPWGYFDFNRFHCHFSP | 268 278 288 |
| AAV10 (SEQ ID NO: 11) | GTSGGSTNDNTYFGYSTPWGYFDFNRFHCHFSP | 269 279 289 |

FIGURE 6 (cont'd)

| | 297/300 | 307/310 | 317/320 | 327/330 |
|---|---|---|---|---|
| AAV1 (SEQ ID NO: 1)  | RDWQRLINNWGFRPKRLNFKLFNIQVKEVTTN |
| AAV2 (SEQ ID NO: 2)  | 296 RDWQRLINNNWGFRPKRLNFKLFNIQVKEVTQN 326 |
| AAV3A (SEQ ID NO: 3) | 296 RDWQRLINNNWGFRPKKLSFKLFNIQVKEVTQN 326 |
| AAV3B (SEQ ID NO: 4) | 296 RDWQRLINNNWGFRPKKLSFKLFNIQVRGTQN 326 |
| AAV4 (SEQ ID NO: 5)  | 287 RDWQRLINNYWGFRPKAMRVSKTENIQVKEVTQN 317 |
| AAV5 (SEQ ID NO: 6)  | 287 RDWQRLINNNWGFRPKRLSFKLFNIQVKEVTTS 317 |
| AAV6 (SEQ ID NO: 7)  | 297 RDWQRLINNNWGFRPKRLNFKLFNIQVKEVTTN 327 |
| AAV7 (SEQ ID NO: 8)  | 298 RDWQRLINNNWGFRPKRLSFKLFNIQVKEVTTN 328 |
| AAV8 (SEQ ID NO: 9)  | 299 RDWQRLINNNWGFRPKRLSFKLFNIQVKEVTQN 329 |
| AAV9 (SEQ ID NO: 10) | 298 RDWQRLINNNWGFRPKRLSFKLFNIQVKEVTQN 328 |
| AAV10 (SEQ ID NO: 11)| 299 RDWQRLINNNWGFRPKRLSFKLFNIQVKEVTQN 329 |

FIGURE 6 (cont'd)

| | | | |
|---|---|---|---|
| AAV1 (SEQ ID NO: 1)  | SSFYCLEYFPSQMLRTGNNFTFSYTFEDV PFHS | 400/394 | 410/404 | 420/414 |
| AAV2 (SEQ ID NO: 2)  | SSFYCLEYFPSQMLRTGNNFTFSYTFEDV PFHS | 393 | 403 | 413 |
| AAV3A (SEQ ID NO: 3) | SSFYCLEYFPSQMLRTGNNFQFSYTFEDV PFHS | 393 | 403 | 413 |
| AAV3B (SEQ ID NO: 4) | SSFYCLEYFPSQMLRTGNNFQFSYTFEDV PFHS | 393 | 403 | 413 |
| AAV4 (SEQ ID NO: 5)  | NAFYCLEYFPSQMLRTGNNFQFSYTFEDV PFHS | 387 | 397 | 407 |
| AAV5 (SEQ ID NO: 6)  | SSFYCLEYFPSKMLRTGNNFEFTYNFEKV PFHS | 386 | 396 | 406 |
| AAV6 (SEQ ID NO: 7)  | SSFYCLEYFPSQMLRTGNNFTFSYTFEDV PFHS | 394 | 404 | 414 |
| AAV7 (SEQ ID NO: 8)  | SSFYCLEYFPSQMLRTGNNFEFSYSFEDV PFHS | 395 | 405 | 415 |
| AAV8 (SEQ ID NO: 9)  | SSFYCLEYFPSQMLRTGNNFEFSYSFEDV PFHS | 396 | 406 | 416 |
| AAV9 (SEQ ID NO: 10) | SSFYCLEYFPSQMLRTGNNFQFSYTFENV PFHS | 395 | 405 | 415 |
| AAV10 (SEQ ID NO: 11)| SSFYCLEYFPSQMLRTGNNFEFSYTFEDV PFHS | 396 | 406 | 416 |

FIGURE 6 (cont'd)

| Sequence | Numbering | Alignment (alignment positions 430, 440, 450, 460) |
| --- | --- | --- |
| AAV1 (SEQ ID NO: 1) | 424, 434, 444, 453 | SYAHSQSLDRLMNPLIDQYLYYLNRTQNQ-SGS |
| AAV2 (SEQ ID NO: 2) | 423, 433, 443, 452 | SYAHSQSLDRLMNPLIDQYLYYLSRT-NTPSGT |
| AAV3A (SEQ ID NO: 3) | 423, 433, 443, 453 | SYAHSQSLDRLMNPLIDQYLYYLNRTQGTTSGT |
| AAV3B (SEQ ID NO: 4) | 423, 433, 443, 453 | SYAHSQSLDRLMNPLIDQYLYYLNRTQGTTSGT |
| AAV4 (SEQ ID NO: 5) | 417, 427, 437, 447 | MYAHSQSLDRLMNPLIDQYLWGLQSTTTGTTLN |
| AAV5 (SEQ ID NO: 6) | 416, 426, 436, 446 | SFAPSQNLFKLANPLVDQYLYRFVSTNNTGG-- |
| AAV6 (SEQ ID NO: 7) | 424, 434, 444, 453 | SYAHSQSLDRLMNPLIDQYLYYLNRTQNQ-SGS |
| AAV7 (SEQ ID NO: 8) | 425, 435, 445, 455 | SYAHSQSLDRLMNPLIDQYLYYLARTQSNPGGT |
| AAV8 (SEQ ID NO: 9) | 426, 436, 446, 455 | SYAHSQSLDRLMNPLIDQYLYYLSRTQTT-GGT |
| AAV9 (SEQ ID NO: 10) | 425, 435, 445, 453 | SYAHSQSLDRLMNPLIDQYLYYLSKTIN--GSG |
| AAV10 (SEQ ID NO: 11) | 426, 436, 446, 455 | SYAHSQSLDRLMNPLIDQYLYYLSRTQST-GGT |

FIGURE 6 (cont'd)

```
                   470                480              490
                   463                473              483
AAV1  (SEQ ID NO: 1)   AQNKDLLFSRGSPAGMSVQPKNWLPGPCYRQQR
                       462                472              482
                       463                473              483
AAV2  (SEQ ID NO: 2)   TTQSRLQFSQAGASDIRDQSRNWLPGPCYRQQR
                       463                473              483
AAV3A (SEQ ID NO: 3)   TNQSRLLFSQAGPQSLSLQARNWLPGPCYRQQR
                       463                473              483
AAV3B (SEQ ID NO: 4)   TNQSRLLFSQAGPQSLSLQARNWLPGPCYRQQR
                       457                467              477
AAV4  (SEQ ID NO: 5)   AGTATTNFTKLRPTNFSNFKKNWLPGPSIKQQG
                       449                459              469
AAV5  (SEQ ID NO: 6)   ---QFNLLAGRYANTYKNWFPGPLGRTQG
                       463                473              483
AAV6  (SEQ ID NO: 7)   AQNKDLLFSRGSPAGMSVQPKNWLPGPCYRQQR
                       465                475              485
AAV7  (SEQ ID NO: 8)   AGNRELQFYQGGPSTLANQAKNWLPGPCYRQQR
                       465                475              485
AAV8  (SEQ ID NO: 9)   ANTQTLGFSQGGPNTMANQAKNWLPGPCYRQQR
                       463                473              483
AAV9  (SEQ ID NO: 10)  QMQQTLKFSVAGPSNMAVQGRNYLPGPSYRQQR
                       465                475              485
AAV10 (SEQ ID NO: 11)  QGTQQLLFSQAGPANMSAQAKNWLPGPCYRQQR
```

FIGURE 6 (cont'd)

```
                      530        540              550         560
                      518        528              538         547
                      517        527              537         546
AAV1 (SEQ ID NO: 1)   N PGTAMASHKDDEDKFFPMSGVMIF - GKESA
AAV2 (SEQ ID NO: 2)   N PGPAMASHKDDEEKFFPQSGVLIF - GKQGS
AAV3A (SEQ ID NO: 3)  N PGPAMASHKDDEEKFFPMHGNLIF - GKEGT
                      518        528              538         547
AAV3B (SEQ ID NO: 4)  N PGPAMASHKDDEEKFFPMHGNLIF - GKEGT
                      517        527              538         545
AAV4 (SEQ ID NO: 5)   A NPGPAMASHKDDEEKFFPMHGNLIF - GKEGT
                      504        514              535         534
AAV5 (SEQ ID NO: 6)   Q PPQPNGMTNNLQGSNTYALENTMIFNSQPAN
                      518        528              524         547
AAV6 (SEQ ID NO: 7)   N PGPAMASHKDDKFFPMSGVMIF - GKESA
                      520        530              538         549
AAV7 (SEQ ID NO: 8)   N PGPAMATHKDDEDRFFPSSGVLIF - GKTGA
                      520        530              540         549
AAV8 (SEQ ID NO: 9)   A NPGPAMATHKDDEERFFPSNGILIF - GKQNA
                      518        528              540         547
AAV9 (SEQ ID NO: 10)  A NPGPAMASHKEGEDRFFPSSGVLIF - GKQGT
                      520        530              540         549
AAV10 (SEQ ID NO: 11) N PGPAMATHKDDEERFFPSSGVLMF - GKQGA
```

FIGURE 6 (cont'd)

AAV1 (SEQ ID NO: 1)
AAV2 (SEQ ID NO: 2)
AAV3A (SEQ ID NO: 3)
AAV3B (SEQ ID NO: 4)
AAV4 (SEQ ID NO: 5)
AAV5 (SEQ ID NO: 6)
AAV6 (SEQ ID NO: 7)
AAV7 (SEQ ID NO: 8)
AAV8 (SEQ ID NO: 9)
AAV9 (SEQ ID NO: 10)
AAV10 (SEQ ID NO: 11)

FIGURE 6 (cont'd)

| | | | | | | |
|---|---|---|---|---|---|---|
| AAV1 (SEQ ID NO: 1) | YLQGPIWAKI PHTDGHFHPS PLMGGFGLKH PPP | 615 | 624 | 630 | 635 | 645 |
| | | | | 640 | 650 | 660 |
| AAV2 (SEQ ID NO: 2) | YLQGPIWAKI PHTDGHFHPS PLMGGFGLKH PPP | 615 | 624 | 634 | 644 |
| AAV3A (SEQ ID NO: 3) | YLQGPIWAKI PHTDGHFHPS PLMGGFGLKH PPP | 615 | 625 | 635 | 645 |
| AAV3B (SEQ ID NO: 4) | YLQGPIWAKI PHTDGHFHPS PLMGGFGLKH PPP | 615 | 625 | 635 | 645 |
| AAV4 (SEQ ID NO: 5) | YLQGPIWAKI PHTDGHFHPS PLMGGFGLKH PPP | 613 | 623 | 633 | 643 |
| AAV5 (SEQ ID NO: 6) | YLQGPIWAKI PHTGAHFHPS PAMGGFGLKH PPP | 604 | 614 | 624 | 634 |
| AAV6 (SEQ ID NO: 7) | YLQGPIWAKI PHTDGHFHPS PLMGGFGLKH PPP | 615 | 625 | 635 | 645 |
| AAV7 (SEQ ID NO: 8) | YLQGPIWAKI PHTDGNFHPS PLMGGFGLKH PPP | 616 | 626 | 636 | 646 |
| AAV8 (SEQ ID NO: 9) | YLQGPIWAKI PHTDGNFHPS PLMGGFGLKH PPP | 617 | 627 | 637 | 647 |
| AAV9 (SEQ ID NO: 10) | YLQGPIWAKI PHTDGNFHPS PLMGGFGLKH PPP | 615 | 625 | 635 | 645 |
| AAV10 (SEQ ID NO: 11) | YLQGPIWAKI PHTDGNFHPS PLMGGFGLKH PPP | 617 | 627 | 637 | 647 |

FIGURE 6 (cont'd)

```
                                670       680              690
                                655       665              675
AAV1  (SEQ ID NO: 1)   QLEKNTPVPANPPAEFSATKFASFITQYSTGQ
                                654       664              674
AAV2  (SEQ ID NO: 2)   QLEKNTPVPANPSTTFSAAKFASFITQYSTGQ
                                655       665              675
AAV3A (SEQ ID NO: 3)   QLEKNTPVPANPPTTFSPAKFASFITQYSTGQ
                                655       665              675
AAV3B (SEQ ID NO: 4)   QLEKNTPVPANPPTTFSPAKFASFITQYSTGQ
                                653       663              673
AAV4  (SEQ ID NO: 5)   QLFKNTPVPANPATTFSSTPVNSFITQYSTGQ
                                644       653              663
AAV5  (SEQ ID NO: 6)   QLEKNTPVPGN-ITSFSDVPVSSFITQYSTGQ
                                655       665              675
AAV6  (SEQ ID NO: 7)   QLEKNTPVPANPATKFSATKFASFITQYSTGQ
                                656       666              676
AAV7  (SEQ ID NO: 8)   QLEKNTPVPANPPETPAKFASFITQYSTGQ
                                657       667              677
AAV8  (SEQ ID NO: 9)   QLEKNTPVPADPPTTFNQSKLNSFITQYSTGQ
                                655       665              675
AAV9  (SEQ ID NO: 10)  QLEKNTPVPADPPTAFNKDKLNSFITQYSTGQ
                                657       667              677
AAV10 (SEQ ID NO: 11)  QLEKNTPVPADPPTTFSQAKLASFITQYSTGQ
```

FIGURE 6 (cont'd)

| | | | |
|---|---|---|---|
| AAV1 (SEQ ID NO: 1) | 685 SVETTWELQKENSKRWNPE 700 IQYTSNYAKSAN 720 705 |
| AAV2 (SEQ ID NO: 2) | 684 SVETTWELQKENSKRWNPE IQYTSNYNKSVN 704 |
| AAV3A (SEQ ID NO: 3) | 685 SVETTWELQKENSKRWNPE IQYTSNYNKSVN 705 |
| AAV3B (SEQ ID NO: 4) | 685 SVETTWELQKENSKRWNPE IQYTSNYNKSVN 705 |
| AAV4 (SEQ ID NO: 5) | 683 SLDRLMNPLIDQYLYYLSRTQ IQYTSNYAKSVN 703 |
| AAV5 (SEQ ID NO: 6) | 673 SLDRLMNPLIDQYLYYLSRTQ FTSNYGQNSL 693 |
| AAV6 (SEQ ID NO: 7) | 685 SVETTWELQKENSKRWNPE IQTNNYNDPQF 705 |
| AAV7 (SEQ ID NO: 8) | 686 SVETTWELQKENSKRWNPE IQYTSNYAKSANT 706 |
| AAV8 (SEQ ID NO: 9) | 687 SVETTWELQKENSKRWNPE IQYTSNFEKQTGV 707 |
| AAV9 (SEQ ID NO: 10) | 685 SVETTWELQKENSKRWNPE IQYTSNYYKSNN 705 |
| AAV10 (SEQ ID NO: 11) | 687 SVETTWELQKENSKRWNPE IQYTSNYYKSTN 707 |

FIGURE 6 (cont'd)

| | 730 | 740 | 750 752 |
|---|---|---|---|
| AAV1 (SEQ ID NO: 1) | DFT...DNNGVYT...PR.P...LG.TRY...TR.P | 715 | 724 736/737 |
| AAV2 (SEQ ID NO: 2) | DFT...DTNGVYS...PR.P...LG.TRY...TRN | 715 725 | 736 |
| AAV3A (SEQ ID NO: 3) | DFT...DTNGVYS...PR.P...LG.TRY...TRN | 715 725 | 736 |
| AAV3B (SEQ ID NO: 4) | DFT...DTNGVYS...PR.P...LG.TRY...TRN | 713 723 | 735 |
| AAV4 (SEQ ID NO: 5) | NAPDAAGKYT...PRA...LG.TRY...TRH | 703 713 | 725 |
| AAV5 (SEQ ID NO: 6) | DFA.PDSTG.YR...T.R.P...LG.TRY...TR.P | 715 725 | 737 |
| AAV6 (SEQ ID NO: 7) | DFT...DNNGVYT...PR.P...LG.TRY...TR.P | 716 726 | 738 |
| AAV7 (SEQ ID NO: 8) | DFA.NT.GVYS...PR.P...LG.TRY...TRN | 717 727 | 739 |
| AAV8 (SEQ ID NO: 9) | DFA.NT.GVYS...PR.P...LG.TRY...TR.N | 715 725 | 737 |
| AAV9 (SEQ ID NO: 10) | DFA.NT.GVYS...PR.P...LG.TRY...TRN | 717 727 | 738 |
| AAV10 (SEQ ID NO: 11) | DFA.NT.GTYS...PR.P...LG.TRY...TRN | | |

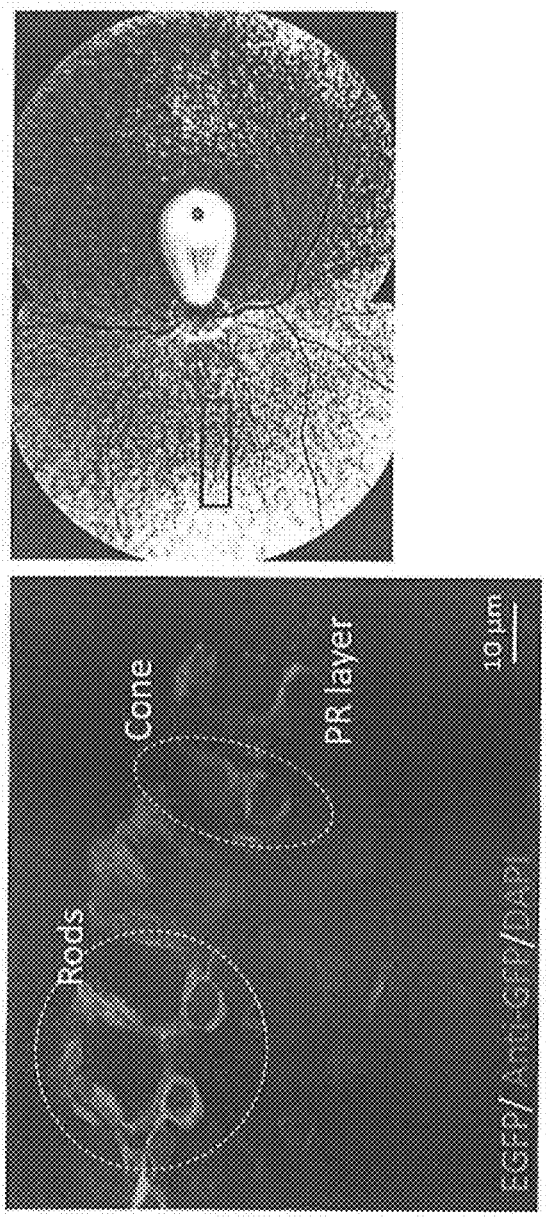
FIGURE 10B
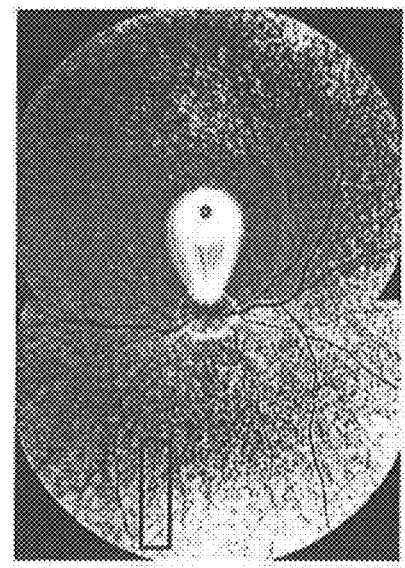
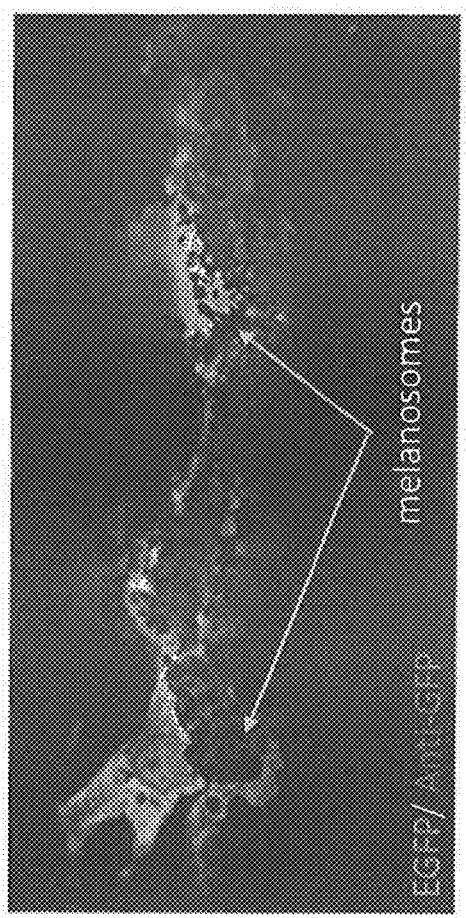
FIGURE 10C

SEQUENCE LISTING

<160> NUMBER OF SEQ ID NOS: 64

<210> SEQ ID NO 1
<211> LENGTH: 736
<212> TYPE: PRT
<213> ORGANISM: Adeno-associated virus 1

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

```
Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                    325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                    405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                    485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                    565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                    645                 650                 655

Asn Pro Pro Ala Glu Phe Ser Ala Thr Lys Phe Ala Ser Phe Ile Thr
            660                 665                 670
```

```
Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 2
<211> LENGTH: 735
<212> TYPE: PRT
<213> ORGANISM: Adeno-associated virus 2

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320
```

```
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
                355                 360                 365
Val Phe Met Val Pro Gln Tyr Gly Tyr Leu Thr Leu Asn Asn Gly Ser
            370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Arg Thr
            435                 440                 445
Asn Thr Pro Ser Gly Thr Thr Thr Gln Ser Arg Leu Gln Phe Ser Gln
        450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
            515                 520                 525
Asp Glu Glu Lys Phe Phe Pro Gln Ser Gly Val Leu Ile Phe Gly Lys
            530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
        610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
                660                 665                 670
Tyr Ser Thr Gly Gln Val Ser Val Glu Ile Glu Trp Glu Leu Gln Lys
            675                 680                 685
Glu Asn Ser Lys Arg Trp Asn Pro Glu Ile Gln Tyr Thr Ser Asn Tyr
            690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735
```

```
<210> SEQ ID NO 3
<211> LENGTH: 736
<212> TYPE: PRT
<213> ORGANISM: Adeno-associated virus 3A

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
    130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380
```

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Gly Thr Val Asn His Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 4
<211> LENGTH: 736
<212> TYPE: PRT
<213> ORGANISM: Adeno-associated virus 3B

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro

```
                20                  25                  30
Lys Ala Asn Gln Gln His Gln Asp Asn Arg Arg Gly Leu Val Leu Pro
            35                  40                  45
Gly Tyr Lys Tyr Leu Gly Pro Gly Asn Gly Leu Asp Lys Gly Glu Pro
50                  55                  60
Val Asn Glu Ala Asp Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
            85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Ile Leu Glu Pro
            115                 120                 125
Leu Gly Leu Val Glu Glu Ala Ala Lys Thr Ala Pro Gly Lys Lys Arg
            130                 135                 140
Pro Val Asp Gln Ser Pro Gln Glu Pro Asp Ser Ser Gly Val Gly
145                 150                 155                 160
Lys Ser Gly Lys Gln Pro Ala Arg Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Ala Pro Thr Ser Leu Gly Ser Asn Thr Met Ala Ser Gly Gly Gly
            195                 200                 205
Ala Pro Met Ala Asp Asn Asn Glu Gly Ala Asp Gly Val Gly Asn Ser
            210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
                260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
            290                 295                 300
Gly Phe Arg Pro Lys Lys Leu Ser Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
            370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Asn Arg Thr
            435                 440                 445
```

Gln Gly Thr Thr Ser Gly Thr Thr Asn Gln Ser Arg Leu Leu Phe Ser
            450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 5
<211> LENGTH: 734
<212> TYPE: PRT
<213> ORGANISM: Adeno-associated virus 4

<400> SEQUENCE: 5

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp

```
                    85                  90                  95
Ala Glu Phe Gln Gln Arg Leu Gln Gly Asp Thr Ser Phe Gly Gly Asn
                100                 105                 110

Leu Gly Arg Ala Val Phe Gln Ala Lys Lys Arg Val Leu Glu Pro Leu
                115                 120                 125

Gly Leu Val Glu Gln Ala Gly Glu Thr Ala Pro Gly Lys Lys Arg Pro
                130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Leu Val Phe Glu Asp Glu Thr
                165                 170                 175

Gly Ala Gly Asp Gly Pro Pro Glu Gly Ser Thr Ser Gly Ala Met Ser
                180                 185                 190

Asp Asp Ser Glu Met Arg Ala Ala Gly Gly Ala Ala Val Glu Gly
                195                 200                 205

Gly Gln Gly Ala Asp Gly Val Gly Asn Ala Ser Gly Asp Trp His Cys
                210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
                260                 265                 270

Phe Asp Phe Asn Arg Phe His Cys His Phe Ser Pro Arg Asp Trp Gln
                275                 280                 285

Arg Leu Ile Asn Asn Asn Trp Gly Met Arg Pro Lys Ala Met Arg Val
                290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
                340                 345                 350

Leu Pro Pro Phe Pro Asn Asp Val Phe Met Val Pro Gln Tyr Gly Tyr
                355                 360                 365

Cys Gly Leu Val Thr Gly Asn Thr Ser Gln Gln Gln Thr Asp Arg Asn
                370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
                420                 425                 430

Asp Gln Tyr Leu Trp Gly Leu Gln Ser Thr Thr Thr Gly Thr Thr Leu
                435                 440                 445

Asn Ala Gly Thr Ala Thr Thr Asn Phe Thr Lys Leu Arg Pro Thr Asn
                450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
                500                 505                 510
```

```
Arg Trp Ser Ala Leu Thr Pro Gly Pro Pro Met Ala Thr Ala Gly Pro
            515                 520                 525

Ala Asp Ser Lys Phe Ser Asn Ser Gln Leu Ile Phe Ala Gly Pro Lys
        530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
        595                 600                 605

Asp Ile Tyr Tyr Gln Gly Pro Ile Trp Ala Lys Ile Pro His Thr Asp
    610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
        675                 680                 685

Arg Ser Lys Arg Trp Asn Pro Glu Val Gln Phe Thr Ser Asn Tyr Gly
    690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 6
<211> LENGTH: 724
<212> TYPE: PRT
<213> ORGANISM: Adeno-associated virus 5

<400> SEQUENCE: 6

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
```

```
            145                 150                 155                 160
Lys Pro Ser Thr Ser Ser Asp Ala Glu Ala Gly Pro Ser Gly Ser Gln
                    165                 170                 175
Gln Leu Gln Ile Pro Ala Gln Pro Ala Ser Ser Leu Gly Ala Asp Thr
                    180                 185                 190
Met Ser Ala Gly Gly Gly Pro Leu Gly Asp Asn Gln Gly Ala
                    195                 200                 205
Asp Gly Val Gly Asn Ala Ser Gly Asp Trp His Cys Asp Ser Thr Trp
            210                 215                 220
Met Gly Asp Arg Val Val Thr Lys Ser Thr Arg Thr Trp Val Leu Pro
225                 230                 235                 240
Ser Tyr Asn Asn His Gln Tyr Arg Glu Ile Lys Ser Gly Ser Val Asp
                    245                 250                 255
Gly Ser Asn Ala Asn Ala Tyr Phe Gly Tyr Ser Thr Pro Trp Gly Tyr
                    260                 265                 270
Phe Asp Phe Asn Arg Phe His Ser His Trp Ser Pro Arg Asp Trp Gln
                    275                 280                 285
Arg Leu Ile Asn Asn Tyr Trp Gly Phe Arg Pro Arg Ser Leu Arg Val
                    290                 295                 300
Lys Ile Phe Asn Ile Gln Val Lys Glu Val Thr Val Gln Asp Ser Thr
305                 310                 315                 320
Thr Thr Ile Ala Asn Asn Leu Thr Ser Thr Val Gln Val Phe Thr Asp
                    325                 330                 335
Asp Asp Tyr Gln Leu Pro Tyr Val Val Gly Asn Gly Thr Glu Gly Cys
                    340                 345                 350
Leu Pro Ala Phe Pro Pro Gln Val Phe Thr Leu Pro Gln Tyr Gly Tyr
                    355                 360                 365
Ala Thr Leu Asn Arg Asp Asn Thr Glu Asn Pro Thr Glu Arg Ser Ser
                    370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                    405                 410                 415
Phe Ala Pro Ser Gln Asn Leu Phe Lys Leu Ala Asn Pro Leu Val Asp
                    420                 425                 430
Gln Tyr Leu Tyr Arg Phe Val Ser Thr Asn Asn Thr Gly Gly Val Gln
                    435                 440                 445
Phe Asn Lys Asn Leu Ala Gly Arg Tyr Ala Asn Thr Tyr Lys Asn Trp
                    450                 455                 460
Phe Pro Gly Pro Met Gly Arg Thr Gln Gly Trp Asn Leu Gly Ser Gly
465                 470                 475                 480
Val Asn Arg Ala Ser Val Ser Ala Phe Ala Thr Thr Asn Arg Met Glu
                    485                 490                 495
Leu Glu Gly Ala Ser Tyr Gln Val Pro Pro Gln Pro Asn Gly Met Thr
                    500                 505                 510
Asn Asn Leu Gln Gly Ser Asn Thr Tyr Ala Leu Glu Asn Thr Met Ile
                    515                 520                 525
Phe Asn Ser Gln Pro Ala Asn Pro Gly Thr Thr Ala Thr Tyr Leu Glu
                    530                 535                 540
Gly Asn Met Leu Ile Thr Ser Glu Ser Glu Thr Gln Pro Val Asn Arg
545                 550                 555                 560
Val Ala Tyr Asn Val Gly Gly Gln Met Ala Thr Asn Asn Gln Ser Ser
                    565                 570                 575
```

```
Thr Thr Ala Pro Ala Thr Gly Thr Tyr Asn Leu Gln Glu Ile Val Pro
            580                 585                 590
Gly Ser Val Trp Met Glu Arg Asp Val Tyr Leu Gln Gly Pro Ile Trp
        595                 600                 605
Ala Lys Ile Pro Glu Thr Gly Ala His Phe His Pro Ser Pro Ala Met
    610                 615                 620
Gly Gly Phe Gly Leu Lys His Pro Pro Met Met Leu Ile Lys Asn
625                 630                 635                 640
Thr Pro Val Pro Gly Asn Ile Thr Ser Phe Ser Asp Val Pro Val Ser
                645                 650                 655
Ser Phe Ile Thr Gln Tyr Ser Thr Gly Gln Val Thr Val Glu Met Glu
            660                 665                 670
Trp Glu Leu Lys Lys Glu Asn Ser Lys Arg Trp Asn Pro Glu Ile Gln
        675                 680                 685
Tyr Thr Asn Asn Tyr Asn Asp Pro Gln Phe Val Asp Phe Ala Pro Asp
    690                 695                 700
Ser Thr Gly Glu Tyr Arg Thr Thr Arg Pro Ile Gly Thr Arg Tyr Leu
705                 710                 715                 720
Thr Arg Pro Leu

<210> SEQ ID NO 7
<211> LENGTH: 736
<212> TYPE: PRT
<213> ORGANISM: Adeno-associated virus 6

<400> SEQUENCE: 7

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Phe Gly Leu Val Glu Glu Gly Ala Lys Thr Ala Pro Gly Lys Lys Arg
    130                 135                 140
Pro Val Glu Gln Ser Pro Gln Glu Pro Asp Ser Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Thr Pro Ala Ala Val Gly Pro Thr Thr Met Ala Ser Gly Gly Gly
        195                 200                 205
Ala Pro Met Ala Asp Asn Asn Glu Gly Ala Asp Gly Val Gly Asn Ala
    210                 215                 220
```

```
Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
        260                 265                 270

Tyr Phe Gly Tyr Ser Thr Pro Trp Gly Tyr Phe Asp Phe Asn Arg Phe
    275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
            325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640
```

-continued

```
Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 8
<211> LENGTH: 737
<212> TYPE: PRT
<213> ORGANISM: Adeno-associated virus 7

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285
```

```
Phe His Cys His Phe Ser Pro Arg Asp Trp Gln Arg Leu Ile Asn Asn
    290                 295                 300
Asn Trp Gly Phe Arg Pro Lys Lys Leu Arg Phe Lys Leu Phe Asn Ile
305                 310                 315                 320
Gln Val Lys Glu Val Thr Thr Asn Asp Gly Val Thr Thr Ile Ala Asn
                325                 330                 335
Asn Leu Thr Ser Thr Ile Gln Val Phe Ser Asp Ser Glu Tyr Gln Leu
            340                 345                 350
Pro Tyr Val Leu Gly Ser Ala His Gln Gly Cys Leu Pro Pro Phe Pro
        355                 360                 365
Ala Asp Val Phe Met Ile Pro Gln Tyr Gly Tyr Leu Thr Leu Asn Asn
    370                 375                 380
Gly Ser Gln Ser Val Gly Arg Ser Ser Phe Tyr Cys Leu Glu Tyr Phe
385                 390                 395                 400
Pro Ser Gln Met Leu Arg Thr Gly Asn Asn Phe Glu Phe Ser Tyr Ser
                405                 410                 415
Phe Glu Asp Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ala
        435                 440                 445
Arg Thr Gln Ser Asn Pro Gly Gly Thr Ala Gly Asn Arg Glu Leu Gln
    450                 455                 460
Phe Tyr Gln Gly Gly Pro Ser Thr Met Ala Glu Gln Ala Lys Asn Trp
465                 470                 475                 480
Leu Pro Gly Pro Cys Phe Arg Gln Gln Arg Val Ser Lys Thr Leu Asp
                485                 490                 495
Gln Asn Asn Asn Ser Asn Phe Ala Trp Thr Gly Ala Thr Lys Tyr His
            500                 505                 510
Leu Asn Gly Arg Asn Ser Leu Val Asn Pro Gly Val Ala Met Ala Thr
        515                 520                 525
His Lys Asp Asp Glu Asp Arg Phe Phe Pro Ser Ser Gly Val Leu Ile
    530                 535                 540
Phe Gly Lys Thr Gly Ala Thr Asn Lys Thr Thr Leu Glu Asn Val Leu
545                 550                 555                 560
Met Thr Asn Glu Glu Glu Ile Arg Pro Thr Asn Pro Val Ala Thr Glu
                565                 570                 575
Glu Tyr Gly Ile Val Ser Ser Asn Leu Gln Ala Ala Asn Thr Ala Ala
            580                 585                 590
Gln Thr Gln Val Val Asn Asn Gln Gly Ala Leu Pro Gly Met Val Trp
        595                 600                 605
Gln Asn Arg Asp Val Tyr Leu Gln Gly Pro Ile Trp Ala Lys Ile Pro
    610                 615                 620
His Thr Asp Gly Asn Phe His Pro Ser Pro Leu Met Gly Gly Phe Gly
625                 630                 635                 640
Leu Lys His Pro Pro Pro Gln Ile Leu Ile Lys Asn Thr Pro Val Pro
                645                 650                 655
Ala Asn Pro Pro Glu Val Phe Thr Pro Ala Lys Phe Ala Ser Phe Ile
            660                 665                 670
Thr Gln Tyr Ser Thr Gly Gln Val Ser Val Glu Ile Glu Trp Glu Leu
        675                 680                 685
Gln Lys Glu Asn Ser Lys Arg Trp Asn Pro Glu Ile Gln Tyr Thr Ser
    690                 695                 700
```

-continued

```
Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
            725                 730                 735

Leu

<210> SEQ ID NO 9
<211> LENGTH: 738
<212> TYPE: PRT
<213> ORGANISM: Adeno-associated virus 8

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335
```

```
Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 10
```

```
<211> LENGTH: 736
<212> TYPE: PRT
<213> ORGANISM: Adeno-associated virus 9

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
```

```
                385                 390                 395                 400
        Pro Ser Gln Met Leu Arg Thr Gly Asn Asn Phe Gln Phe Ser Tyr Glu
                            405                 410                 415

Phe Glu Asn Val Pro Phe His Ser Ser Tyr Ala His Ser Gln Ser Leu
                        420                 425                 430

Asp Arg Leu Met Asn Pro Leu Ile Asp Gln Tyr Leu Tyr Tyr Leu Ser
                        435                 440                 445

Lys Thr Ile Asn Gly Ser Gly Gln Asn Gln Gln Thr Leu Lys Phe Ser
                    450                 455                 460

Val Ala Gly Pro Ser Asn Met Ala Val Gln Gly Arg Asn Tyr Ile Pro
        465                 470                 475                 480

Gly Pro Ser Tyr Arg Gln Gln Arg Val Ser Thr Thr Val Thr Gln Asn
                            485                 490                 495

Asn Asn Ser Glu Phe Ala Trp Pro Gly Ala Ser Ser Trp Ala Leu Asn
                        500                 505                 510

Gly Arg Asn Ser Leu Met Asn Pro Gly Pro Ala Met Ala Ser His Lys
                        515                 520                 525

Glu Gly Glu Asp Arg Phe Phe Pro Leu Ser Gly Ser Leu Ile Phe Gly
                    530                 535                 540

Lys Gln Gly Thr Gly Arg Asp Asn Val Asp Ala Asp Lys Val Met Ile
        545                 550                 555                 560

Thr Asn Glu Glu Glu Ile Lys Thr Thr Asn Pro Val Ala Thr Glu Ser
                            565                 570                 575

Tyr Gly Gln Val Ala Thr Asn His Gln Ser Ala Gln Ala Gln Ala Gln
                        580                 585                 590

Thr Gly Trp Val Gln Asn Gln Gly Ile Leu Pro Gly Met Val Trp Gln
                        595                 600                 605

Asp Arg Asp Val Tyr Leu Gln Gly Pro Ile Trp Ala Lys Ile Pro His
                    610                 615                 620

Thr Asp Gly Asn Phe His Pro Ser Pro Leu Met Gly Gly Phe Gly Met
        625                 630                 635                 640

Lys His Pro Pro Pro Gln Ile Leu Ile Lys Asn Thr Pro Val Pro Ala
                            645                 650                 655

Asp Pro Pro Thr Ala Phe Asn Lys Asp Lys Leu Asn Ser Phe Ile Thr
                        660                 665                 670

Gln Tyr Ser Thr Gly Gln Val Ser Val Glu Ile Glu Trp Glu Leu Gln
                        675                 680                 685

Lys Glu Asn Ser Lys Arg Trp Asn Pro Glu Ile Gln Tyr Thr Ser Asn
                    690                 695                 700

Tyr Tyr Lys Ser Asn Asn Val Glu Phe Ala Val Asn Thr Glu Gly Val
        705                 710                 715                 720

Tyr Ser Glu Pro Arg Pro Ile Gly Thr Arg Tyr Leu Thr Arg Asn Leu
                            725                 730                 735

<210> SEQ ID NO 11
<211> LENGTH: 738
<212> TYPE: PRT
<213> ORGANISM: Adeno-associated virus 10

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30
```

-continued

```
Lys Ala Asn Gln Gln Lys Gln Asp Gly Arg Gly Leu Val Leu Pro
             35                  40                  45
Gly Tyr Lys Tyr Leu Gly Pro Phe Asn Gly Leu Asp Lys Gly Glu Pro
 50                  55                  60
Val Asn Ala Ala Asp Ala Ala Leu Glu His Asp Lys Ala Tyr Asp
 65                  70                  75                  80
Gln Gln Leu Lys Ala Gly Asp Asn Pro Tyr Leu Arg Tyr Asn His Ala
             85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Ala Ala Lys Thr Ala Pro Gly Lys Lys Arg
        130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Lys Lys Arg Leu Asn Phe Gly Gln
                165                 170                 175
Thr Gly Glu Ser Glu Ser Val Pro Asp Pro Gln Pro Ile Gly Glu Pro
            180                 185                 190
Pro Ala Gly Pro Ser Gly Leu Gly Ser Gly Thr Met Ala Ala Gly Gly
        195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Ser Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
        355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Thr Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
        435                 440                 445
Ser Arg Thr Gln Ser Thr Gly Gly Thr Gln Gly Thr Gln Gln Leu Leu
```

```
                 450                 455                 460
Phe Ser Gln Ala Gly Pro Ala Asn Met Ser Ala Gln Ala Lys Asn Trp
465                 470                 475                 480

Leu Pro Gly Pro Cys Tyr Arg Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
            530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Ala Asn Thr Gly
                580                 585                 590

Pro Ile Val Gly Asn Val Asn Ser Gln Gly Ala Leu Pro Gly Met Val
                595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 12
<211> LENGTH: 738
<212> TYPE: PRT
<213> ORGANISM: Adeno-associated virus rh10

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
```

-continued

```
                85                  90                  95
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
            130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
            195                 200                 205

Gly Ala Pro Met Ala Asp Asn Glu Gly Ala Asp Gly Val Gly Ser
            210                 215                 220

Ser Ser Gly Asn Trp His Cys Asp Ser Thr Trp Leu Gly Asp Gly Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Ser Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
            450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asp Asn Ser Asn Phe Ala Trp Thr Gly Ala Thr Lys Tyr His
            500                 505                 510
```

```
            Leu Asn Gly Arg Asp Ser Leu Val Asn Pro Gly Val Ala Met Ala Thr
                    515                 520                 525

His Lys Asp Asp Glu Glu Arg Phe Phe Pro Ser Ser Gly Val Leu Met
                530                 535                 540

Phe Gly Lys Gln Gly Ala Gly Lys Asp Asn Val Asp Tyr Ser Ser Val
        545                 550                 555                 560

Met Leu Thr Ser Glu Glu Glu Ile Lys Thr Thr Asn Pro Val Ala Thr
                        565                 570                 575

Glu Gln Tyr Gly Val Val Ala Asp Asn Leu Gln Gln Asn Ala Ala
                    580                 585                 590

Pro Ile Val Gly Ala Val Asn Ser Gln Gly Ala Leu Pro Gly Met Val
                    595                 600                 605

Trp Gln Asn Arg Asp Val Tyr Leu Gln Gly Pro Ile Trp Ala Lys Ile
                    610                 615                 620

Pro His Thr Asp Gly Asn Phe His Pro Ser Pro Leu Met Gly Gly Phe
        625                 630                 635                 640

Gly Leu Lys His Pro Pro Pro Gln Ile Leu Ile Lys Asn Thr Pro Val
                        645                 650                 655

Pro Ala Asp Pro Pro Thr Thr Phe Ser Gln Ala Lys Leu Ala Ser Phe
                    660                 665                 670

Ile Thr Gln Tyr Ser Thr Gly Gln Val Ser Val Glu Ile Glu Trp Glu
                    675                 680                 685

Leu Gln Lys Glu Asn Ser Lys Arg Trp Asn Pro Glu Ile Gln Tyr Thr
                    690                 695                 700

Ser Asn Tyr Tyr Lys Ser Thr Asn Val Asp Phe Ala Val Asn Thr Asp
        705                 710                 715                 720

Gly Thr Tyr Ser Glu Pro Arg Pro Ile Gly Thr Arg Tyr Leu Thr Arg
                        725                 730                 735

Asn Leu

<210> SEQ ID NO 13
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 13

Gln Ala Asp Thr Thr Lys Asn
1               5

<210> SEQ ID NO 14
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 14

Ile Ser Asp Gln Thr Lys His
1               5

<210> SEQ ID NO 15
<211> LENGTH: 7
<212> TYPE: PRT
<213> ORGANISM: Artificial Sequence
<220> FEATURE:
<223> OTHER INFORMATION: heterologous peptide insertion
```

```
<400> SEQUENCE: 15

Ala Ser Asp Ser Thr Lys Ala
1               5

<210> SEQ ID NO 16
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 16

Asn Gln Asp Tyr Thr Lys Thr
1               5

<210> SEQ ID NO 17
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 17

His Asp Ile Thr Lys Asn Ile
1               5

<210> SEQ ID NO 18
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 18

His Pro Asp Thr Thr Lys Asn
1               5

<210> SEQ ID NO 19
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 19

His Gln Asp Thr Thr Lys Asn
1               5

<210> SEQ ID NO 20
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 20

Asn Lys Thr Thr Asn Lys Asp
1               5

<210> SEQ ID NO 21
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 21
```

```
Ile Ser Asn Glu Asn Glu His
1               5

<210> SEQ ID NO 22
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 22

Gln Ala Asn Ala Asn Glu Asn
1               5

<210> SEQ ID NO 23
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 23

Gly Lys Ser Lys Val Ile Asp
1               5

<210> SEQ ID NO 24
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 24

Thr Asn Arg Thr Ser Pro Asp
1               5

<210> SEQ ID NO 25
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 25

Pro Asn Ser Thr His Gly Ser
1               5

<210> SEQ ID NO 26
<211> LENGTH: 7
<212> TYPE: PRT
<213> ORGANISM: Artificial Sequence
<220> FEATURE:
<223> OTHER INFORMATION: heterologous peptide insertion

<400> SEQUENCE: 26

Lys Asp Arg Ala Pro Ser Thr
1               5

<210> SEQ ID NO 27
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 27
```

Leu Ala Gln Ala Asp Thr Thr Lys Asn Ala
1               5                   10

<210> SEQ ID NO 28
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 28

Leu Ala Ile Ser Asp Gln Thr Lys His Ala
1               5                   10

<210> SEQ ID NO 29
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 29

Leu Gly Ile Ser Asp Gln Thr Lys His Ala
1               5                   10

<210> SEQ ID NO 30
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 30

Leu Ala Ala Ser Asp Ser Thr Lys Ala Ala
1               5                   10

<210> SEQ ID NO 31
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 31

Leu Ala Asn Gln Asp Tyr Thr Lys Thr Ala
1               5                   10

<210> SEQ ID NO 32
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 32

Leu Ala His Asp Ile Thr Lys Asn Ile Ala
1               5                   10

<210> SEQ ID NO 33
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 33

Leu Ala His Pro Asp Thr Thr Lys Asn Ala

```
1               5                   10
```

<210> SEQ ID NO 34
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 34

```
Leu Ala His Gln Asp Thr Thr Lys Asn Ala
1               5                   10
```

<210> SEQ ID NO 35
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 35

```
Leu Ala Asn Lys Thr Thr Asn Lys Asp Ala
1               5                   10
```

<210> SEQ ID NO 36
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 36

```
Leu Pro Ile Ser Asn Glu Asn Glu His Ala
1               5                   10
```

<210> SEQ ID NO 37
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 37

```
Leu Pro Gln Ala Asn Ala Asn Glu Asn Ala
1               5                   10
```

<210> SEQ ID NO 38
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 38

```
Leu Ala Gly Lys Ser Lys Val Ile Asp Ala
1               5                   10
```

<210> SEQ ID NO 39
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 39

```
Leu Ala Thr Asn Arg Thr Ser Pro Asp Ala
1               5                   10
```

```
<210> SEQ ID NO 40
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 40

Leu Ala Pro Asn Ser Thr His Gly Ser Ala
1               5                   10

<210> SEQ ID NO 41
<211> LENGTH: 10
<212> TYPE: PRT
<213> ORGANISM: Artificial Sequence
<220> FEATURE:
<223> OTHER INFORMATION: heterologous peptide insertion

<400> SEQUENCE: 41

Leu Ala Lys Asp Arg Ala Pro Ser Thr Ala
1               5                   10

<210> SEQ ID NO 42
<211> LENGTH: 745
<212> TYPE: PRT
<213> ORGANISM: Artificial Sequence
<220> FEATURE:
<223> OTHER INFORMATION: Variant AAV capsid

<400> SEQUENCE: 42

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Ala Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220
```

```
Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Ile Ser Asp
            580                 585                 590

Gln Thr Lys His Ala Arg Gln Ala Ala Thr Ala Asp Val Asn Thr Gln
            595                 600                 605

Gly Val Leu Pro Gly Met Val Trp Gln Asp Arg Asp Val Tyr Leu Gln
            610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Pro Gln Ile
```

```
                    645                 650                 655
Leu Ile Lys Asn Thr Pro Val Pro Ala Asn Pro Ser Thr Thr Phe Ser
                660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
        690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
                740                 745

<210> SEQ ID NO 43
<211> LENGTH: 745
<212> TYPE: PRT
<213> ORGANISM: Artificial Sequence
<220> FEATURE:
<223> OTHER INFORMATION: AAV capsid variant

<400> SEQUENCE: 43

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
```

```
                260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
            290                 295                 300
Gly Phe Arg Pro Lys Arg Leu Lys Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
            370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Arg Thr
            435                 440                 445
Asp Thr Pro Ser Gly Thr Thr Thr Gln Ser Arg Leu Gln Phe Ser Gln
            450                 455                 460
Ala Gly Ala Ser Asp Ile Arg Asn Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
            515                 520                 525
Asp Glu Glu Lys Phe Phe Pro Gln Ser Gly Val Leu Ile Phe Gly Lys
            530                 535                 540
Gln Gly Ser Glu Lys Thr Ser Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Leu Ala Ile Ser Asp
            580                 585                 590
Gln Thr Lys His Ala Arg Gln Ala Ala Thr Ala Asp Val Asn Thr Gln
            595                 600                 605
Gly Val Leu Pro Gly Met Val Trp Gln Asp Arg Asp Val Tyr Leu Gln
            610                 615                 620
Gly Pro Ile Trp Ala Lys Ile Pro His Thr Asp Gly His Phe His Pro
625                 630                 635                 640
Ser Pro Leu Met Gly Gly Phe Gly Leu Lys His Pro Pro Pro Gln Ile
                645                 650                 655
Leu Ile Lys Asn Thr Pro Val Pro Ala Asn Pro Ser Thr Thr Phe Ser
                660                 665                 670
Ala Ala Lys Phe Ala Ser Phe Ile Thr Gln Tyr Ser Thr Gly Gln Val
            675                 680                 685
```

```
Ser Val Glu Ile Glu Trp Glu Leu Gln Lys Glu Asn Ser Lys Arg Trp
    690                 695                 700
Asn Pro Glu Val Gln Tyr Thr Ser Asn Tyr Asn Lys Ser Val Asn Val
705                 710                 715                 720
Asp Phe Thr Val Asp Thr Asn Gly Val Tyr Ser Glu Pro Arg Pro Ile
                725                 730                 735
Gly Thr Arg Tyr Leu Thr Arg Asn Gln
            740                 745

<210> SEQ ID NO 44
<211> LENGTH: 745
<212> TYPE: PRT
<213> ORGANISM: Artificial Sequence
<220> FEATURE:
<223> OTHER INFORMATION: AAV capsid variant

<400> SEQUENCE: 44

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
    130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
```

```
Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Gly Ile Ser Asp
                580                 585                 590

Gln Thr Lys His Ala Arg Gln Ala Ala Thr Ala Asp Val Asn Thr Gln
            595                 600                 605

Gly Val Leu Pro Gly Met Val Trp Gln Asp Arg Asp Val Tyr Leu Gln
            610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Pro Gln Ile
                645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
            690                 695                 700

Asn Pro Glu Ile Gln Tyr Thr Ser Asn Tyr Asn Lys Ser Val Asn Val
705                 710                 715                 720
```

```
Asp Phe Thr Val Asp Thr Asn Gly Val Tyr Ser Glu Pro Arg Pro Ile
                725                 730                 735
Gly Thr Arg Tyr Leu Thr Arg Asn Leu
            740                 745
```

<210> SEQ ID NO 45
<211> LENGTH: 745
<212> TYPE: PRT
<213> ORGANISM: Artificial Sequence
<220> FEATURE:
<223> OTHER INFORMATION: AAV capsid variant

<400> SEQUENCE: 45

```
Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro
            20                  25                  30
Lys Pro Ala Glu Arg His Lys Asp Asp Ser Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
```

```
Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Gln Ala Asp
            580                 585                 590

Thr Thr Lys Asn Ala Arg Gln Ala Ala Thr Ala Asp Val Asn Thr Gln
        595                 600                 605

Gly Val Leu Pro Gly Met Val Trp Gln Asp Arg Asp Val Tyr Leu Gln
    610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Pro Gln Ile
                645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
        675                 680                 685

Ser Val Glu Ile Glu Trp Glu Leu Gln Lys Glu Asn Ser Lys Arg Trp
    690                 695                 700

Asn Pro Glu Val Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
            740                 745
```

<210> SEQ ID NO 46
<211> LENGTH: 745
<212> TYPE: PRT
<213> ORGANISM: Artificial Sequence
<220> FEATURE:
<223> OTHER INFORMATION: AAV capsid variant

<400> SEQUENCE: 46

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
```

```
                370             375             380
Gln Ala Val Gly Arg Ser Ser Phe Tyr Cys Leu Glu Tyr Phe Pro Ser
385             390             395             400

Gln Met Leu Arg Thr Gly Asn Asn Phe Thr Phe Ser Tyr Thr Phe Glu
                405             410             415

Asp Val Pro Phe His Ser Ser Tyr Ala His Ser Gln Ser Leu Asp Arg
            420             425             430

Leu Met Asn Pro Leu Ile Asp Gln Tyr Leu Tyr Tyr Leu Ser Arg Thr
            435             440             445

Asn Thr Pro Ser Gly Thr Thr Thr Gln Ser Arg Leu Gln Phe Ser Gln
            450             455             460

Ala Gly Ala Ser Asp Ile Arg Asp Gln Ser Arg Asn Trp Leu Pro Gly
465             470             475             480

Pro Cys Tyr Arg Gln Gln Arg Val Ser Lys Thr Ser Ala Asp Asn Asn
                485             490             495

Asn Ser Glu Tyr Ser Trp Thr Gly Ala Thr Lys Tyr His Leu Asn Gly
            500             505             510

Arg Asp Ser Leu Val Asn Pro Gly Pro Ala Met Ala Ser His Lys Asp
            515             520             525

Asp Glu Glu Lys Phe Phe Pro Gln Ser Gly Val Leu Ile Phe Gly Lys
            530             535             540

Gln Gly Ser Glu Lys Thr Asn Val Asp Ile Glu Lys Val Met Ile Thr
545             550             555             560

Asp Glu Glu Glu Ile Arg Thr Thr Asn Pro Val Ala Thr Glu Gln Tyr
                565             570             575

Gly Ser Val Ser Thr Asn Leu Gln Arg Gly Asn Leu Ala His Asp Ile
            580             585             590

Thr Lys Asn Ile Ala Arg Gln Ala Ala Thr Ala Asp Val Asn Thr Gln
            595             600             605

Gly Val Leu Pro Gly Met Val Trp Gln Asp Arg Asp Val Tyr Leu Gln
610             615             620

Gly Pro Ile Trp Ala Lys Ile Pro His Thr Asp Gly His Phe His Pro
625             630             635             640

Ser Pro Leu Met Gly Gly Phe Gly Leu Lys His Pro Pro Gln Ile
                645             650             655

Leu Ile Lys Asn Thr Pro Val Pro Ala Asn Pro Ser Thr Thr Phe Ser
            660             665             670

Ala Ala Lys Phe Ala Ser Phe Ile Thr Gln Tyr Ser Thr Gly Gln Val
            675             680             685

Ser Val Glu Ile Glu Trp Glu Leu Gln Lys Glu Asn Ser Lys Arg Trp
690             695             700

Asn Pro Glu Ile Gln Tyr Thr Ser Asn Tyr Asn Lys Ser Val Asn Val
705             710             715             720

Asp Phe Thr Val Asp Thr Asn Gly Val Tyr Ser Glu Pro Arg Pro Ile
                725             730             735

Gly Thr Arg Tyr Leu Thr Arg Asn Leu
            740             745

<210> SEQ ID NO 47
<211> LENGTH: 745
<212> TYPE: PRT
<213> ORGANISM: Artificial Sequence
<220> FEATURE:
<223> OTHER INFORMATION: AAV capsid variant
```

```
<400> SEQUENCE: 47

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415
```

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Leu Ala Asn Gln Asp
            580                 585                 590

Tyr Thr Lys Thr Ala Arg Gln Ala Ala Thr Ala Asp Val Asn Thr Gln
            595                 600                 605

Gly Val Leu Pro Gly Met Val Trp Gln Asp Arg Asp Val Tyr Leu Gln
            610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
            645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
            690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
            725                 730                 735

Gly Thr Arg Tyr Leu Thr Arg Asn Leu
            740                 745

<210> SEQ ID NO 48
<211> LENGTH: 745
<212> TYPE: PRT
<213> ORGANISM: Artificial Sequence
<220> FEATURE:
<223> OTHER INFORMATION: AAV capsid variant

<400> SEQUENCE: 48

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

```
Lys Pro Ala Glu Arg His Lys Asp Asp Ser Arg Gly Leu Val Leu Pro
         35                  40                  45

Gly Tyr Lys Tyr Leu Gly Pro Phe Asn Gly Leu Asp Lys Gly Glu Pro
 50                  55                  60

Val Asn Glu Ala Asp Ala Ala Leu Glu His Asp Lys Ala Tyr Asp
 65              70              75                  80

Arg Gln Leu Asp Ser Gly Asp Asn Pro Tyr Leu Lys Tyr Asn His Ala
                 85              90                  95

Asp Ala Glu Phe Gln Glu Arg Leu Lys Glu Asp Thr Ser Phe Gly Gly
            100             105             110

Asn Leu Gly Arg Ala Val Phe Gln Ala Lys Lys Arg Val Leu Glu Pro
            115             120             125

Leu Gly Leu Val Glu Glu Pro Val Lys Thr Ala Pro Gly Lys Lys Arg
        130             135             140

Pro Val Glu His Ser Pro Val Glu Pro Asp Ser Ser Ser Gly Thr Gly
145             150             155             160

Lys Ala Gly Gln Gln Pro Ala Arg Lys Arg Leu Asn Phe Gly Gln Thr
                165             170             175

Gly Asp Ala Asp Ser Val Pro Asp Pro Gln Pro Leu Gly Gln Pro Pro
            180             185             190

Ala Ala Pro Ser Gly Leu Gly Thr Asn Thr Met Ala Thr Gly Ser Gly
        195             200             205

Ala Pro Met Ala Asp Asn Asn Glu Gly Ala Asp Gly Val Gly Asn Ser
    210             215             220

Ser Gly Asn Trp His Cys Asp Ser Thr Trp Met Gly Asp Arg Val Ile
225             230             235             240

Thr Thr Ser Thr Arg Thr Trp Ala Leu Pro Thr Tyr Asn Asn His Leu
            245             250             255

Tyr Lys Gln Ile Ser Ser Gln Ser Gly Ala Ser Asn Asp Asn His Tyr
            260             265             270

Phe Gly Tyr Ser Thr Pro Trp Gly Tyr Phe Asp Phe Asn Arg Phe His
        275             280             285

Cys His Phe Ser Pro Arg Asp Trp Gln Arg Leu Ile Asn Asn Asn Trp
    290             295             300

Gly Phe Arg Pro Lys Arg Leu Asn Phe Lys Leu Phe Asn Ile Gln Val
305             310             315             320

Lys Glu Val Thr Gln Asn Asp Gly Thr Thr Thr Ile Ala Asn Asn Leu
            325             330             335

Thr Ser Thr Val Gln Val Phe Thr Asp Ser Glu Tyr Gln Leu Pro Tyr
            340             345             350

Val Leu Gly Ser Ala His Gln Gly Cys Leu Pro Pro Phe Pro Ala Asp
        355             360             365

Val Phe Met Val Pro Gln Tyr Gly Tyr Leu Thr Leu Asn Asn Gly Ser
370             375             380

Gln Ala Val Gly Arg Ser Ser Phe Tyr Cys Leu Glu Tyr Phe Pro Ser
385             390             395             400

Gln Met Leu Arg Thr Gly Asn Asn Phe Thr Phe Ser Tyr Thr Phe Glu
            405             410             415

Asp Val Pro Phe His Ser Ser Tyr Ala His Ser Gln Ser Leu Asp Arg
            420             425             430

Leu Met Asn Pro Leu Ile Asp Gln Tyr Leu Tyr Tyr Leu Ser Arg Thr
        435             440             445
```

```
Asn Thr Pro Ser Gly Thr Thr Thr Gln Ser Arg Leu Gln Phe Ser Gln
    450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
    530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Leu Ala Pro Asn Ser
            580                 585                 590
Thr His Gly Ser Ala Arg Gln Ala Ala Thr Ala Asp Val Asn Thr Gln
        595                 600                 605
Gly Val Leu Pro Gly Met Val Trp Gln Asp Arg Asp Val Tyr Leu Gln
    610                 615                 620
Gly Pro Ile Trp Ala Lys Ile Pro His Thr Asp Gly His Phe His Pro
625                 630                 635                 640
Ser Pro Leu Met Gly Gly Phe Gly Leu Lys His Pro Pro Gln Ile
                645                 650                 655
Leu Ile Lys Asn Thr Pro Val Pro Ala Asn Pro Ser Thr Thr Phe Ser
            660                 665                 670
Ala Ala Lys Phe Ala Ser Phe Ile Thr Gln Tyr Ser Thr Gly Gln Val
        675                 680                 685
Ser Val Glu Ile Glu Trp Glu Leu Gln Lys Glu Asn Ser Lys Arg Trp
    690                 695                 700
Asn Pro Glu Ile Gln Tyr Thr Ser Asn Tyr Asn Lys Ser Val Asn Val
705                 710                 715                 720
Asp Phe Thr Val Asp Thr Asn Gly Val Tyr Ser Glu Pro Arg Pro Ile
                725                 730                 735
Gly Thr Arg Tyr Leu Thr Arg Asn Leu
            740                 745

<210> SEQ ID NO 49
<211> LENGTH: 745
<212> TYPE: PRT
<213> ORGANISM: Artificial Sequence
<220> FEATURE:
<223> OTHER INFORMATION: AAV capsid variant

<400> SEQUENCE: 49

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro
                20                  25                  30
Lys Pro Ala Glu Arg His Lys Asp Asp Ser Arg Gly Leu Val Leu Pro
            35                  40                  45
Gly Tyr Lys Tyr Leu Gly Pro Phe Asn Gly Leu Asp Lys Gly Glu Pro
        50                  55                  60
```

```
Val Asn Glu Ala Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
```

```
                     485                 490                 495
Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Asn Lys Thr
            580                 585                 590

Thr Asn Lys Asp Ala Arg Gln Ala Ala Thr Ala Asp Val Asn Thr Gln
            595                 600                 605

Gly Val Leu Pro Gly Met Val Trp Gln Asp Arg Asp Val Tyr Leu Gln
            610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Pro Gln Ile
                645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
            690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
            740                 745

<210> SEQ ID NO 50
<211> LENGTH: 745
<212> TYPE: PRT
<213> ORGANISM: Artificial Sequence
<220> FEATURE:
<223> OTHER INFORMATION: AAV capsid variant

<400> SEQUENCE: 50

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
```

```
                100                 105                 110
Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
        130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
            165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
            210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525
```

```
Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Thr Asn Arg
            580                 585                 590

Thr Ser Pro Asp Ala Arg Gln Ala Thr Ala Asp Val Asn Thr Gln
            595                 600                 605

Gly Val Leu Pro Gly Met Val Trp Gln Asp Arg Asp Val Tyr Leu Gln
            610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
            645                 650                 655

Leu Ile Lys Asn Thr Pro Val Pro Ala Asn Pro Ser Thr Thr Phe Ser
                660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
            740                 745

<210> SEQ ID NO 51
<211> LENGTH: 745
<212> TYPE: PRT
<213> ORGANISM: Artificial Sequence
<220> FEATURE:
<223> OTHER INFORMATION: AAV capsid variant

<400> SEQUENCE: 51

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140
```

```
Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
        210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560
```

-continued

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Leu Ala Gly Lys Ser
        580                 585                 590

Lys Val Ile Asp Ala Arg Gln Ala Ala Thr Ala Asp Val Asn Thr Gln
            595                 600                 605

Gly Val Leu Pro Gly Met Val Trp Gln Asp Arg Asp Val Tyr Leu Gln
        610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
            645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
        690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
            725                 730                 735

Gly Thr Arg Tyr Leu Thr Arg Asn Leu
            740                 745

<210> SEQ ID NO 52
<211> LENGTH: 745
<212> TYPE: PRT
<213> ORGANISM: Artificial Sequence
<220> FEATURE:
<223> OTHER INFORMATION: AAV capsid variant

<400> SEQUENCE: 52

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

```
Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Ala Ser Asp
            580                 585                 590

Ser Thr Lys Ala Ala Arg Gln Ala Ala Thr Ala Asp Val Asn Thr Gln
```

```
                  595                 600                 605
Gly Val Leu Pro Gly Met Val Trp Gln Asp Arg Asp Val Tyr Leu Gln
    610                 615                 620
Gly Pro Ile Trp Ala Lys Ile Pro His Thr Asp Gly His Phe His Pro
625                 630                 635                 640
Ser Pro Leu Met Gly Phe Gly Leu Lys His Pro Pro Pro Gln Ile
                    645                 650                 655
Leu Ile Lys Asn Thr Pro Val Pro Ala Asn Pro Ser Thr Thr Phe Ser
                660                 665                 670
Ala Ala Lys Phe Ala Ser Phe Ile Thr Gln Tyr Ser Thr Gly Gln Val
                675                 680                 685
Ser Val Glu Ile Glu Trp Glu Leu Gln Lys Glu Asn Ser Lys Arg Trp
            690                 695                 700
Asn Pro Glu Ile Gln Tyr Thr Ser Asn Tyr Asn Lys Ser Val Asn Val
705                 710                 715                 720
Asp Phe Thr Val Asp Thr Asn Gly Val Tyr Ser Glu Pro Arg Pro Ile
                725                 730                 735
Gly Thr Arg Tyr Leu Thr Arg Asn Leu
                740                 745

<210> SEQ ID NO 53
<211> LENGTH: 745
<212> TYPE: PRT
<213> ORGANISM: Artificial Sequence
<220> FEATURE:
<223> OTHER INFORMATION: AAV capsid variant

<400> SEQUENCE: 53

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Leu Glu His Asp Lys Ala Tyr Asp
65              70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
    130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
```

-continued

```
                210                 215                 220
Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
                290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
                370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
                450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
                530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Lys Asp Arg
                580                 585                 590

Ala Pro Ser Thr Ala Arg Gln Ala Ala Thr Ala Asp Val Asn Thr Gln
                595                 600                 605

Gly Val Leu Pro Gly Met Val Trp Gln Asp Arg Asp Val Tyr Leu Gln
                610                 615                 620

Gly Pro Ile Trp Ala Lys Ile Pro His Thr Asp Gly His Phe His Pro
625                 630                 635                 640
```

```
Ser Pro Leu Met Gly Gly Phe Gly Leu Lys His Pro Pro Gln Ile
             645                 650                 655

Leu Ile Lys Asn Thr Pro Val Pro Ala Asn Pro Ser Thr Thr Phe Ser
             660                 665                 670

Ala Ala Lys Phe Ala Ser Phe Ile Thr Gln Tyr Ser Thr Gly Gln Val
             675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
             725                 730                 735

Gly Thr Arg Tyr Leu Thr Arg Asn Leu
             740                 745

<210> SEQ ID NO 54
<211> LENGTH: 745
<212> TYPE: PRT
<213> ORGANISM: Artificial Sequence
<220> FEATURE:
<223> OTHER INFORMATION: AAV capsid variant

<400> SEQUENCE: 54

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
             20                  25                  30

Lys Pro Ala Glu Arg His Lys Asp Asp Ser Arg Gly Leu Val Leu Pro
             35                  40                  45

Gly Tyr Lys Tyr Leu Gly Pro Phe Asn Gly Leu Asp Lys Gly Glu Pro
50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
             85                  90                  95

Asp Ala Glu Phe Gln Glu Arg Leu Lys Glu Asp Thr Ser Phe Gly Gly
             100                 105                 110

Asn Leu Gly Arg Ala Val Phe Gln Ala Lys Lys Arg Val Leu Glu Pro
             115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
             165                 170                 175

Gly Asp Ala Asp Ser Val Pro Asp Pro Gln Pro Leu Gly Gln Pro Pro
             180                 185                 190

Ala Ala Pro Ser Gly Leu Gly Thr Asn Thr Met Ala Thr Gly Ser Gly
             195                 200                 205

Ala Pro Met Ala Asp Asn Asn Glu Gly Ala Asp Gly Val Gly Asn Ser
             210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
             245                 250                 255
```

-continued

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Leu Ala His Gln Asp
            580                 585                 590

Thr Thr Lys Asn Ala Arg Gln Ala Ala Thr Ala Asp Val Asn Thr Gln
            595                 600                 605

Gly Val Leu Pro Gly Met Val Trp Gln Asp Arg Asp Val Tyr Leu Gln
            610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Pro Gln Ile
            645                 650                 655

Leu Ile Lys Asn Thr Pro Val Pro Ala Asn Pro Ser Thr Thr Phe Ser
            660                 665                 670

```
Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
            725                 730                 735

Gly Thr Arg Tyr Leu Thr Arg Asn Leu
            740                 745

<210> SEQ ID NO 55
<211> LENGTH: 745
<212> TYPE: PRT
<213> ORGANISM: Artificial Sequence
<220> FEATURE:
<223> OTHER INFORMATION: AAV capsid variant

<400> SEQUENCE: 55

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285
```

```
Cys His Phe Ser Pro Arg Asp Trp Gln Arg Leu Ile Asn Asn Asn Trp
    290             295                 300
Gly Phe Arg Pro Lys Arg Leu Asn Phe Lys Leu Phe Asn Ile Gln Val
305             310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
370                 375                 380
Gln Ala Val Gly Arg Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
Asn Thr Pro Ser Gly Thr Thr Thr Gln Ser Arg Leu Gln Phe Ser Gln
450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Leu Pro Ile Ser Asn
            580                 585                 590
Glu Asn Glu His Ala Arg Gln Ala Ala Thr Ala Asp Val Asn Thr Gln
        595                 600                 605
Gly Val Leu Pro Gly Met Val Trp Gln Asp Arg Asp Val Tyr Leu Gln
610                 615                 620
Gly Pro Ile Trp Ala Lys Ile Pro His Thr Asp Gly His Phe His Pro
625                 630                 635                 640
Ser Pro Leu Met Gly Gly Phe Gly Leu Lys His Pro Pro Pro Gln Ile
                645                 650                 655
Leu Ile Lys Asn Thr Pro Val Pro Ala Asn Pro Ser Thr Thr Phe Ser
            660                 665                 670
Ala Ala Lys Phe Ala Ser Phe Ile Thr Gln Tyr Ser Thr Gly Gln Val
        675                 680                 685
Ser Val Glu Ile Glu Trp Glu Leu Gln Lys Glu Asn Ser Lys Arg Trp
690                 695                 700
Asn Pro Glu Ile Gln Tyr Thr Ser Asn Tyr Asn Lys Ser Val Asn Val
```

-continued

```
                705                 710                 715                 720
Asp Phe Thr Val Asp Thr Asn Gly Val Tyr Ser Glu Pro Arg Pro Ile
                    725                 730                 735

Gly Thr Arg Tyr Leu Thr Arg Asn Leu
                740                 745

<210> SEQ ID NO 56
<211> LENGTH: 745
<212> TYPE: PRT
<213> ORGANISM: Artificial Sequence
<220> FEATURE:
<223> OTHER INFORMATION: AAV capsid variant

<400> SEQUENCE: 56

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
```

```
                    325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
                355                 360                 365
Val Phe Met Val Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Arg Thr
                435                 440                 445
Asn Thr Pro Ser Gly Thr Thr Thr Gln Ser Arg Leu Gln Phe Ser Gln
                450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
                515                 520                 525
Asp Glu Glu Lys Phe Phe Pro Gln Ser Gly Val Leu Ile Phe Gly Lys
                530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Leu Pro Gln Ala Asn
                580                 585                 590
Ala Asn Glu Asn Ala Arg Gln Ala Ala Thr Ala Asp Val Asn Thr Gln
                595                 600                 605
Gly Val Leu Pro Gly Met Val Trp Gln Asp Arg Asp Val Tyr Leu Gln
                610                 615                 620
Gly Pro Ile Trp Ala Lys Ile Pro His Thr Asp Gly His Phe His Pro
625                 630                 635                 640
Ser Pro Leu Met Gly Gly Phe Gly Leu Lys His Pro Pro Pro Gln Ile
                645                 650                 655
Leu Ile Lys Asn Thr Pro Val Pro Ala Asn Pro Ser Thr Thr Phe Ser
                660                 665                 670
Ala Ala Lys Phe Ala Ser Phe Ile Thr Gln Tyr Ser Thr Gly Gln Val
                675                 680                 685
Ser Val Glu Ile Glu Trp Glu Leu Gln Lys Glu Asn Ser Lys Arg Trp
                690                 695                 700
Asn Pro Glu Ile Gln Tyr Thr Ser Asn Tyr Asn Lys Ser Val Asn Val
705                 710                 715                 720
Asp Phe Thr Val Asp Thr Asn Gly Val Tyr Ser Glu Pro Arg Pro Ile
                725                 730                 735
Gly Thr Arg Tyr Leu Thr Arg Asn Leu
                740                 745
```

<210> SEQ ID NO 57
<211> LENGTH: 745
<212> TYPE: PRT
<213> ORGANISM: Artificial Sequence
<220> FEATURE:
<223> OTHER INFORMATION: AAV capsid variant

<400> SEQUENCE: 57

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp Arg
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365
```

```
Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala His Pro Asp
                580                 585                 590

Thr Thr Lys Asn Ala Arg Gln Ala Ala Thr Ala Asp Val Asn Thr Gln
            595                 600                 605

Gly Val Leu Pro Gly Met Val Trp Gln Asp Arg Asp Val Tyr Leu Gln
            610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Gln Ile
                645                 650                 655

Leu Ile Lys Asn Thr Pro Val Pro Ala Asn Pro Ser Thr Thr Phe Ser
                660                 665                 670

Ala Ala Lys Phe Ala Ser Phe Ile Thr Gln Tyr Ser Thr Gly Gln Val
            675                 680                 685

Ser Val Glu Ile Glu Trp Glu Leu Gln Lys Glu Asn Ser Lys Arg Trp
690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
                740                 745

<210> SEQ ID NO 58
<211> LENGTH: 737
<212> TYPE: PRT
<213> ORGANISM: Artificial Sequence
<220> FEATURE:
```

```
<223> OTHER INFORMATION: Ancestral capsid protein
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (268)..(268)
<223> OTHER INFORMATION: Xaa can be any naturally occurring amino acid
<220> FEATURE:
<221> NAME/KEY: misc_feature
<222> LOCATION: (448)..(448)
<223> OTHER INFORMATION: Xaa can be any naturally occurring amino acid
<220> FEATURE:
<221> NAME/KEY: misc_feature
<222> LOCATION: (459)..(460)
<223> OTHER INFORMATION: Xaa can be any naturally occurring amino acid
<220> FEATURE:
<221> NAME/KEY: misc_feature
<222> LOCATION: (467)..(467)
<223> OTHER INFORMATION: Xaa can be any naturally occurring amino acid
<220> FEATURE:
<221> NAME/KEY: misc_feature
<222> LOCATION: (470)..(471)
<223> OTHER INFORMATION: Xaa can be any naturally occurring amino acid
<220> FEATURE:
<221> NAME/KEY: misc_feature
<222> LOCATION: (474)..(474)
<223> OTHER INFORMATION: Xaa can be any naturally occurring amino acid
<220> FEATURE:
<221> NAME/KEY: misc_feature
<222> LOCATION: (495)..(495)
<223> OTHER INFORMATION: Xaa can be any naturally occurring amino acid
<220> FEATURE:
<221> NAME/KEY: misc_feature
<222> LOCATION: (516)..(516)
<223> OTHER INFORMATION: Xaa can be any naturally occurring amino acid
<220> FEATURE:
<221> NAME/KEY: misc_feature
<222> LOCATION: (533)..(533)
<223> OTHER INFORMATION: Xaa can be any naturally occurring amino acid
<220> FEATURE:
<221> NAME/KEY: misc_feature
<222> LOCATION: (547)..(547)
<223> OTHER INFORMATION: Xaa can be any naturally occurring amino acid
<220> FEATURE:
<221> NAME/KEY: misc_feature
<222> LOCATION: (551)..(551)
<223> OTHER INFORMATION: Xaa can be any naturally occurring amino acid
<220> FEATURE:
<221> NAME/KEY: misc_feature
<222> LOCATION: (555)..(555)
<223> OTHER INFORMATION: Xaa can be any naturally occurring amino acid
<220> FEATURE:
<221> NAME/KEY: misc_feature
<222> LOCATION: (557)..(557)
<223> OTHER INFORMATION: Xaa can be any naturally occurring amino acid
<220> FEATURE:
<221> NAME/KEY: misc_feature
<222> LOCATION: (561)..(561)
<223> OTHER INFORMATION: Xaa can be any naturally occurring amino acid
<220> FEATURE:
<221> NAME/KEY: misc_feature
<222> LOCATION: (563)..(563)
<223> OTHER INFORMATION: Xaa can be any naturally occurring amino acid
<220> FEATURE:
<221> NAME/KEY: misc_feature
<222> LOCATION: (577)..(577)
<223> OTHER INFORMATION: Xaa can be any naturally occurring amino acid
<220> FEATURE:
<221> NAME/KEY: misc_feature
<222> LOCATION: (583)..(583)
<223> OTHER INFORMATION: Xaa can be any naturally occurring amino acid
<220> FEATURE:
<221> NAME/KEY: misc_feature
```

```
<222> LOCATION: (593)..(593)
<223> OTHER INFORMATION: Xaa can be any naturally occurring amino acid
<220> FEATURE:
<221> NAME/KEY: misc_feature
<222> LOCATION: (596)..(596)
<223> OTHER INFORMATION: Xaa can be any naturally occurring amino acid
<220> FEATURE:
<221> NAME/KEY: misc_feature
<222> LOCATION: (661)..(662)
<223> OTHER INFORMATION: Xaa can be any naturally occurring amino acid
<220> FEATURE:
<221> NAME/KEY: misc_feature
<222> LOCATION: (664)..(665)
<223> OTHER INFORMATION: Xaa can be any naturally occurring amino acid
<220> FEATURE:
<221> NAME/KEY: misc_feature
<222> LOCATION: (710)..(710)
<223> OTHER INFORMATION: Xaa can be any naturally occurring amino acid
<220> FEATURE:
<221> NAME/KEY: misc_feature
<222> LOCATION: (717)..(719)
<223> OTHER INFORMATION: Xaa can be any naturally occurring amino acid
<220> FEATURE:
<221> NAME/KEY: misc_feature
<222> LOCATION: (723)..(723)
<223> OTHER INFORMATION: Xaa can be any naturally occurring amino acid

<400> SEQUENCE: 58

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Xaa Ser Xaa Gly Xaa Thr Asn Asp Asn
            260                 265                 270
```

```
His Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Xaa
            435                 440                 445

Arg Thr Gln Ser Thr Gly Gly Thr Ala Gly Xaa Xaa Glu Leu Leu Phe
            450                 455                 460

Ser Gln Xaa Gly Pro Xaa Xaa Met Ser Xaa Gln Ala Lys Asn Trp Leu
465                 470                 475                 480

Pro Gly Pro Cys Tyr Arg Gln Gln Arg Val Ser Lys Thr Leu Xaa Gln
                485                 490                 495

Asn Asn Asn Ser Asn Phe Ala Trp Thr Gly Ala Thr Lys Tyr His Leu
            500                 505                 510

Asn Gly Arg Xaa Ser Leu Val Asn Pro Gly Val Ala Met Ala Thr His
            515                 520                 525

Lys Asp Asp Glu Xaa Arg Phe Phe Pro Ser Ser Gly Val Leu Ile Phe
530                 535                 540

Gly Lys Xaa Gly Ala Gly Xaa Asn Asn Thr Xaa Leu Xaa Asn Val Met
545                 550                 555                 560

Xaa Thr Xaa Glu Glu Glu Ile Lys Thr Thr Asn Pro Val Ala Thr Glu
                565                 570                 575

Xaa Tyr Gly Val Val Ala Xaa Asn Leu Gln Ser Ser Asn Thr Ala Pro
            580                 585                 590

Xaa Thr Gly Xaa Val Asn Ser Gln Gly Ala Leu Pro Gly Met Val Trp
            595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
            625                 630                 635                 640

Leu Lys His Pro Pro Pro Gln Ile Leu Ile Lys Asn Thr Pro Val Pro
            645                 650                 655

Ala Asn Pro Pro Xaa Xaa Phe Xaa Xaa Ala Lys Phe Ala Ser Phe Ile
                660                 665                 670

Thr Gln Tyr Ser Thr Gly Gln Val Ser Val Glu Ile Glu Trp Glu Leu
            675                 680                 685
```

```
Gln Lys Glu Asn Ser Lys Arg Trp Asn Pro Glu Ile Gln Tyr Thr Ser
    690                 695                 700

Asn Tyr Ala Lys Ser Xaa Asn Val Asp Phe Ala Val Xaa Xaa Xaa Gly
705                 710                 715                 720

Val Tyr Xaa Glu Pro Arg Pro Ile Gly Thr Arg Tyr Leu Thr Arg Asn
            725                 730                 735

Leu

<210> SEQ ID NO 59
<211> LENGTH: 737
<212> TYPE: PRT
<213> ORGANISM: Artificial Sequence
<220> FEATURE:
<223> OTHER INFORMATION: Ancestral variant capsid

<400> SEQUENCE: 59

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Ala Gly Ser Thr Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
```

```
                305                 310                 315                 320
Gln Val Lys Glu Val Thr Thr Asn Asp Gly Val Thr Thr Ile Ala Asn
                    325                 330                 335

Asn Leu Thr Ser Thr Val Gln Val Phe Ser Asp Ser Glu Tyr Gln Leu
                340                 345                 350

Pro Tyr Val Leu Gly Ser Ala His Gln Gly Cys Leu Pro Phe Pro
            355                 360                 365

Ala Asp Val Phe Met Ile Pro Gln Tyr Gly Tyr Leu Thr Leu Asn Asn
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ala
                435                 440                 445

Arg Thr Gln Ser Thr Gly Gly Thr Ala Gly Thr Arg Glu Leu Leu Phe
            450                 455                 460

Ser Gln Ala Gly Pro Ser Asn Met Ser Ala Gln Ala Lys Asn Trp Leu
465                 470                 475                 480

Pro Gly Pro Cys Tyr Arg Gln Gln Arg Val Ser Lys Thr Leu Ser Gln
                485                 490                 495

Asn Asn Asn Ser Asn Phe Ala Trp Thr Gly Ala Thr Lys Tyr His Leu
                500                 505                 510

Asn Gly Arg Asp Ser Leu Val Asn Pro Gly Val Ala Met Ala Thr His
            515                 520                 525

Lys Asp Asp Glu Asp Arg Phe Phe Pro Ser Ser Gly Val Leu Ile Phe
            530                 535                 540

Gly Lys Gln Gly Ala Gly Ala Asn Asn Thr Ala Leu Glu Asn Val Met
545                 550                 555                 560

Met Thr Ser Glu Glu Glu Ile Lys Thr Thr Asn Pro Val Ala Thr Glu
                565                 570                 575

Gln Tyr Gly Val Val Ala Ser Asn Leu Gln Ser Ser Asn Thr Ala Pro
            580                 585                 590

Val Thr Gly Thr Val Asn Ser Gln Gly Ala Leu Pro Gly Met Val Trp
            595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Ala Val Phe Thr Pro Ala Lys Phe Ala Ser Phe Ile
                660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
            690                 695                 700

Asn Tyr Ala Lys Ser Thr Asn Val Asp Phe Ala Val Asp Asn Glu Gly
705                 710                 715                 720

Val Tyr Ser Glu Pro Arg Pro Ile Gly Thr Arg Tyr Leu Thr Arg Asn
                725                 730                 735
```

Leu

<210> SEQ ID NO 60
<211> LENGTH: 10
<212> TYPE: PRT
<213> ORGANISM: Artificial Sequence
<220> FEATURE:
<223> OTHER INFORMATION: Heterologous peptide insertion

<400> SEQUENCE: 60

Ile Ala His Asp Ile Thr Lys Asn Ile Ala
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Heterologous peptide insertion

<400> SEQUENCE: 61

Asp Ile Thr Lys Asn Ile Ala
1               5

<210> SEQ ID NO 62
<211> LENGTH: 8
<212> TYPE: PRT
<213> ORGANISM: Artificial Sequence
<220> FEATURE:
<223> OTHER INFORMATION: Heterologous peptide insertion

<400> SEQUENCE: 62

Asn Lys Thr Thr Asn Lys Asp Ala
1               5

<210> SEQ ID NO 63
<211> LENGTH: 8
<212> TYPE: PRT
<213> ORGANISM: Artificial Sequence
<220> FEATURE:
<223> OTHER INFORMATION: Heterologous peptide insertion

<400> SEQUENCE: 63

Pro Gln Ala Asn Ala Asn Glu Asn
1               5

<210> SEQ ID NO 64
<211> LENGTH: 8
<212> TYPE: PRT
<213> ORGANISM: Artificial Sequence
<220> FEATURE:
<223> OTHER INFORMATION: Heterologous peptide insertion

<400> SEQUENCE: 64

Pro Ile Ser Asn Glu Asn Glu His
1               5

METHOD OF USING ADENO-ASSOCIATED VIRUS WITH VARIANT CAPSID

This application is a divisional of U.S. patent application Ser. No. 16/300,446 filed Nov. 8, 2018 which pursuant to 35 U.S.C. § 119(e), claims priority to the filing date of U.S. Provisional Patent Application Ser. No. 62/336,441 filed May 13, 2016; U.S. Provisional Patent Application Ser. No. 62/378,106 filed Aug. 22, 2016; U.S. Provisional Patent Application Ser. No. 62/384,590 filed Sep. 7, 2016; U.S. Provisional Patent Application Ser. No. 62/454,612 filed Feb. 3, 2017; the full disclosures of which are herein incorporated by reference.

INCORPORATION BY REFERENCE OF A SEQUENCE LISTING PROVIDED AS A TEXT FILE

A Sequence Listing is provided herewith as a text file, "4D_ST25.txt." created on May 12, 2017 and having a size of 198 KB. The contents of the text file are incorporated by reference herein in their entirety.

FIELD OF THE INVENTION

The invention disclosed herein relates generally to the field of adeno-associated virus (AAV) virions comprising variant capsid proteins and the generation of such variant capsids using directed evolution techniques.

BACKGROUND OF THE DISCLOSURE

Inherited retinal diseases encompass a large group of heterogenous genetic diseases that affect approximately 1 in 3000 people (greater than 2 million people worldwide) and are a major source of severe vision loss or blindness. Complex, multifactoral retinal diseases such as wet age related macular degeneration (wAMD) and diabetic retinopathy (DR) impact even more individuals, with 1.7 million Americans currently living with severe central vision loss associated with wAMD and almost one-third of adults over age 40 years with diabetes being visually impaired. These diseases are typically associated with the dysfunction or death of one or more types of cell of the retina, in some instances due to the absence of expression or function of a key protein, e.g. RPE65 in LCA2, in other instances due to gene mutations that create toxic gene products, e.g dominant mutations that affect rhodopsin protein folding, or in yet other instances due to changes in retinal physiology induced by the ectopic expression of a protein, e.g. VEGF in wAMD.

One approach to addressing this great unmedical need is gene-based adeno-associated virus (AAV)-mediated therapy, in which a recombinant adeno associated virus (rAAV) is used to deliver a gene to one or more types of cells in the retina, for example to replace a missing gene, to correct a dominant defective gene, or to provide a template for continuous protein therapy. While AAV-based clinical gene therapy has been increasingly successful, it is still fraught with shortcomings with regard to viral vector properties, including, for example, targeting the desired cells of the retina with high efficiency. For example, multiple homologous primate AAV serotypes and numerous nonhuman primate serotypes have been identified and characterized, with AAV2 being the best characterized among the AAV serotypes and the first to be adapted as a gene delivery vehicle in the eye. However, these AAVs (including AAV2) have not been reported to be effective at transducing the deeper cell types of the retina when delivered via intravitreal administration. Accordingly, there is a need in the art for new AAV variants with superior transduction capabilities that will provide for more effective gene-based delivery to the cells of the retina for the treatment of ocular disease. There is a need in the art for such AAV variants which exhibit an enhanced retinal transduction profile—in some instances broadly, in other instances preferentially to certain retinal cell types—as compared to wild-type AAVs and AAV variants as known in the art.

Naturally occurring AAV is a single stranded DNA virus that contains three open reading frames, rep, cap, and aap. The first gene, rep, encodes four proteins necessary for genome replication (Rep78, Rep68, Rep52, and Rep40), the second, cap, expresses three structural proteins (VP1-3) that assemble to form the viral capsid, and the third expresses the assembly activating protein (AAP) that is essential for capsid assembly. AAV is dependent upon the presence of a helper virus, such as an adenovirus or herpesvirus, for active replication. In the absence of a helper virus, AAV establishes a latent state in which its genome is maintained episomally or integrated into the host chromosome in the AAVS1 locus.

In vitro and in vivo-directed evolution techniques may be used to select for AAV variants that offer an improvement over current AAV-based gene delivery vectors. Such directed evolution techniques are known in the art and described, e.g., in PCT publication WO 2014/194132 and Kotterman & Schaffer (Nature Review Genetics, AOP, published online 20 May 2014; doi: 10.1038/nrg3742), both of which are incorporated herein in their entirety by reference. Directed evolution is a capsid engineering approach that emulates natural evolution through iterative rounds of genetic diversification and selection processes, thereby enabling the accumulation of beneficial mutations that progressively improve the function of a biomolecule such as an AAV-based virion. In this approach, wild-type AAV cap genes are diversified to create large genetic libraries that are packaged to generate libraries of viral particles, and selective pressure is applied to isolate unique variants with superior phenotypes that can overcome gene delivery barriers.

AAV variants have been disclosed in, for example, in U.S. Pat. Nos. 9,193,956; 9,186,419; 8,632,764; 8,663,624; 8,927,514; 8,628,966; 8,263,396; 8,734,809; 8,889,641; 8,632,764; 8,691,948; 8,299,295; 8,802,440; 8,445,267; 8,906,307; 8,574,583; 8,067,015; 7,588,772; 7,867,484; 8,163,543; 8,283,151; 8,999,678; 7,892,809; 7,906,111; 7,259,151; 7,629,322; 7,220,577; 8,802,080; 7,198,951; 8,318,480; 8,962,332; 7,790,449; 7,282,199; 8,906,675; 8,524,446; 7,712,893; 6,491,907; 8,637,255; 7,186,522; 7,105,345; 6,759,237; 6,984,517; 6,962,815; 7,749,492; 7,259,151; and 6,156,303; United States Publication Numbers 2013/0295614; 2015/0065562; 2014/0364338; 2013/0323226; 2014/0359799; 2013/0059732; 2014/0037585; 2014/0056854; 2013/0296409; 2014/0335054; 2013/0195801; 2012/0070899; 2011/0275529; 2011/0171262; 2009/0215879; 2010/0297177; 2010/0203083; 2009/0317417; 2009/0202490; 2012/0220492; 2006/0292117; and 2004/0002159; European Publication Numbers 2692731 A1; 2383346 B1; 2359865 B1; 2359866 B1; 2359867 B1; and 2357010 B1; 1791858 B1; 1668143 B1; 1660678 B1; 1664314 B1; 1496944 B1; 1456383 B1; 2341068 B1; 2338900 B1; 1456419 B1; 1310571 B1; 1456383 B1; 1633772 B1; and 1135468 B1; and International (PCT) Publication Numbers WO 2014/124282; WO 2013/170078; WO 2014/160092; WO 2014/103957; WO 2014/052789; WO 2013/174760; WO 2013/123503; WO 2011/038187; and WO 2008/124015; WO 2003/054197; however, none of these references disclose the embodiments and/or features and/or composition of matter structures of the AAV variants disclosed herein.

All documents and references cited herein and in the referenced patent documents, are hereby incorporated herein by reference.

SUMMARY OF THE INVENTION

Provided herein are variant adeno-associated virus (AAV) capsid proteins having one or more modifications in amino acid sequence relative to a parental AAV capsid protein, which, when present in an AAV virion, confer increased infectivity of one or more types of retinal cells as compared to the infectivity of the retinal cells by an AAV virion comprising an unmodified parental AAV capsid protein. Also provided are recombinant AAV virions and pharmaceutical compositions thereof comprising a variant AAV capsid protein as described herein, methods of making variant rAAV capsid proteins and virions, and methods for using these rAAV capsid proteins and virions in research and in clinical practice, for example in the delivery of nucleic acid sequences to one or more cells of the retina for the treatment of retinal disorders and diseases.

In some aspects of the disclosure, variant adeno-associated virus (AAV) capsid proteins are provided, these variant AAV capsid proteins having one or more modifications in amino acid sequence relative to a parental AAV capsid, which, when present in an AAV virion, confer increased infectivity of one or more types of retinal cells (e.g. a photoreceptor cell (e.g. rods; cones), a retinal ganglion cell (RGC), a glial cell (e.g. a Müller glial cell, a microglial cell), a bipolar cell, an amacrine cell, a horizontal cell, and/or a retinal pigmented epithelium (RPE) cell) as compared to the infectivity of the retinal cells by an AAV virion comprising a parental AAV capsid protein that does not comprise the amino acid sequence modification.

In some aspects of the disclosure, recombinant AAV (rAAV) virions are provided, these rAAV virions comprising a variant capsid protein as described herein, wherein the rAAV virions exhibit increased infectivity of one or more types of retinal cells (e.g. a photoreceptor cell (e.g. rods; cones), a retinal ganglion cell (RGC), a glial cell (e.g. a Müller glial cell, a microglial cell), a bipolar cell, an amacrine cell, a horizontal cell, and/or a retinal pigmented epithelium (RPE) cell) relative to the infectivity of the retinal cell by an AAV virion comprising a corresponding unmodified parental AAV capsid protein. In some embodiments, the rAAV virion exhibits increased infectivity of all retinal cells relative to the AAV virion comprising the parental AAV capsid protein. In other embodiments, the rAAV virion exhibits increased infectivity of certain cell types of the retina but not others relative of the AAV virion comprising the parental AAV capsid protein. Put another way, the rAAV virion exhibits increased infectivity that is preferential for certain cell types of the retina but not others, e.g. the rAAV demonstrates a preferentially increased infectivity of one or more cell types selected from photoreceptor cells, retinal ganglion cells, glial cells, bipolar cells, amacrine cells horizontal cell, and/or retinal pigmented epithelium (RPE) cell, but does not demonstrate increased infectivity of all cell types.

In some embodiments, the rAAV virion comprises a heterologous nucleic acid. In some such embodiments, the heterologous nucleic acid encodes an RNA that encodes a polypeptide. In other such embodiments, the heterologous nucleic acid sequence encodes an RNA that does not encode a polypeptide, e.g. the heterologous nucleic acid sequence an RNA interference agent, a guide RNA for a nuclease, etc.

Also provided herein are pharmaceutical compositions comprising the subject infectious rAAV virions and a pharmaceutically acceptable carrier.

Also provided is the use of an rAAV virion comprising a variant capsid protein as herein described in a method of delivering a heterologous nucleic acid to a target cell (such as a retinal cell) by contacting the target cell with the rAAV virion. In some embodiments, the target cell is in vivo, such as in the eye of an individual in need of treatment for an ocular disease. In other embodiments, the target cell is in vitro.

Also provided are methods of treating an ocular disease by administering to a subject in need of such treatment an effective amount of rAAV virions comprising a variant capsid protein as herein described or a pharmaceutical composition comprising an effective amount of the rAAV virions.

Also provided is an isolated nucleic acid comprising a sequence encoding a variant AAV capsid protein as described herein and a host cell comprising the isolated nucleic acid. In yet other embodiments, the isolated nucleic acid and/or isolated host cell comprises the rAAV.

In some aspects, the variant AAV capsid protein comprises an insertion of from about 5 amino acids to about 20 amino acids (a "heterologous peptide", or "peptide insertion") in the GH-loop of the capsid protein, relative to a corresponding parental AAV capsid protein, wherein the variant capsid protein, when present in an AAV virion, confers increased infectivity of a retinal cell compared to the infectivity of a retinal cell by an AAV virion comprising the corresponding parental AAV capsid protein. In some embodiments, the peptide comprises the sequence selected from the group consisting of QADTTKN (SEQ ID NO:13), ISDQTKH (SEQ ID NO:14), ASDSTKA (SEQ ID NO:15), NQDYTKT (SEQ ID NO:16), HDITKNI (SEQ ID NO:17), HPDTTKN (SEQ ID NO:18), HQDTTKN (SEQ ID NO:19), NKTTNKD (SEQ ID NO:20), ISNENEH (SEQ ID NO:21), QANANEN (SEQ ID NO:22), GKSKVID (SEQ ID NO:23), TNRTSPD (SEQ ID NO:24), PNSTHGS (SEQ ID NO:25), KDRAPST (SEQ ID NO:26), LAQADTTKNA (SEQ ID NO:27), LAISDQTKHA (SEQ ID NO:28), LGISDQTKHA (SEQ ID NO:29), LAASDSTKAA (SEQ ID NO:30), LANQDYTKTA (SEQ ID NO:31), LAHDITKNIA (SEQ ID NO:32), LAHPDTTKNA (SEQ ID NO:33), LAHQDTTKNA (SEQ ID NO:34), LANKTTNKDA (SEQ ID NO:35), LPISNENEHA (SEQ ID NO:36), LPQANANENA (SEQ ID NO:37), LAGKSKVIDA (SEQ ID NO:38), LATNRTSPDA (SEQ ID NO:39), LAPNSTHGSA (SEQ ID NO:40) and LAKDRAPSTA (SEQ ID NO:41). In some embodiments, the peptide consists essentially of the sequence selected from the group consisting of QADTTKN (SEQ ID NO:13), ISDQTKH (SEQ ID NO:14), ASDSTKA (SEQ ID NO:15), NQDYTKT (SEQ ID NO:16), HDITKNI (SEQ ID NO:17), HPDTTKN (SEQ ID NO:18), HQDTTKN (SEQ ID NO:19), NKTTNKD (SEQ ID NO:20), ISNENEH (SEQ ID NO:21), QANANEN (SEQ ID NO:22), GKSKVID (SEQ ID NO:23), TNRTSPD (SEQ ID NO:24), PNSTHGS (SEQ ID NO:25), KDRAPST (SEQ ID NO:26), LAQADTTKNA (SEQ ID NO:27), LAISDQTKHA (SEQ ID NO:28), LGISDQTKHA (SEQ ID NO:29), LAASDSTKAA (SEQ ID NO:30), LANQDYTKTA (SEQ ID NO:31), LAHDITKNIA (SEQ ID NO:32), LAHPDTTKNA (SEQ ID NO:33), LAHQDTTKNA (SEQ ID NO:34), LANKTTNKDA (SEQ ID NO:35), LPISNENEHA (SEQ ID NO:36), LPQANANENA (SEQ ID NO:37), LAGKSKVIDA (SEQ ID NO:38), LATNRTSPDA (SEQ ID NO:39), LAPNSTHGSA (SEQ ID NO:40) and LAKDRAPSTA (SEQ ID NO:41). In some aspects, the variant AAV capsid protein comprises one or more amino acid substitutions relative to a corresponding parental AAV capsid protein, wherein the variant capsid protein, when present in an AAV virion, confers increased infectivity of a retinal cell compared to the infectivity of a retinal cell by an AAV virion comprising the corresponding parental AAV capsid protein.

In related aspects, the variant AAV capsid protein comprises a peptide insertion and one or more amino acid substitutions relative to a corresponding parental AAV capsid protein, wherein the variant capsid protein, when present in an AAV virion, confers increased infectivity of a retinal cell compared to the infectivity of a retinal cell by an AAV virion comprising the corresponding parental AAV capsid protein.

Also disclosed herein is a variant AAV capsid protein comprising the heterologous peptide LAISDQTKHA (SEQ ID NO:28) and a P34A substitution relative to AAV2.

Also disclosed herein is a variant AAV capsid protein comprising the heterologous peptide LAISDQTKHA (SEQ ID NO:28) and amino acid substitutions N312K, N449D, N551S, I698V, and L735Q relative to AAV2.

Also disclosed herein are methods for manufacture and/or delivery of an rAAV comprising a variant AAV capsid as disclosed herein. In addition, provided herein are kits comprising an rAAV comprising a variant AAV capsid as disclosed herein and for use in methods described herein.

In other embodiments, the AAV virion comprising the variant capsid protein in the preceding paragraphs may incorporate any of the preceding or subsequently disclosed embodiments. Indeed, it is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the invention and am disclosed herein just as if each and every combination was individually and explicitly disclosed. In addition, all sub-combinations of the various embodiments and elements thereof are also specifically embraced by the invention and are disclosed herein just as if each and every such sub-combination was individually and explicitly disclosed herein.

The Summary of the Invention is not intended to define the claims nor is it intended to limit the scope of the invention in any manner.

Other features and advantages of the invention disclosed herein will be apparent from the following Figures, Detailed Description, and the Claims.

BRIEF DESCRIPTION OF THE FIGURES

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 4A-4D shows frequency of motifs within sequencing analysis. FIG. 4A provides Round 3 sequencing analysis. FIG. 4B provides Round 4 sequencing analysis. FIG. 4C provides Round 5 sequencing analysis. FIG. 4D provides Round 6 sequencing analysis.

FIGS. 10A-10E provide the results of immunohistochemical analysis of the retina of a monkey injected intravitreally with $1\times10^{12}$ vg of the novel AAV variant LAISDQTKHA+P34A delivering a GFP transgene under the control of the CAG promoter, analyzed three weeks after injection. All immunohistochemistry is provided alongside the corresponding fundus fluorescence image, with a red box to denote approximately where in the retina the analysis was performed. FIG. 10A: Robust retinal pigment epithelium (RPE) and photoreceptor transduction was observed using a GFP-specific antibody (red). Cone photoreceptor immunostaining using an M/L opsin antibody is shown in white. FIGS. 10B and 10C: Robust rod and cone photoreceptor (FIG. 10B) and RPE (FIG. 10C) transduction was observed by direct EGFP fluorescence (green) and by immunohistochemistry using a GFP-specific antibody (red). Melanosomes in RPE appear black in the image. FIG. 10D: Transduction of cone photoreceptors (identified by M/L opsin, white) and retinal ganglion cells (RGC) in and around the fovea was observed by direct EGFP fluorescence (green) and by immunohistochemistry using a GFP-specific antibody (red). Images in the middle panels are a higher magnification (63×) of the area denoted by a white box in the left panel. FIG. 10E: Transduction of retinal ganglion cells (RGC) and the retinal ganglion cell layer was observed by direct EGFP fluorescence (right panels, green; lower right panel is a 63× magnification of the upper right panel); top left panel shows the region under brightfield illumination.

FIGS. 11A and 11B: Immunofluorescence imaging of the cell cultures 7 days after infection at an MOI of 500 demonstrates that the novel AAV variant capsid (left panels) transduces RPE cells better than wild type AAV2 capsid (right panels). FIGS. 11C and 11D: Quantification of the percent of GFP-positive RPE cells in each culture by flow cytometry reveals that the novel AAV variant capsid provides for a significant, dose-dependent improvement in the number of cells transduced over wild type AAV2 capsid regardless of cell source. FIGS. 11E and 11F: Quantification of the amount of GFP in each culture by Western blot reveals that the novel AAV variant provides for significant improvement in expression of the transgene over wild type capsid regardless of cell source.

DETAILED DESCRIPTION

Figure 1:
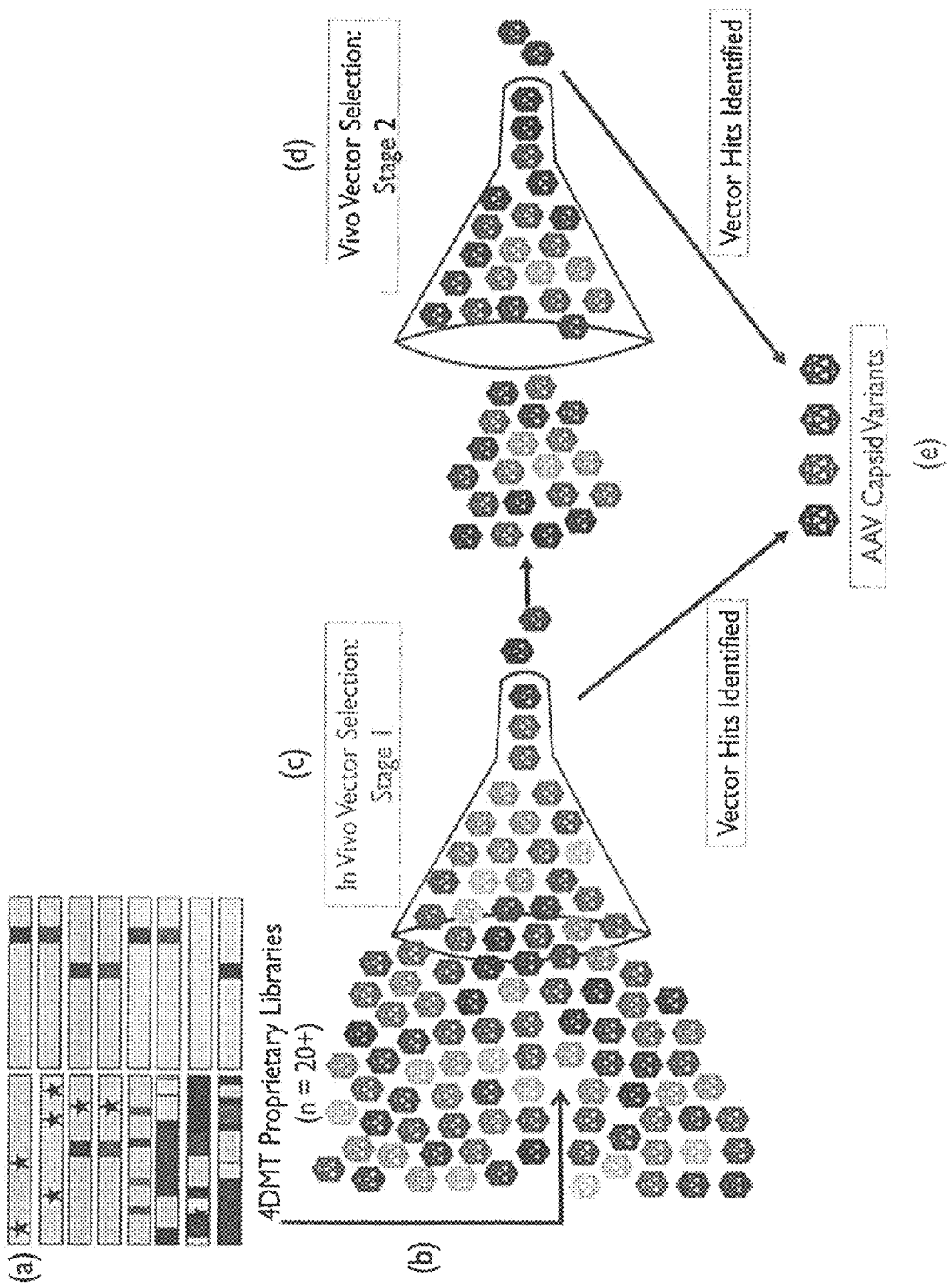
FIG. 1 depicts embodiments of a directed evolution methodology. Step (a) depicts the generation of a viral capsid library comprising combinations of DNA mutation techniques and cap genes. Step (b) depicts the packaging of the viruses such that each viral particle is composed of a mutant capsid surrounding the cap gene encoding that capsid and purified. The capsid library is then placed under selective pressure in vitro or in vivo. In this aspect of the directed evolution technology, tissues or cellular material of interest are harvested for isolation of AAV variants that have successfully infected that target, and the successful viruses are recovered. Step (c) depicts the Stage 1 enrichment of successful clones through repeated selection. Step (d) depicts the Stage 2 enrichment of selected cap genes which undergo re-diversification and further selection steps to iteratively increase viral fitness. Step (e) depicts the variants, identified as hits during Vector Selection Stages 1 and 2, which will be manufactured as recombinant AAV vectors and characterized for the level of transduction of various cell types and tissue targets. By the nature of the AAV directed evolution process, variants that are disclosed herein have already demonstrated the ability to transduce retinal cells and deliver a genome (the genome encoding the variant cap gene) during the selection process.

Before the present methods and compositions are described, it is to be understood that this invention is not limited to a particular method or composition described and as such may vary. It is also to be understood that the terminology used herein is for the purpose of describing particular embodiments only, and is not intended to be limiting, since the scope of the present invention will be limited only by the appended claims.

The invention disclosed herein is illustrated in the figures and description. However, while particular embodiments are illustrated in the figures, there is no intention to limit the invention to the specific embodiment or embodiments illustrated and/or disclosed. Rather, the invention disclosed herein is intended to cover all modifications, alternative constructions, and equivalents falling within the spirit and scope of the invention. As such, the figures are intended to be illustrative and not restrictive.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It is noted that as used herein and in the appended claims, the singular forms "a," "an," and "the" include plural referents unless the context clearly dictates otherwise. Thus, for example, reference to "a recombinant AAV virion" includes a plurality of such virions and reference to "the photoreceptor cell" includes reference to one or more photoreceptor cells and equivalents thereof known to those skilled in the art and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Unless otherwise defined, all scientific and technical terms used herein have the same meaning as commonly understood by one of ordinary skill in the art to which this technology belongs.

Adeno-associated virus is a nonpathogenic parvovirus composed of a 4.7 kb single-stranded DNA genome within a non-enveloped, icosahedral capsid. The genome contains three open reading frames (ORF) flanked by inverted terminal repeats (ITR) that function as the viral origin of replication and packaging signal. The rep ORF encodes four nonstructural proteins that play roles in viral replication, transcriptional regulation, site-specific integration, and virion assembly. The cap ORF encodes three structural proteins (VP 1-3) that assemble to form a 60-mer viral capsid. Finally, an ORF present as an alternate reading frame within the cap gene produces the assembly-activating protein (AAP), a viral protein that localizes AAV capsid proteins to the nucleolus and functions in the capsid assembly process.

There are several naturally occurring ("wild-type") serotypes and over 100 known variants of AAV, each of which differs in amino acid sequence, particularly within the hypervariable regions of the capsid proteins, and thus in their gene delivery properties. No AAV has been associated with any human disease, making recombinant AAV attractive for clinical applications.

For the purposes of the disclosure herein, the terminology "AAV" is an abbreviation for adeno-associated virus, including, without limitation, the virus itself and derivatives thereof. Except where otherwise indicated, the terminology refers to all subtypes or serotypes and both replication-competent and recombinant forms. The term "AAV" includes, without limitation, AAV type 1 (AAV-1 or AAV1), AAV type 2 (AAV-2 or AAV2), AAV type 3A (AAV-3A or AAV3A), AAV type 3B (AAV-3B or AAV3B), AAV type 4 (AAV-4 or AAV4), AAV type 5 (AAV-5 or AAV5), AAV type 6 (AAV-6 or AAV6), AAV type 7 (AAV-7 or AAV7), AAV type 8 (AAV-8 or AAV8), AAV type 9 (AAV-9 or AAV9), AAV type 10 (AAV-10 or AAV10 or AAVrh10), avian AAV, bovine AAV, canine AAV, caprine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

The genomic sequences of various serotypes of AAV, as well as the sequences of the native terminal repeats (TRs), Rep proteins, and capsid subunits are known in the art. Such sequences may be found in the literature or in public databases such as GenBank. See, e.g., GenBank Accession Numbers NC_002077.1 (AAV1), AF063497.1 (AAV1), NC_001401.2 (AAV2), AF043303.1 (AAV2), J01901.1 (AAV2), U48704.1 (AAV3A), NC_001729.1 (AAV3A), AF028705.1 (AAV3B), NC_001829.1 (AAV4), U89790.1 (AAV4), NC_006152.1 (AA5), AF085716.1 (AAV-5), AF028704.1 (AAV6), NC_006260.1 (AAV7), AF513851.1 (AAV7), AF513852.1 (AAV8) NC_006261.1 (AAV-8), AY530579.1 (AAV9), AAT46337 (AAV10) and AAO88208 (AAVrh10); the disclosures of which are incorporated by reference herein for teaching AAV nucleic acid and amino acid sequences. See also, e.g., Srivistava et al. (1983) J. Virology 45:555; Chiorini et al. (1998) J. Virology 71:6823; Chiorini et al. (1999) J. Virology 73: 1309; Bantel-Schaal et al. (1999) J. Virology 73:939; Xiao et al. (1999) J. Virology 73:3994; Muramatsu et al. (1996) Virology 221:208; Shade et. al. (1986) J. Virol. 58:921; Gao et al. (2002) Proc. Nat. Acad. Sci. USA 99: 11854; Moris et al. (2004) Virology 33:375-383; international patent publications WO 00/28061, WO 99/61601, WO 98/11244; and U.S. Pat. No. 6,156,303.

The sequences of naturally existing cap (capsid) proteins associated with AAV serotypes are known in the art and include those disclosed herein as AAV1 (SEQ ID NO:1), AAV2 (SEQ ID NO:2), AAV3A (SEQ ID NO:3), AAV3B (SEQ ID NO:4), AAV4 (SEQ ID NO:5), AAV5 (SEQ ID NO:6), AAV6 (SEQ ID NO:7), AAV7 (SEQ ID NO:8), AAV8 (SEQ ID NO:9), AAV9 (SEQ ID NO:10), AAV10 (SEQ ID NO:1), and AAVrh10 (SEQ ID NO:12). The terms "variant AAV capsid protein" or "AAV variant' refer to an AAV capsid protein comprising an amino acid sequence that includes at least one modification or substitution (including deletion, insertion, point mutation, etc.) relative to a naturally existing or "wild-type" AAV capsid protein sequences, e.g. as set forth in SEQ ID NO:1-12 herein. A variant AAV capsid protein may have about 80% identity or more to the amino acid sequence of a wild type capsid protein, for example, 85% identity or more, 90% identity or more, or 95% identity or more to the amino acid sequence of the wild type capsid protein, for example, 98% or 99% identity to the wild type capsid protein. A variant AAV capsid protein may not be a wild type capsid protein.

For the purposes of the disclosure herein, "AAV virion" or "AAV viral particle" refers to a viral particle composed of at least one AAV capsid protein and an encapsidated AAV polynucleotide.

For the purposes of the disclosure herein, the terminology "rAAV" is an abbreviation that refers to recombinant adeno-associated virus. "Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

The term "rAAV vector" encompasses rAAV virions (i.e., rAAV viral particles) (e.g., an infectious rAAV virion), which by definition include an rAAV polynucleotide; and also encompasses polynucleotides encoding rAAV (e.g., a single stranded polynucleotide encoding rAAV (ss-rAAV); a double stranded polynucleotide encoding rAAV (ds-rAAV), e.g., plasmids encoding rAAV; and the like).

If an AAV virion comprises a heterologous polynucleotide (i.e. a polynucleotide other than a wild-type AAV genome, e.g., a transgene to be delivered to a target cell, an RNAi agent or CRISPR agent to be delivered to a target cell, etc.), it is typically referred to as a "recombinant AAV (rAAV) virion" or an "rAAV viral particle." In general, the heterologous polynucleotide is flanked by at least one, and generally by two, AAV inverted terminal repeat sequences (ITRs).

The term "packaging" refers to a series of intracellular events that result in the assembly and encapsidation of an AAV particle. AAV "rep" and "cap" genes refer to polynucleotide sequences encoding replication and encapsidation proteins of adeno-associated virus. AAV rep and cap are referred to herein as AAV "packaging genes."

The terminology "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

The terminology "helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans. For example, a plasmid or other expression vector comprising nucleotide sequences encoding one or more adenoviral proteins is transfected into a producer cell along with an rAAV vector.

The terminology "infectious" virus or viral particle is one that comprises a competently assembled viral capsid and is capable of delivering a polynucleotide component into a cell for which the viral species is tropic. The term does not necessarily imply any replication capacity of the virus. Assays for counting infectious viral particles are described elsewhere in this disclosure and in the art. Viral infectivity can be expressed as the ratio of infectious viral particles to total viral particles. Methods of determining the ratio of infectious viral particle to total viral particle are known in the art. See, e.g., Grainger et al. (2005) Mol. Ther. 11: S337 (describing a TCID50 infectious titer assay); and Zolotukhin et al. (1999) Gene Ther. 6:973. See also the Examples.

The term "tropism" as used herein refers to the preferential targeting by a virus (e.g., an AAV) of cells of a particular host species or of particular cell types within a host species. For example, a virus that can infect cells of the heart, lung, liver, and muscle has a broader (i.e., increased) tropism relative to a virus that can infect only lung and muscle cells. Tropism can also include the dependence of a virus on particular types of cell surface molecules of the host. For example, some viruses can infect only cells with surface glycosaminoglycans, while other viruses can infect only cells with sialic acid (such dependencies can be tested using various cells lines deficient in particular classes of molecules as potential host cells for viral infection). In some cases, the tropism of a virus describes the virus's relative preferences. For example, a first virus may be able to infect all cell types but is much more successful in infecting those cells with surface glycosaminoglycans. A second virus can be considered to have a similar (or identical) tropism as the first virus if the second virus also prefers the same characteristics (e.g., the second virus is also more successful in infecting those cells with surface glycosaminoglycans), even if the absolute transduction efficiencies are not similar. For example, the second virus might be more efficient than the first virus at infecting every given cell type tested, but if the relative preferences are similar (or identical), the second virus can still be considered to have a similar (or identical) tropism as the first virus. In some embodiments, the tropism of a virion comprising a subject variant AAV capsid protein is not altered relative to a naturally occurring virion. In some embodiments, the tropism of a virion comprising a subject variant AAV capsid protein is expanded (i.e., broadened) relative to a naturally occurring virion. In some embodiments, the tropism of a virion comprising a subject variant AAV capsid protein is reduced relative to a naturally occurring virion.

The terminology "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per 10 rAAV particles, less than about 1 rcAAV per $10^{12}$ rAAV particles, or no rcAAV).

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment herein that comprises a polynucleotide encompasses both the double-stranded form and each of two complementary single-stranded forms known or predicted to make up the double-stranded form.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970).

The term "gene" refers to a polynucleotide that performs a function of some kind in the cell. For example, a gene can contain an open reading frame that is capable of encoding a gene product. One example of a gene product is a protein, which is transcribed and translated from the gene. Another example of a gene product is an RNA, e.g. a functional RNA product, e.g., an aptamer, an interfering RNA, a ribosomal RNA (rRNA), a transfer RNA (tRNA), a non-coding RNA (ncRNA), a guide RNA for nucleases, etc., which is transcribed but not translated.

The terminology "gene expression product" or "gene product" is a molecule resulting from expression of a particular gene, as defined above. Gene expression products include, e.g., a polypeptide, an aptamer, an interfering RNA, a messenger RNA (mRNA), an rRNA, a tRNA, a non-coding RNA (ncRNA), and the like.

The term "siRNA agent" ("small interfering" or "short interfering RNA" (or siRNA)) is an RNA duplex of nucleotides that is targeted to a gene interest (a "target gene"). An "RNA duplex" refers to the structure formed by the complementary pairing between two regions of a RNA molecule, forming a region of double stranded RNA (dsRNA). siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. In some embodiments, siRNA-mediated gene targeting is accomplished through the use of DNA-directed RNA interference (ddRNAi) which is a gene-silencing technique that utilizes DNA constructs to activate an animal cell's endogenous RNA interference (RNAi) pathways. Such DNA constructs are designed to express self-complementary double-stranded RNAs, typically short-hairpin RNAs (shRNA), that once processed bring about silencing of a target gene or genes. Any RNA, including endogenous mRNAs or viral RNAs, can be silenced by designing constructs to express double-stranded RNA complementary to the desired mRNA target. As such, the RNA duplex portion of an siRNA agent can be part of a short hairpin structure referred to as shRNA. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length. In general, the level of expression product (e.g., mRNA, polypeptide, etc.) of a target gene is reduced by an siRNA agent (e.g., an siRNA, an shRNA, etc.) that contains specific double stranded nucleotide sequences that are complementary to at least a 19-25 nucleotide long segment (e.g., a 20-21 nucleotide sequence) of the target gene transcript, including the 5' untranslated (UT) region, the ORF, or the 3' UT region. In some embodiments, short interfering RNAs are about 19-25 nt in length. See, e.g., PCT applications WO00/44895, WO99/32619, WO01/75164, WO01/92513, WO01/29058, WO01/89304, WO02/16620, and WO02/29858; and U.S. Patent Publication No. 20040023390 for descriptions of siRNA technology. The siRNA and/or shRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

The terminology "antisense RNA" encompasses RNA that is complementary to a gene expression product. For example, an antisense RNA targeted to a specific mRNA is an RNA-based agent (or can be a modified RNA) that is complementary to the mRNA, where hybridization of the antisense RNA to the mRNA alters the expression of the mRNA (e.g., via altering the stability of the RNA, altering the translation of the RNA, etc.). Also included in "antisense RNA" are nucleic acids encoding an antisense RNA.

With regards to "CRISPR/Cas9 agents", the term "CRISPR" encompasses Clustered regularly interspaced short palindromic repeats/CRISPR-associated (Cas) systems that evolved to provide bacteria and archaea with adaptive immunity against viruses and plasmids by using CRISPR RNAs (crRNAs) to guide the silencing of invading nucleic acids. The Cas9 protein (or functional equivalent and/or variant thereof, i.e., Cas9-like protein) naturally contains DNA endonuclease activity that depends on association of the protein with two naturally occurring or synthetic RNA molecules called crRNA and tracrRNA (also called guide RNAs). In some cases, the two molecules are covalently linked to form a single molecule (also called a single guide RNA ("sgRNA")). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence.

If the Cas9 or Cas9-like protein retains its natural enzymatic function, it will cleave target DNA to create a double-strand break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Cas9-like proteins with decreased DNA-cleavage activity (even no DNA-cleaving activity) can still be guided to a target DNA to block RNA polymerase activity. Alternatively, the Cas9 or Cas9-like protein may be modified by fusing a VP64 transcription activation domain to the Cas9 protein and codelivering the fusion protein with a MS2-P65-HSF1 helper protein and a single guide RNA comprising MS2 RNA aptamers at the tetraloop and stem-loop to form a Synergistic Activation Mediator (Cas9-SAM) complex in the cell that activates transcription. Thus enzymatically inactive Cas9-like proteins can be targeted to a specific location in a target DNA by a DNA-targeting RNA in order to block or activate transcription of the target DNA. The term "CRISPR/Cas9 agents" as used herein encompasses all forms of CRISPR/Cas9 as described above or as known in the art.

Detailed information regarding CRISPR agents can be found, for example in (a) Jinek et. al., Science. 2012 Aug. 17; 337(6096):816-21: "A programmable dual-RNA-guided DNA endonuclease in adaptive bacterial immunity"; (b) Qi et al., Cell. 2013 Feb. 28; 152(5): 1173-83: "Repurposing CRISPR as an RNA-guided platform for sequence-specific control of gene expression", and (c) U.S. patent application Ser. No. 13/842,859 and PCT application number PCT/US13/32589; all of which are hereby incorporated by reference in their entirety. Thus, the term "CRISPR agent" as used herein encompasses any agent (or nucleic acid encoding such an agent), comprising naturally occurring and/or synthetic sequences, that can be used in the Cas9-based system (e.g., a Cas9 or Cas9-like protein; any component of a DNA-targeting RNA, e.g., a crRNA-like RNA, a tracrRNA-like RNA, a single guide RNA, etc.; a donor polynucleotide; and the like).

By "Zinc-finger nucleases" (ZFNs) it is meant artificial DNA endonucleases generated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double strand breaks. For more information on the use of ZFNs, see, for example: Asuri et al., Mol Ther. 2012 February; 20(2): 329-38; Bibikova et al. Science. 2003 May 2; 300(5620): 764; Wood et al. Science. 2011 Jul. 15; 333(6040):307; Ochiai et al. Genes Cells. 2010 August; 15(8):875-85; Takasu et. al., Insect Biochem Mol Biol. 2010 October; 40(10):759-65; Ekker et al, Zebrafish 2008 Summer, 5(2): 121-3; Young et al, Proc Natl Acad Sci USA. 2011 Apr. 26; 108(17):7052-7; Goldberg et al, Cell. 2010 Mar. 5; 140(5): 678-91; Geurts et al, Science. 2009 Jul. 24; 325(5939):433; Flisikowska et al, PLoS One. 2011; 6(6):e21045. doi: 10.1371/journal.pone.0021045. Epub 2011 Jun. 13; Hauschild et al, Proc Nat Acad Sci USA. 2011 Jul. 19; 108(29): 12013-7; and Yu et al, Cell Res. 2011 November; 21(11): 1638-40; all of which are herein incorporated by reference for their teachings related to ZFNs. The term "ZFN agent" encompasses a zinc finger nuclease and/or a polynucleotide comprising a nucleotide sequence encoding a zinc finger nuclease.

The terminology "Transcription activator-like effector nuclease" or "TALEN" agents refers to Transcription activator-like effector nucleases (TALENs) are artificial DNA endonucleases generated by fusing a TAL (Transcription activator-like) effector DNA binding domain to a DNA cleavage domain. TALENS can be quickly engineered to bind practically any desired DNA sequence and when introduced into a cell, TALENs can be used to edit target DNA in the cell (e.g., the cell's genome) by inducing double strand breaks. For more information on the use of TALENs, see, for example: Hockemeyer et al. Nat Biotechnol. 2011 Jul. 7; 29(8):731-4; Wood et al. Science. 2011 Jul. 15; 333(6040):307; Tesson et al. Nat Biotechnol. 2011 Aug. 5; 29(8):695-6; and Huang et. al., Nat Biotechnol. 2011 Aug. 5; 29(8):699-700; all of which are herein incorporated by reference for their teachings related to TALENs. The term "TALEN agent" encompasses a TALEN and/or a polynucleotide comprising a nucleotide sequence encoding a TALEN.

The terminology "control element" or "control sequence" refers to a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters may be ubiquitously acting, i.e. active in many cell types, e.g. CAG or CMV promoters; or tissue or cell specific, e.g. the rho promoter, which is active in rods, or the opsin promoter, which is active in cones.

The terminology "operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

The terminology "expression vector" encompasses a vector comprising a polynucleotide region which encodes a polypeptide of interest, and is used for effecting the expression of the protein in an intended target cell. An expression vector may also comprise control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

The term "heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid sequence encoding a heterologous gene product is an rAAV that includes a polynucleotide not normally included in a naturally-occurring, wild-type AAV, and the encoded heterologous gene product is a gene product not normally encoded by a naturally-occurring, wild type AAV.

The terminology "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Generally, the genetic element is introduced into a chromosome or mini-chromosome in the cell; but any alteration that changes the phenotype and/or genotype of the cell and its progeny is included in this term.

With regards to cell modification, the terminology "genetically modified" or "transformed" or "transfected" or "transduced" by exogenous DNA (e.g. via a recombinant virus) refers to when such DNA has been introduced inside the cell. The presence of the exogenous DNA results in permanent or transient genetic change. The transforming DNA may or may not be integrated (covalently linked) into the genome of the cell. A "clone" is a population of cells derived from a single cell or common ancestor by mitosis. A "cell line" is a clone of a primary cell that is capable of stable growth in vitro for many generations.

As used herein, a cell is said to be "stably" altered, transduced, genetically modified, or transformed with a genetic sequence if the sequence is available to perform its function during extended culture of the cell in vitro and/or for an extended period of time in vivo. Generally, such a cell is "heritably" altered (genetically modified) in that a genetic alteration is introduced which is also inheritable by progeny of the altered cell.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

As used herein, an "isolated" plasmid, nucleic acid, vector, virus, virion, host cell, protein, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this disclosure are increasingly more isolated. An isolated plasmid, nucleic acid, vector, virus, host cell, or other substance is in some embodiments purified, e.g., from about 8% to about 90% pure, at least about 90% pure, at least about 95% pure, at least about 98% pure, or at least about 99%, or more, pure.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease (and/or symptoms caused by the disease) from occurring in a subject which may be predisposed to the disease or at risk of acquiring the disease but has not yet been diagnosed as having it; (b) inhibiting the disease (and/or symptoms caused by the disease), i.e., arresting its development; and (c) relieving the disease (and/or symptoms caused by the disease), i.e., causing regression of the disease (and/or symptoms caused by the disease), i.e., ameliorating the disease and/or one or more symptoms of the disease. For example, the subject compositions and methods may be directed towards the treatment of retinal disease. Nonlimiting methods for assessing retinal diseases and the treatment thereof include measuring retinal function and changes thereof, e.g. changes in visual acuity (e.g. best-corrected visual acuity [BCVA], ambulation, navigation, object detection and discrimination), changes in visual field (e.g. static and kinetic visual field perimetry), clinical examination (e.g. slit lamp examination of the anterior and posterior segments of the eye), electrophysiological responsiveness to all wavelengths of light and dark (e.g. all forms of electroretinography (ERG) [full-field, multifocal and pattern], all forms of visual evoked potential (VEP), electrooculography (EOG), color vision, dark adaptation and/or contrast sensitivity; measuring changes in anatomy or health using anatomical and/or photographic measures, e.g. Optical Conherence Tomography (OCT), fundus photography, adaptive optics scanning laser ophthalmoscopy, fluorescence and/or autofluorescence; measuring ocular motility and eye movements (e.g. nystagmus, fixation preference, and stability), measuring reported outcomes (patient-reported changes in visual and non-visually-guided behaviors and activities, patient-reported outcomes [PRO], questionnaire-based assessments of quality-of-life, daily activities and measures of neurological function (e.g. functional Magnetic Resonance Imaging (MRI)).

The terms "individual," "host," "subject," and "patient" are used interchangeably herein, and refer to a mammal, including, but not limited to, humans; non-human primates, including simians; mammalian sport animals (e.g., horses); mammalian farm animals (e.g., sheep, goats, etc.); mammalian pets (dogs, cats, etc.); and rodents (e.g., mice, rats, etc.).

In some embodiments, the individual is a human who has previously been naturally exposed to AAV and as a result harbors anti-AAV antibodies (i.e., AAV neutralizing antibodies). In some embodiments, the individual is a human who has previously been administered an AAV vector (and as a result may harbor anti-AAV antibodies) and needs re-administration of vector for treatment of a different condition or for further treatment of the same condition. Based on positive results in clinical trials involving AAV gene delivery to, for example, liver, muscle, and retina—all tissues affected by neutralizing antibodies against this vehicle—there are many such therapeutic applications/disease targets.

The term "effective amount" as used herein is an amount sufficient to effect beneficial or desired clinical results. An effective amount can be administered in one or more administrations. For purposes of this disclosure, an effective amount of a compound (e.g., an infectious rAAV virion) is an amount that is sufficient to palliate, ameliorate, stabilize, reverse, prevent, slow or delay the progression of (and/or symptoms associated with) a particular disease state (e.g., a retinal disease). Accordingly, an effective amount of an infectious rAAV virion is an amount of the infectious rAAV virion that is able to effectively deliver a heterologous nucleic acid to a target cell (or target cells) of the individual. Effective amounts may be determined preclinically by, e.g., detecting in the cell or tissue the gene product (RNA, protein) that is encoded by the heterologous nucleic acid sequence using techniques that are well understood in the art, e.g. RT-PCR, western blotting, ELISA, fluorescence or other reporter readouts, and the like. Effective amounts may be determined clinically by, e.g. detecting a change in the onset or progression of disease using methods known in the art, e.g. fundus autofluorescence, fluorescein angiography, OCT, microperimetry, adaptive optics, etc. and the like, as described herein and as known in the art.

The terminology "retinal cell" refers herein to any of the cell types that comprise the retina, such as, without limitation, retinal ganglion (RG) cells, amacrine cells, horizontal cells, bipolar cells, photoreceptor cells, Müller glial cells, microglial cells, and retinal pigmented epithelium (RPE). The terminology "photoreceptor cells" refers herein to, without limitation, rod cells or "rods" and cone cells or "cones". The terminology "Müller cells" or "Müller glia" refers to glial cells that support neurons in the vertebrate retina.

The terminology "directed evolution" refers to a capsid engineering methodology, in vitro and/or in vivo, which emulates natural evolution through iterative rounds of genetic diversification and selection processes, thereby accumulating beneficial mutations that progressively improve the function of a biomolecule. Directed evolution often involves an in vivo method referred to as "biopanning" for selection of AAV variants from a library which variants possess a more efficient level of infectivity of a cell or tissue type of interest.

DETAILED DESCRIPTION

Adeno-associated viruses (AAVs) are a family of parvoviruses with a 4.7 kb single-stranded DNA genome contained inside a non-enveloped capsid. The viral genome of a naturally occurring AAV has 2 inverted terminal repeats (ITR)—which function as the viral origin of replication and packaging signal—flanking 2 primary open reading frames (ORF): rep (encoding proteins that function in viral replication, transcriptional regulation, site-specific integration, and virion assembly) and cap. The cap ORF codes for 3 structural proteins that assemble to form a 60-mer viral capsid. Many naturally occurring AAV variants and serotypes have been isolated, and none have been associated with human disease.

Recombinant versions of AAV can be used as gene delivery vectors, where a marker or therapeutic gene of interest is inserted between the ITRs in place of rep and cap. These vectors have been shown to transduce both dividing and non-dividing cells in vitro and in vivo and can result in stable transgene expression for years in post-mitotic tissue. See e.g., Knipe D M, Howley P M. *Fields' Virology*. Lippincott Williams & Wilkins, Philadelphia, Pa., USA, 2007; Gao G-P, Alvira M R, Wang L, Calcedo R, Johnston J, Wilson J M. Novel adeno-associated viruses from rhesus monkeys as vectors for human gene therapy. *Proc Natl Acad Sci USA* 2002; 99: 11854-9; Atchison R W, Casto B C, Hammon W M. Adenovirus-Associated Defective Virus Particles. *Science* 1965; 149: 754-6; Hoggan M D, Blacklow N R, Rowe W P. Studies of small DNA viruses found in various adenovirus preparations: physical, biological, and immunological characteristics. *Proc Nal Acad Sci USA* 1966; 55: 1467-74; Blacklow N R, Hoggan M D, Rowe W P. Isolation of adenovirus-associated viruses from man. *Proc Natl Acad Sci USA* 1967; 58: 1410-5; Bantel-Schaal U, zur Hausen H. Characterization of the DNA of a defective human parvovirus isolated from a genital site. *Virology* 1984; 134: 52-63; Mayor H D, Melnick J L. Small deoxyribonucleic acid-containing viruses (picodnavirus group). *Nature* 1966; 210: 331-2; Mori S, Wang L, Takeuchi T, Kanda T. Two novel adeno-associated viruses from cynomolgus monkey: pseudotyping characterization of capsid protein. *Virology* 2004; 330: 375-83; Flotte T R. Gene therapy progress and prospects: recombinant adeno-associated virus (rAAV) vectors. *Gene Ther* 2004; 11: 805-10.

Recombinant AAV (referred to herein simply as "AAV") has yielded promising results in an increasing number of clinical trials. However, there are impediments to gene delivery that may limit AAV's utility, such as anti-capsid immune responses, low transduction of certain tissues, an inability for targeted delivery to specific cell types and a relatively low carrying capacity. In many situations, there is insufficient mechanistic knowledge to effectively empower rational design with the capacity to improve AAV. As an alternative, directed evolution has emerged as a strategy to create novel AAV variants that meet specific biomedical needs. Directed evolution strategies harness genetic diversification and selection processes to enable the accumulation of beneficial mutations that progressively improve the function of a biomolecule. In this process, wild-type AAV cap genes are diversified by several approaches to create large genetic libraries that are packaged to generate libraries of viral particles, and selective pressure is then applied to isolate novel variants that can overcome gene delivery barriers. Importantly, the mechanistic basis underlying a gene delivery problem does not need to be known for directed evolution of function, which can thus accelerate the development of enhanced vectors.

Typically, the variants disclosed herein were generated through use of an AAV library and/or libraries. Such an AAV library or libraries is/are generated by mutating the cap gene, the gene which encodes the structural proteins of the AAV capsid, by a range of directed evolution techniques known by and readily available to the skilled artisan in the field of viral genome engineering. See e.g., Bartel et al. Am. Soc. Gene Cell Ther. $15^{th}$ Annu. Meet. 20, S140 (2012); Bowles, D. et al. J. Virol. 77, 423-432 (2003); Gray et al. Mol. Ther. 18, 570-578 (2010); Grimm, D. et al. J. Virol. 82, 5887-5911; Koerber, J. T. et al. Mol. Ther. 16, 1703-1709 (2008); Li W. et al. Mol. Ther. 16, 1252-1260 (2008); Koerber, J. T. et al. Methods Mol. Biol. 434, 161-170 (2008); Koerber, J. T. et al. Hum. Gene Ther. 18, 367-378 (2007); and Koerber, J. T. et al. Mol. Ther. 17, 2088-2095 (2009). Such techniques, without limitation, are as follows: i) Error-prone PCR to introduce random point mutations into the AAV cap open reading frame (ORF) at a predetermined, modifiable rate; ii) In vitro or in vivo viral recombination or "DNA shuffling" to generate random chimeras of AAV cap genes to yield a gene library with multiple AAV serotypes; iii) Random peptide insertions at defined sites of the capsid by ligation of degenerate oligonucleotides in the cap ORF; iv) Defined insertions of peptide-encoding sequences into random locations of the AAV cap ORF using transposon mutagenesis; v) Replacing surface loops of AAV capsids with libraries of peptide sequences bioinformationally designed based on the level of conservation of each amino acid position among natural AAV serotypes and variants to generate "loop-swap" libraries; vi) Random amino acid substitution at positions of degeneracy between AAV serotypes to generate libraries of ancestral variants (Santiago-Ortiz et al., 2015); and a combination of such techniques thereof.

DNA shuffling generates chimeras which combine their parental properties in unique and, often beneficial, ways; however, some may be incapable of packaging which, in effect, reduces the diversity of the library. Diversity concentration of the library is achieved through peptide insertion techniques such as, without limitation, iii-iv) above. Diversity of the library is also concentrated in techniques such as v) above, and such concentration is directed onto multiple hypervariable regions, which lie on surface exposed loops, of the AAV capsid. While many of the techniques generate variant capsids with only a small area of the capsid mutated, these techniques can be paired with additional mutagenesis strategies to modify the full capsid.

Once the AAV library or libraries is/are generated, viruses are then packaged, such that each AAV particle is comprised of a mutant capsid surrounding a cap gene encoding that capsid, and purified. Variants of the library are then subjected to in vitro and/or in vivo selective pressure techniques known by and readily available to the skilled artisan in the field of AAV. See e.g., Maheshri, N. et al. Nature Biotech. 24, 198-204 (2006); Dalkara, D. et al. Sci. Transl. Med. 5, 189ra76 (2013); Lisowski, L. et al. Nature. 506, 382-286 (2013); Yang, L. et al. PNAS. 106, 3946-3951 (2009); Gao, G. et al. Mol. Ther. 13, 77-87 (2006); and Bell, P. et al. Hum. Gene. Ther. 22, 985-997 (2011). For example, without limitation, AAV variants can be selected using i) affinity columns in which elution of different fractions yields variants with altered binding properties; ii) primary cells— isolated from tissue samples or immortal cells lines that mimic the behavior of cells in the human body—which yield AAV variants with increased efficiency and/or tissue specificity; iii) animal models—which mimic a clinical gene therapy environment—which yield AAV variants that have successfully infected target tissue; iv) human xenograft models which yield AAV variants that have infected grafted human cells; and/or a combination of selection techniques thereof.

Once viruses are selected, they may be recovered by known techniques such as, without limitation, adenovirus-mediated replication, PCR amplification, Next Generation sequencing and cloning, and the like. Virus clones are then enriched through repeated rounds of the selection techniques and AAV DNA is isolated to recover selected variant cap genes of interest. Such selected variants can be subjected to further modification or mutation and as such serve as a new starting point for further selection steps to iteratively increase AAV viral fitness. However, in certain instances, successful capsids have been generated without additional mutation.

The AAV variants disclosed herein were generated at least in part through the use of in vivo directed evolution methodology, such as the techniques described above, involving the use of primate retinal screens following intravitreal administration. As such, he AAV variant capsids disclosed herein comprise one or more modifications in amino acid sequence that confer more efficient transduction of primate retinal cells than a corresponding parental AAV capsid protein. As used herein, a "corresponding parental AAV capsid protein" refers to an AAV capsid protein of the same wild-type or variant AAV serotype as the subject variant AAV capsid protein but that does not comprise the one or more amino acid sequence modifications of the subject variant AAV capsid protein.

Figure 6:
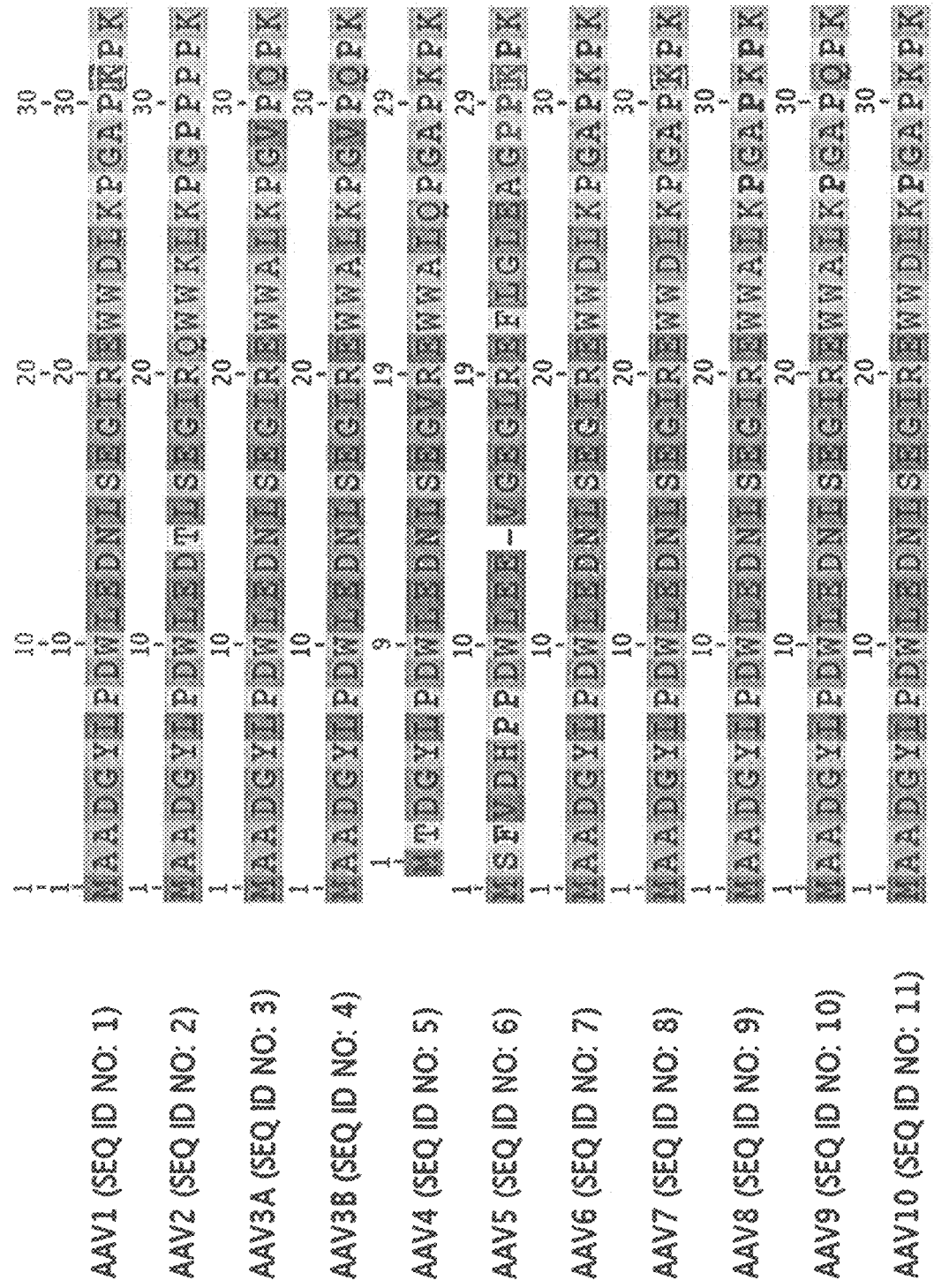
FIG. 6 provides an alignment of wild-type AAV SEQ ID NOS:1-11 showing amino acid locations between and across the wild-type (naturally occurring) serotypes AAV1, AAV2, AAV3A, AAV3B, and AAV4-10.
Figure 6:
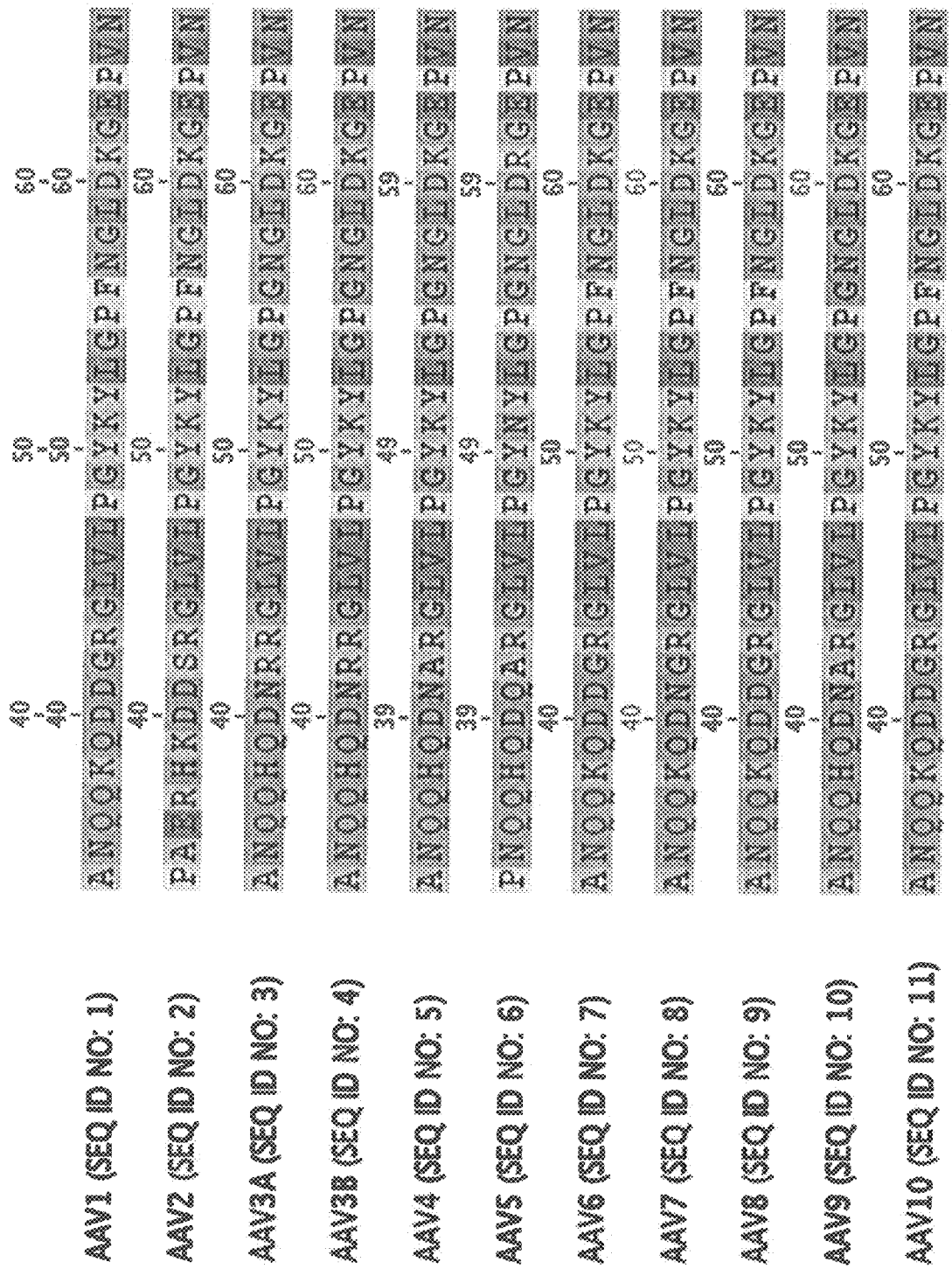
Figure 6:
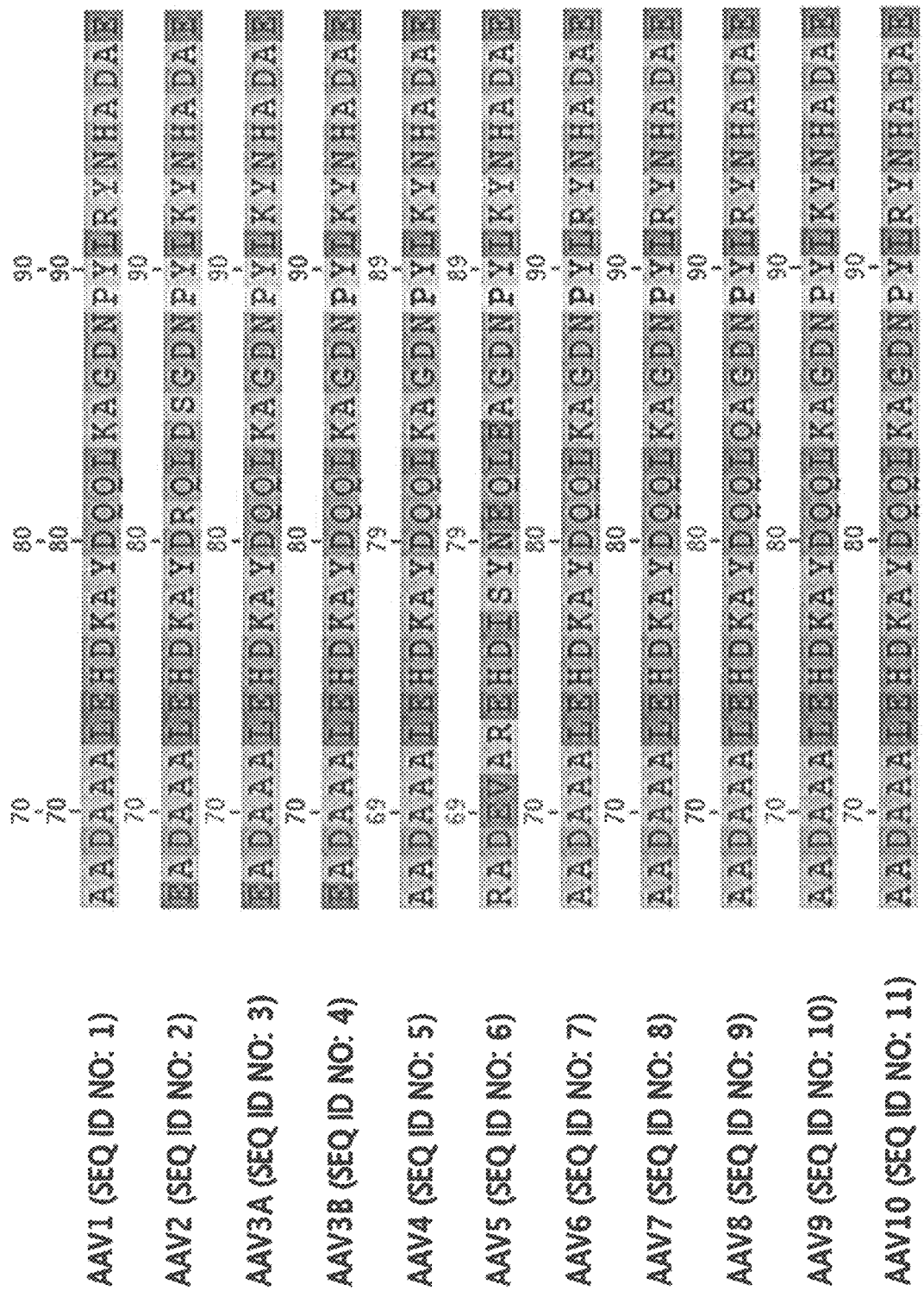
Figure 6:
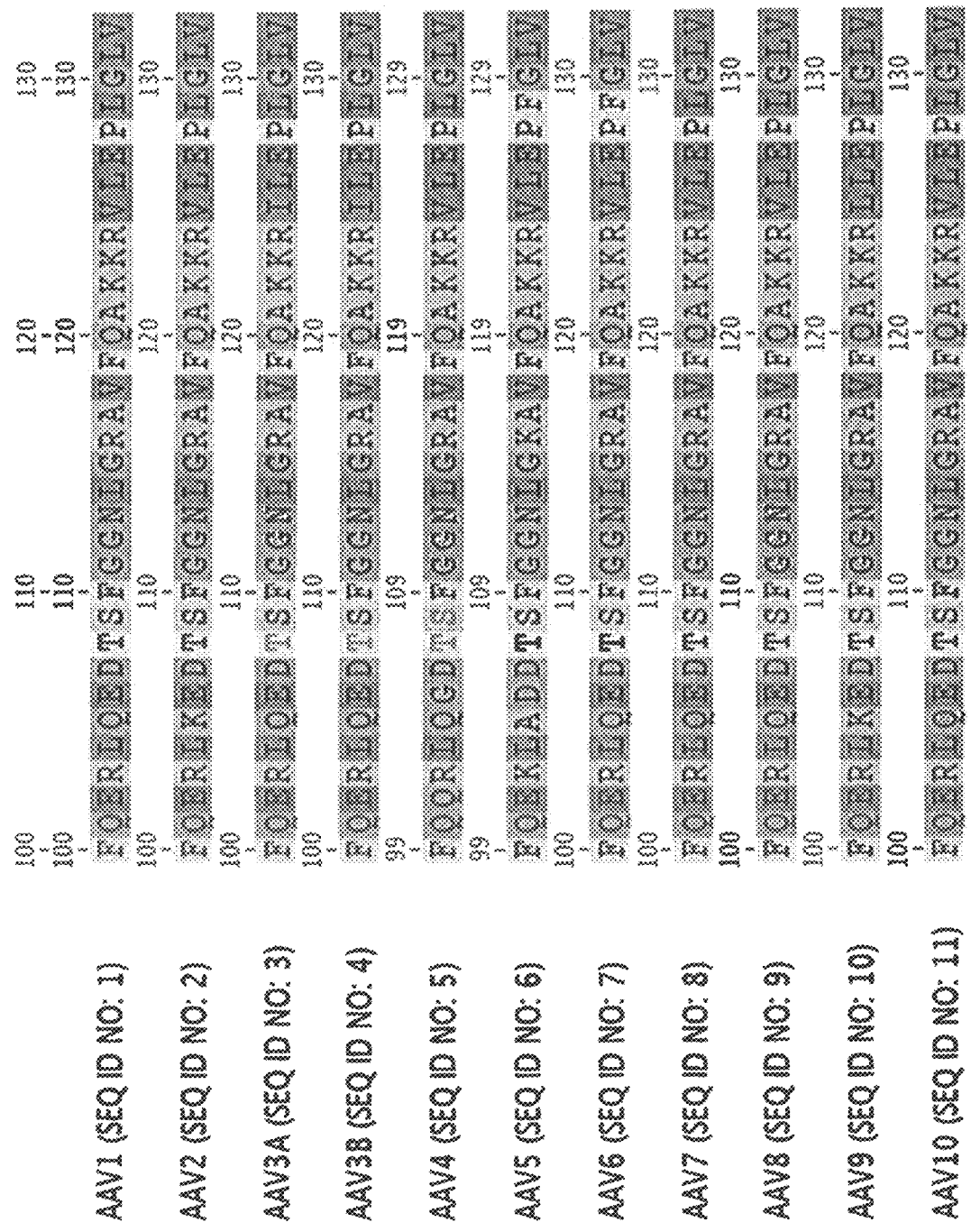
Figure 6:
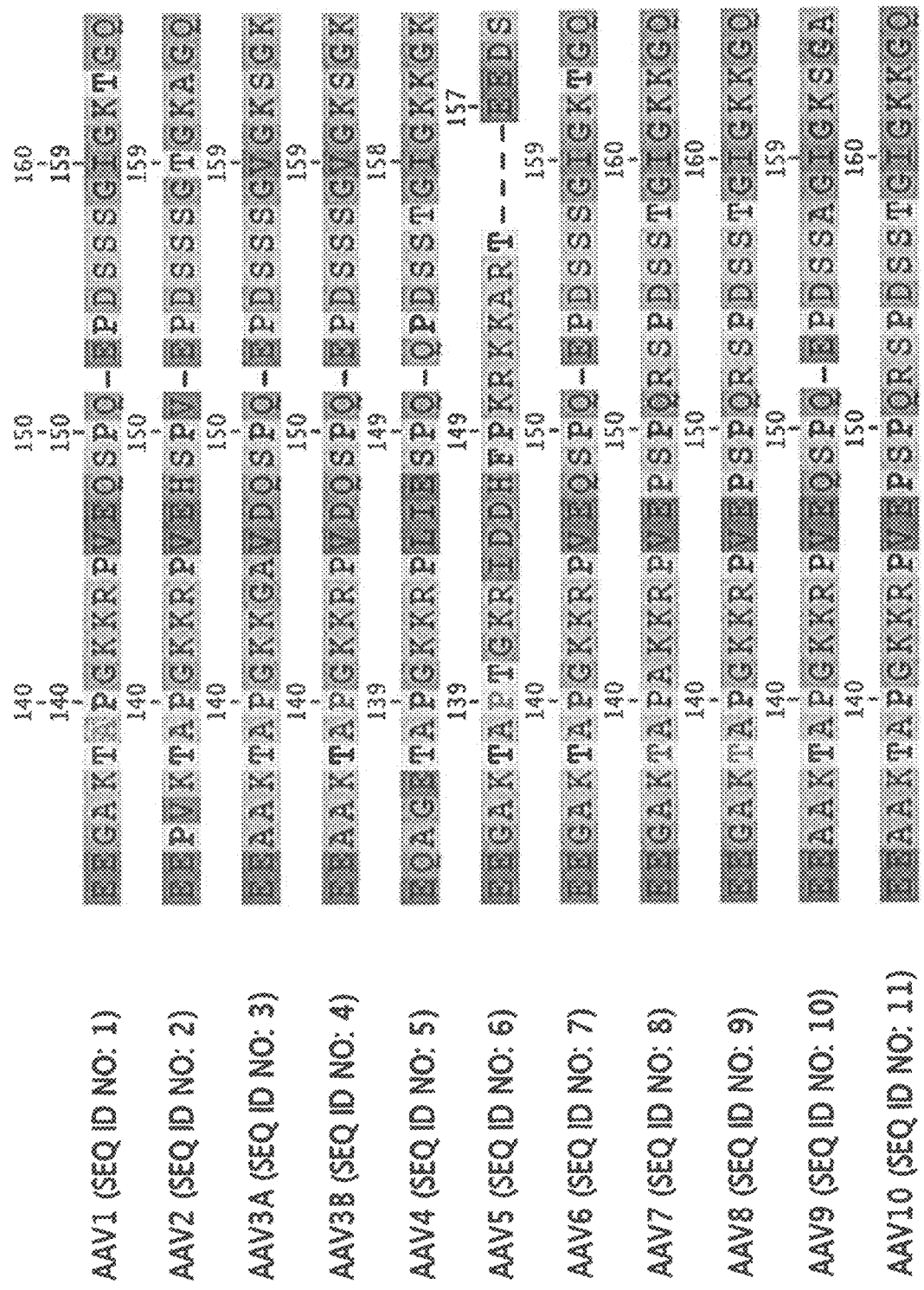
Figure 6:
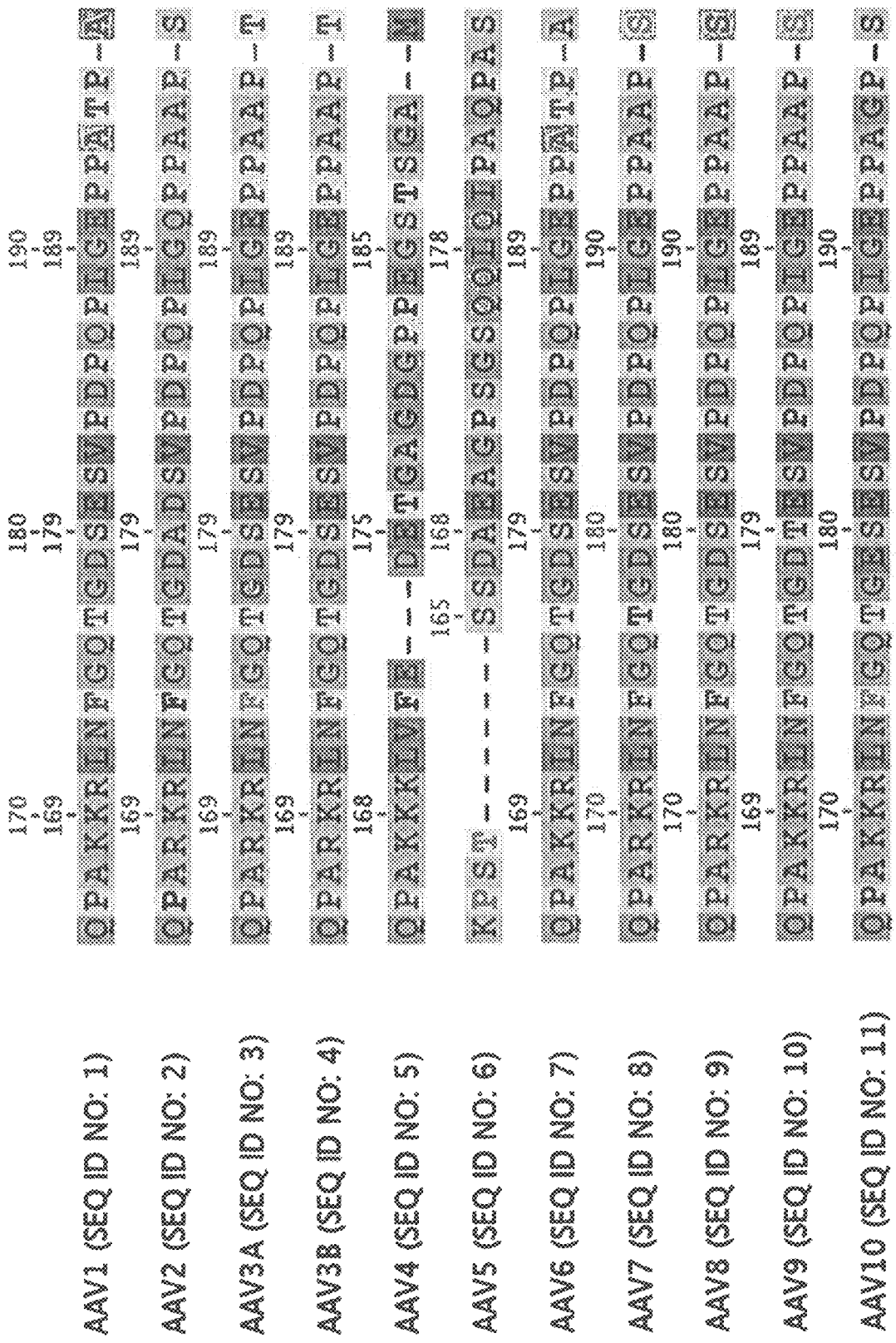
Figure 6:
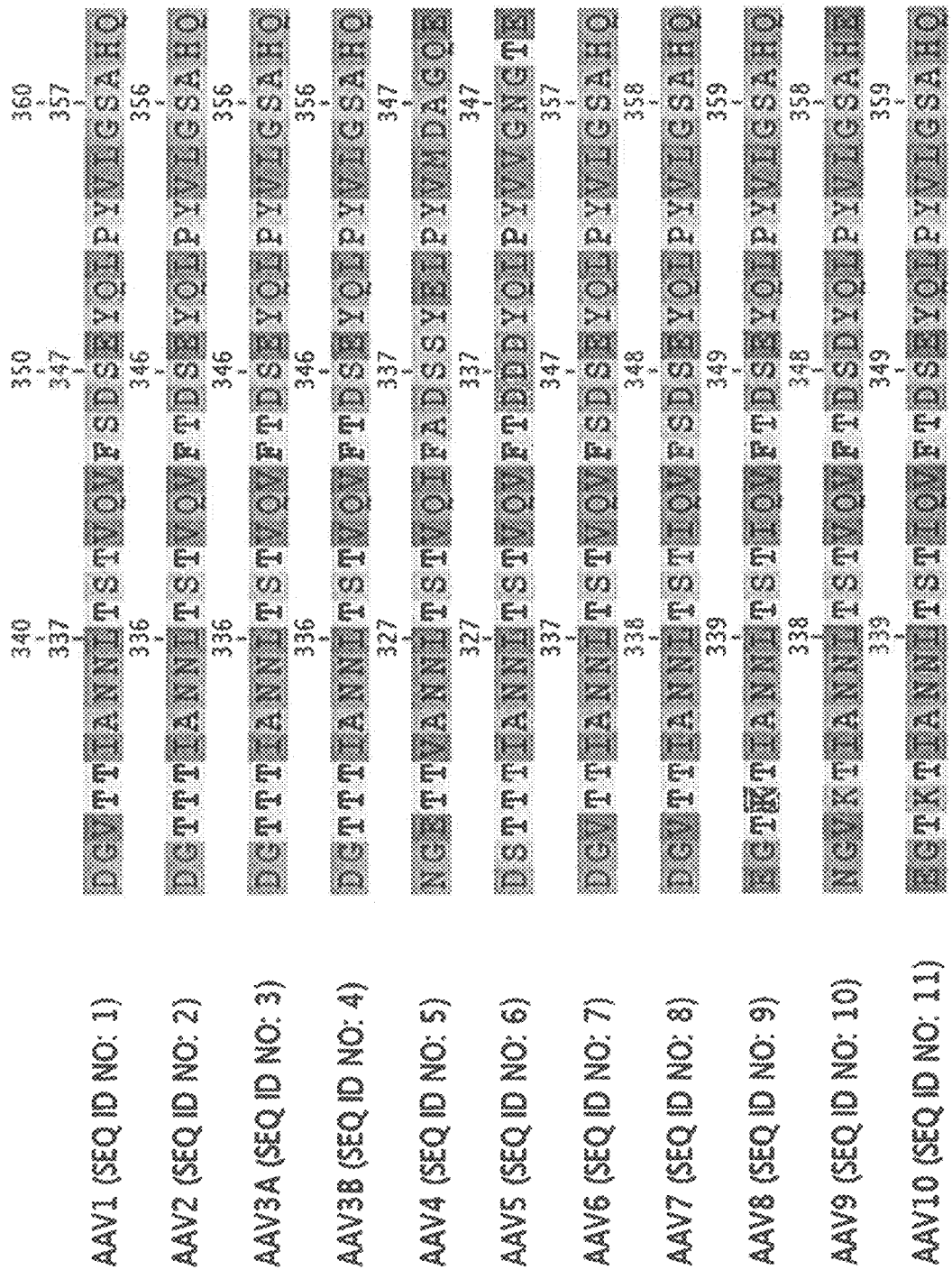
Figure 6:
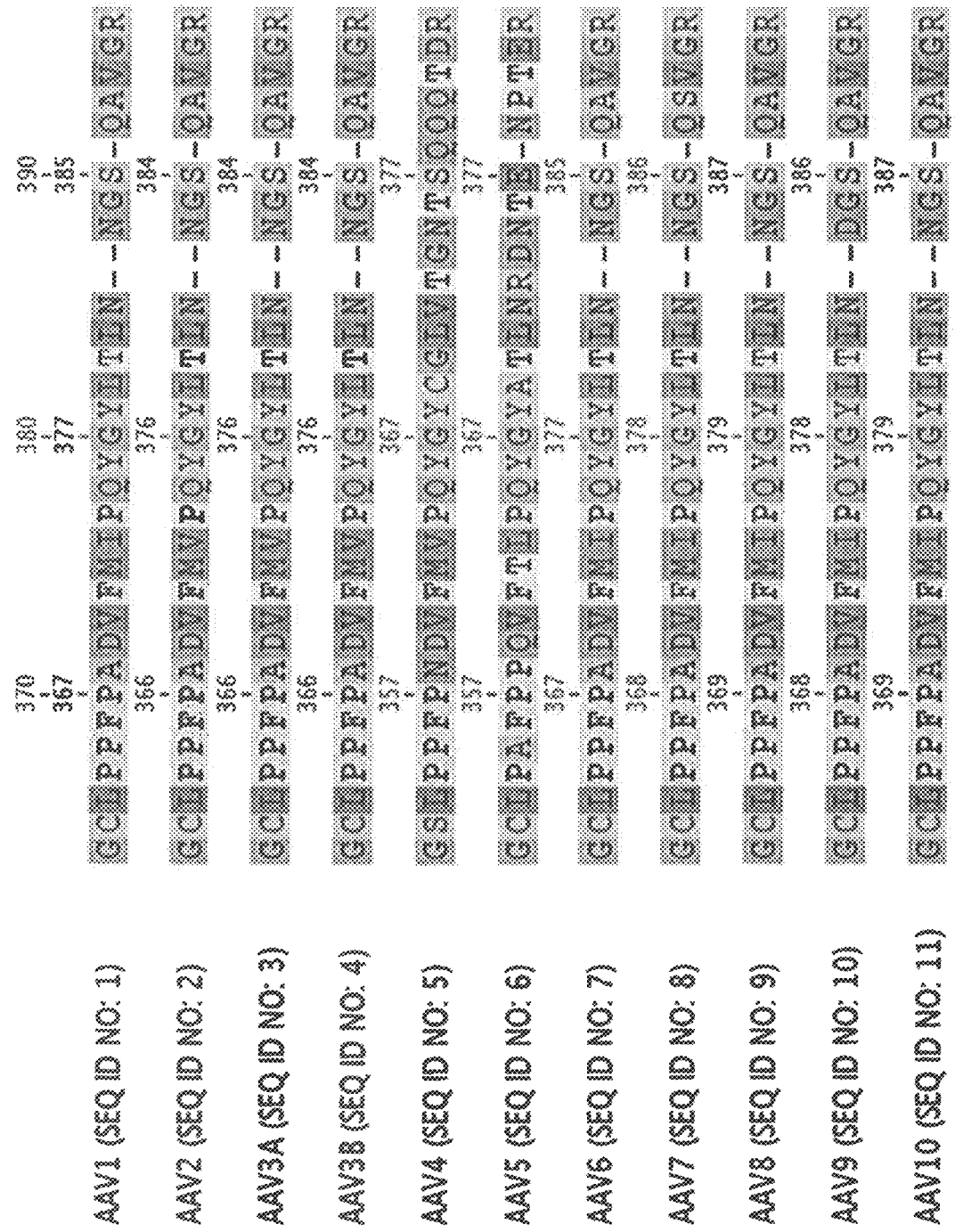
Figure 6:
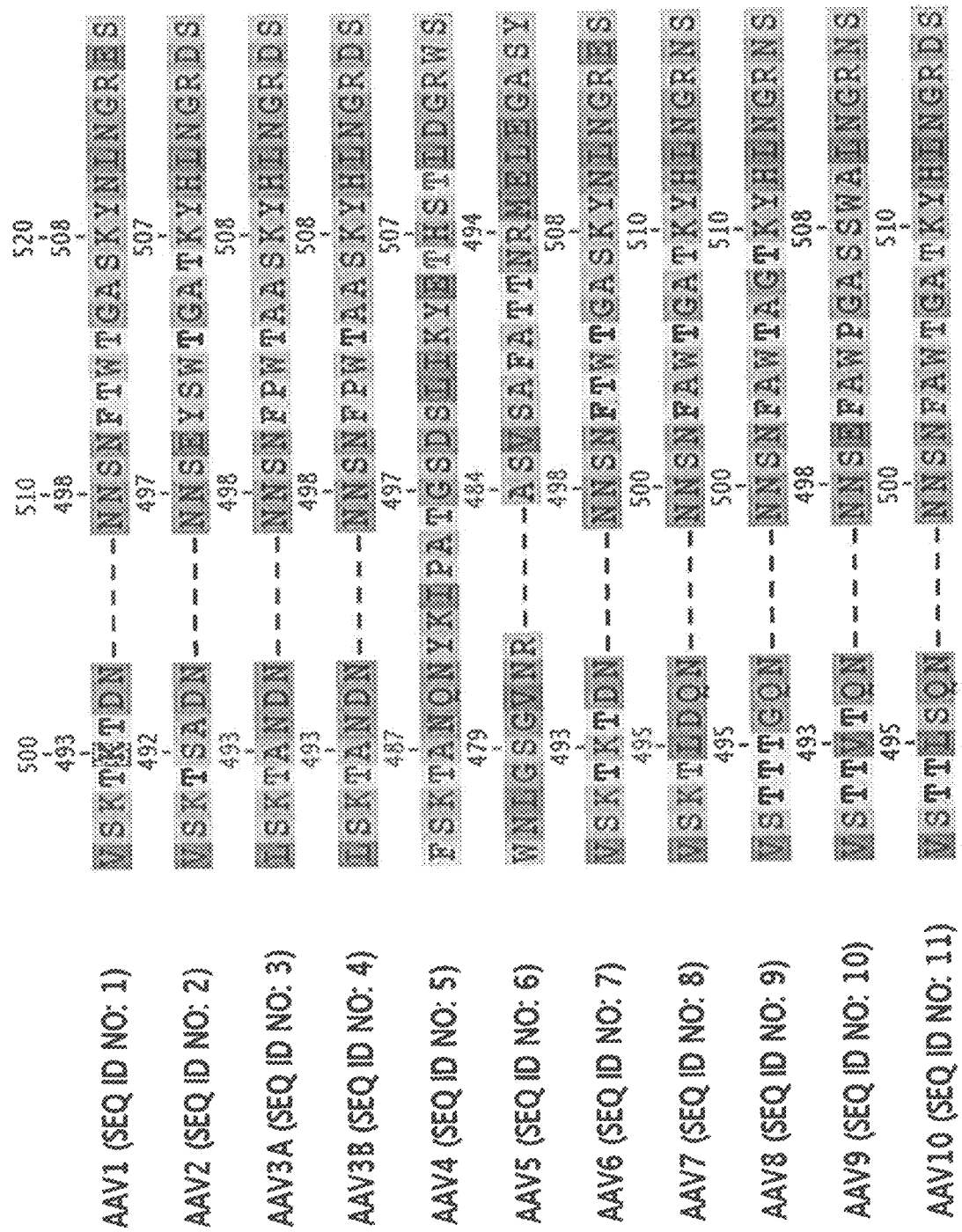
Figure 6:
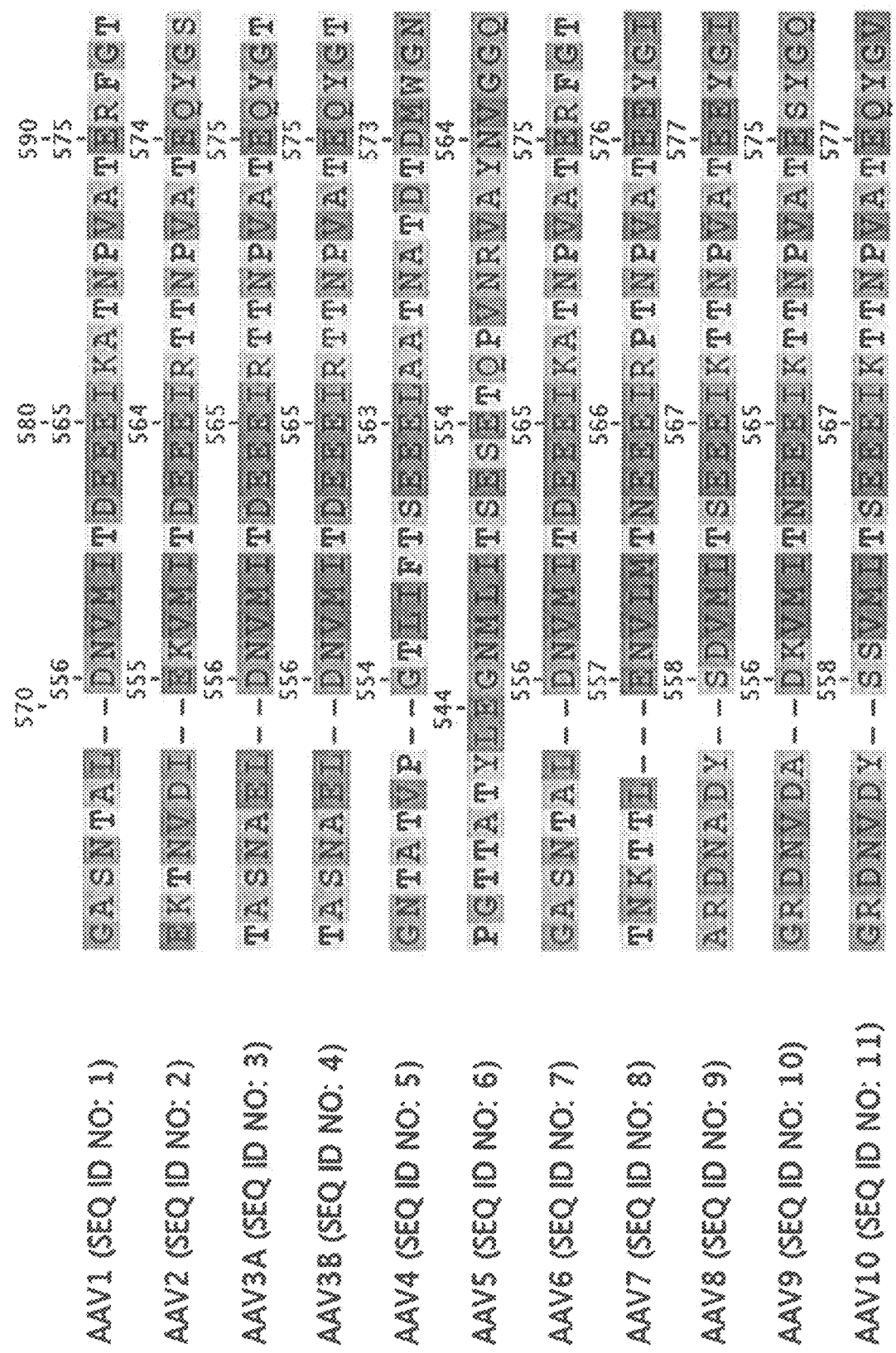

In some embodiments, the subject variant AAV capsid protein comprises a heterologous peptide of from about 5 amino acids to about 20 amino acids inserted by covalent linkage into an AAV capsid protein GH loop, or loop IV, relative to a corresponding parental AAV capsid protein. By the "GH loop," or loop IV, of the AAV capsid protein it is meant the solvent-accessible portion referred to in the art as the GH loop, or loop IV, of AAV capsid protein. For the GH loop/loop IV of AAV capsid, see, e.g., van Vliet et al. (2006) *Mol. Ther.* 14:809; Padron et al. (2005) *J. Virol.* 79:5047; and Shen et al. (2007) *Mol. Ther.* 15:1955. Thus, for example, the insertion site can be within about amino acids 411-650 of an AAV VP1 capsid protein. For example, the insertion site can be within amino acids 571-612 of AAV1 VP1, amino acids 570-611 of AAV2 VP1, within amino acids 571-612 of AAV3A VP1, within amino acids 571-612 of AAV3B VP1, within amino acids 569-610 of AAV4 VP1, within amino acids 560-601 of AAV5 VP1, within amino acids 571 to 612 of AAV6 VP1, within amino acids 572 to 613 of AAV7 VP1, within amino acids 573 to 614 of AAV8 VP1, within amino acids 571 to 612 of AAV9 VP1, or within amino acids 573 to 614 of AAV10 VP1, or the corresponding amino acids of any variant thereof. Those skilled in the art would know, based on a comparison of the amino acid sequences of capsid proteins of various AAV serotypes, where an insertion site "corresponding to amino acids of AAV2" would be in a capsid protein of any given AAV serotype. See also FIG. 6 for an alignment of wild-type AAV SEQ ID NOS:1-11 which provides amino acid locations between and across the wild-type (naturally occurring) serotypes AAV1, AAV2, AAV3A, AAV3B, and AAV4-10.

In certain embodiments, the insertion site is a single insertion site between two adjacent amino acids located between amino acids 570-614 of VP1 of any wild-type AAV serotype or AAV variant, e.g., the insertion site is between two adjacent amino acids located in amino acids 570-610, amino acids 580-600, amino acids 570-575, amino acids 575-580, amino acids 580-585, amino acids 585-590, amino acids 590-600, or amino acids 600-614, of VP1 of any AAV serotype or variant. For example, the insertion site can be between amino acids 580 and 581, amino acids 581 and 582, amino acids 583 and 584, amino acids 584 and 585, amino acids 585 and 586, amino acids 586 and 587, amino acids 587 and 588, amino acids 588 and 589, or amino acids 589 and 590. The insertion site can be between amino acids 575 and 576, amino acids 576 and 577, amino acids 577 and 578, amino acids 578 and 579, or amino acids 579 and 580. The insertion site can be between amino acids 590 and 591, amino acids 591 and 592, amino acids 592 and 593, amino acids 593 and 594, amino acids 594 and 595, amino acids 595 and 596, amino acids 596 and 597, amino acids 597 and 598, amino acids 598 and 599, or amino acids 599 and 600. For example, the insertion site can be between amino acids 587 and 588 of AAV2, between amino acids 590 and 591 of AAV1, between amino acids 588 and 589 of AAV3A, between amino acids 588 and 589 of AAV3B, between amino acids 584 and 585 of AAV4, between amino acids 575 and 576 of AAV5, between amino acids 590 and 591 of AAV6, between amino acids 589 and 590 of AAV7, between amino acids 590 and 591 of AAV8, between amino acids 588 and 589 of AAV9, or between amino acids 588 and 589 of AAV10.

In some embodiments, a peptide insertion disclosed herein has a length of 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, or 20 amino acids. In another embodiment, a peptide insertion disclosed herein comprises from 1 to 4 spacer amino acids at the amino terminus (N-terminus) and/or at the carboxyl terminus (C-terminus) of any one of the peptide insertions disclosed herein. Exemplary spacer amino acids include, without limitation, leucine (L), alanine (A), glycine (G), serine (S), threonine (T), and proline (P). In certain embodiments, a peptide insertion comprises 2 spacer amino acids at the N-terminus and 2 spacer amino acids at the C-terminus. In other embodiments, a peptide insertion comprises 2 spacer amino acids at the N-terminus and 1 spacer amino acids at the C-terminus.

The peptide insertions disclosed herein have not been previously described and/or inserted into an AAV capsid. Without wishing to be bound by theory, the presence of any of the disclosed peptide insertions may act to lower the variant capsid's affinity for heparin sulfate which likely reduces binding to the extracellular matrix in the front of the primate retina. In addition, the peptide insertion motifs disclosed herein may confer enhanced transduction of primate retinal cells through the addition of a cell surface receptor binding domain.

In some preferred embodiments, the insertion peptide comprises an amino acid sequence of any one of the formulas below.

In some aspects, an insertion peptide can be a peptide of 7 to 10 amino acids in length, of Formula 1a:

$$Y_1Y_2X_1X_2X_3X_4X_5X_6X_7Y_3$$

Where each of $Y_1$-$Y_3$, if present, is independently selected from Ala, Leu, Gly, Ser, Thr, Pro
$X_1$ is selected from Gln, Asn, His, Ile, and Ala
$X_2$ is selected from Ala, Gln, Asp, Ser, Lys, and Pro
$X_3$ is selected from Asp, Ile, Thr and Asn
$X_4$ is selected from Thr, Ser, Tyr, Gln, Glu, and Ala
$X_5$ is selected from Thr, Lys, and Asn
$X_6$ is selected from Lys, Asn, and Glu
$X_7$ is selected from Asn, Thr, Ile, His, Asp, and Ala.

In certain embodiments, the insertion peptide of Formula 1a comprises an amino acid sequence selected from QADTTKN (SEQ ID NO:13), ISDQTKH (SEQ ID NO:14), ASDSTKA (SEQ ID NO:15), NQDYTKT (SEQ NO:16), HDITKNI (SEQ ID NO:17), HPDTTKN (SEQ ID NO:18), HQDTTKN (SEQ ID NO:19), NKTTNKD (SEQ ID NO:20), ISNENEH (SEQ ID NO:21), and QANANEN (SEQ ID NO:22).

In other aspects, an insertion peptide can be a peptide of 7 to 10 amino a acids in length, of Formula 1b:

$$Y_1Y_2X_1X_2X_3X_4X_5X_6X_7Y_3$$

Where each of $Y_1$-$Y_3$, if present, is independently selected from Ala, Leu, Gly, Ser, Thr, Pro
$X_1$ is selected from Gln, Asn, His, and Ile
$X_2$ is selected from Ala, Gin, Asp, and Ser
$X_3$ is selected from Asp and Ile
$X_4$ is selected from Thr, Tyr, and Gln
$X_5$ is selected from Thr and Lys
$X_6$ is selected from Lys and Asn
$X_7$ is selected from Asn, Thr, Ile, and His In certain embodiments, the insertion peptide of Formula 1b comprises an amino acid sequence selected from QADTTKN (SEQ ID NO:13), ISDQTKH (SEQ ID NO:14), NQDYTKT (SEQ NO:16), HDITKNI (SEQ ID NO:17), and HQDTTKN (SEQ ID NO:19).

In other aspects, an insertion peptide can be a peptide of 7 to 10 amino acids in length, of Formula 1c $$Y_1Y_2X_1X_2AspX_3ThrLysX_4Y_3$$

Where each of $Y_1$-$Y_3$, if present, is independently selected from Ala, Leu, Gly, Ser, Thr, Pro
$X_1$ is selected from Gln, Asn, His, and Ile
$X_2$ is selected from Ala, Gln, and Ser
$X_3$ is selected from Thr, Tyr, and Gln
$X_4$ is selected from Asn, Thr, and His In certain embodiments, the insertion peptide of Formula 1c comprises an amino acid sequence selected from QADTTKN (SEQ ID NO:13), ISDQTKH (SEQ ID NO:14), NQDYTKT (SEQ NO:16), and HQDTTKN (SEQ 1D NO:19).

In other aspects, an insertion peptide can be a peptide of 7 to 10 amino acids in length, of Formula 1d:

$$Y_1Y_2X_1X_2AspX_3ThrX_4Y_3$$

Where each of $Y_1$-$Y_3$, if present, is independently selected from Ala, Leu, Gly, Ser, Thr, Pro
$X_1$ is selected from Gln and Ile
$X_2$ is selected from Ala and Ser
$X_3$ is selected from Thr and Gln
$X_4$ is selected from Asn and His In certain embodiments, the insertion peptide of Formula 1d comprises an amino acid sequence selected from QADTTKN (SEQ ID NO:13) and ISDQTKH (SEQ ID NO:14).

In other aspects, an insertion peptide can be a peptide of 7 to 11 amino acids in length, of Formula Ie $$Y_1Y_2X_1X_2AsnX_3AsnGluX_4Y_3$$

Where each of $Y_1$-$Y_3$, if present, is independently selected from Ala, Leu, Gly, Ser, Thr, Pro
$X_1$ is selected from Gln and Ile
$X_2$ is selected from Ala and Ser
$X_3$ is selected from Glu and Ala
$X_4$ is selected from Asn and His In other embodiments, an insertion peptide of Formula 1e comprises an amino acid sequence selected from ISNENEH (SEQ ID NO:21), and QANANEN (SEQ ID NO:22).

In yet another embodiment, an insertion peptide can be a peptide of 7 to 11 amino acids in length, of Formula IIa:

$$Y_1Y_2X_1X_2DX_3TKX_4Y_3.$$

Wherein each of $Y_1$-$Y_3$, if present, is independently selected from Ala, Leu, Gly, Ser, Thr, Pro
$X_1$ is selected from Q, N, A, H, and I;
$X_2$ is selected from Q, A, P, and S;
$X_3$ is selected from T, Y, S, and Q; and
$X_4$ is selected from T, N, A, and H.

In a further embodiment of a peptide insertion of an amino acid sequence of the formula $X_1X_2DX_3TKX_4$, the peptide insertion is selected from the group consisting of QADTTKN (SEQ ID NO:13), ISDQTKH (SEQ ID NO:14), ASDSTKA, NQDYTKT (SEQ NO:16), HQDTTKN (SEQ ID NO:19), and HPDTTKN (SEQ ID NO:18).

In some such embodiments, an insertion peptide can be a peptide of 7 to 11 amino acids in length, of Formula IIb:

$$Y_1Y_2X_1X_2DX_3TKX_4Y_3$$

Wherein each of $Y_1$-$Y_3$, if present, is independently selected from Ala, Leu, Gly, Ser, Thr, Pro
$X_1$ is selected from N, A, and H;
$X_2$ is selected from Q, P, and S;
$X_3$ is selected from T, Y, and S; and
$X_4$ is selected from T, N, and A.

In a further embodiment of a peptide insertion of an amino acid sequence of the formula $X_1X_2DX_3TKX_4$, the peptide insertion is selected from the group consisting of ASDSTKA, NQDYTKT (SEQ NO:16), HQDTTKN (SEQ ID NO:19), and HPDTTKN (SEQ ID NO:18).

In other embodiments, the insertion peptide comprises an amino acid sequence selected from KDRAPST (SEQ ID NO:26), TNRTSPD (SEQ ID NO:24), PNSTHGS (SEQ ID NO:25) and GKSKVID (SEQ ID NO:23).

In some embodiments, the insertion peptide comprises an amino acid sequence selected from ASDSTKA (SEQ ID NO:15), QANANEN (SEQ ID NO:22), QADTTKN (SEQ ID NO:13), ISDQTKH (SEQ ID NO:14), NQDYTKT (SEQ ID NO:16), HDITKNI (SEQ ID NO:17), HPDTTKN (SEQ ID NO:18), HQDTTKN (SEQ ID NO:19), NKTTNKD (SEQ ID NO:20), ISNENEH (SEQ ID NO:21), GKSKVID (SEQ ID NO:23), TNRTSPD (SEQ ID NO:24), PNSTHGS (SEQ ID NO:25) and KDRAPST (SEQ ID NO:26).

In other preferred embodiments, the insertion peptide has from 1 to 3 spacer amino acids ($Y_1$-$Y_3$) at the amino and/or carboxyl terminus of an amino acid sequence selected from QADTTKN (SEQ ID NO:13), ISDQTKH (SEQ ID NO:14), ASDSTKA (SEQ ID NO:15), NQDYTKT (SEQ ID NO:16), HDITKNI (SEQ ID NO:17), HPDTTKN (SEQ ID NO:18), HQDTTKN (SEQ ID NO:19), NKTTNKD (SEQ ID NO:20), ISNENEH (SEQ ID NO:21), QANANEN (SEQ ID NO:22), GKSKVID (SEQ ID NO:23), TNRTSPD (SEQ ID NO:24), PNSTHGS (SEQ ID NO:25) and KDRAPST (SEQ ID NO:26). In certain such embodiments, the insertion peptide is selected from the group consisting of: LAQADTTKNA (SEQ ID NO:27), LAISDQTKHA (SEQ ID NO:28), LGISDQTKHA (SEQ ID NO:29), LAASDSTKAA (SEQ ID NO:30), LANQDYTKTA (SEQ ID NO:31), LAHDITKNIA (SEQ ID NO:32), LAHPDTTKNA (SEQ ID NO:33), LAHQDTTKNA (SEQ ID NO:34), LANKTTNKDA (SEQ ID NO:35), LPISNENEHA (SEQ ID NO:36), LPQANANENA (SEQ ID NO:37), LAGKSKVIDA (SEQ ID NO:38), LATNRTSPDA (SEQ ID NO:39), LAPNSTHGSA (SEQ ID NO:40) and LAKDRAPSTA (SEQ ID NO:41).

In some embodiments, the subject variant AAV capsid protein does not include any other amino acid sequence modifications other than a peptide insertion of from about 5 amino acids to about 20 amino acids in the GH loop, or loop IV. For example, in some embodiments, the subject variant AAV capsid protein comprises a peptide insertion comprising an amino acid sequence selected from the group consisting of QADTTKN (SEQ ID NO:13), ISDQTKH (SEQ ID NO:14), ASDSTKA (SEQ ID NO:15), NQDYTKT (SEQ ID NO:16), HDITKNI (SEQ ID NO:17), HPDTTKN (SEQ ID NO:18) HQDTTKN (SEQ ID NO:19), NKTTNKD (SEQ ID NO:20), ISNENEH (SEQ ID NO:21), QANANEN (SEQ ID NO:22), GKSKVID (SEQ ID NO:23), TNRTSPD (SEQ ID NO:24), PNSTHGS (SEQ ID NO:25), KDRAPST (SEQ ID NO:26), LAQADTTKNA (SEQ ID NO:27), LAISDQTKHA (SEQ ID NO:28), LGISDQTKHA (SEQ ID NO:29), LAASDSTKAA (SEQ ID NO:30), LANQDYTKTA (SEQ ID NO:31), LAHDITKNIA (SEQ ID NO:32), LAHPDTTKNA (SEQ ID NO:33), LAHQDTTKNA (SEQ ID NO:34), LANKTTNKDA (SEQ ID NO:35), LPISNENEHA (SEQ ID NO:36), LPQANANENA (SEQ ID NO:37), LAGKSKVIDA (SEQ ID NO:38), LATNRTSPDA (SEQ ID NO:39), LAPNSTHGSA (SEQ ID NO:40) and LAKDRAPSTA (SEQ ID NO:41), and the variant AAV capsid does not include any other amino acid substitutions, insertions, or deletions (i.e., the variant AAV capsid protein comprises said insertion and is otherwise identical to the corresponding AAV capsid protein). Put another way, the variant AAV capsid protein comprising said insertion is otherwise identical to the parental AAV capsid protein into which the peptide has been inserted. As another example, the subject variant AAV capsid protein comprises a peptide insertion having an amino acid sequence selected from QADTTKN (SEQ ID NO:13), ISDQTKH (SEQ ID NO:14), ASDSTKA (SEQ ID NO:15), NQDYTKT (SEQ ID NO:16), HDITKNI (SEQ ID NO:17), HPDTTKN (SEQ ID NO:18), HQDTTKN (SEQ ID NO:19), NKTTNKD (SEQ ID NO:20), ISNENEH (SEQ ID NO:21), QANANEN (SEQ ID NO:22), GKSKVID (SEQ ID NO:23), TNRTSPD (SEQ ID NO:24), PNSTHGS (SEQ ID NO:25) and KDRAPST (SEQ ID NO:26), LAQADTTKNA (SEQ ID NO:27), LAISDQTKHA (SEQ ID NO:28), LGISDQTKHA (SEQ ID NO:29), LAASDSTKAA (SEQ ID NO:30), LANQDYTKTA (SEQ ID NO:31), LAHDITKNIA (SEQ ID NO:32), LAHPDTTKNA (SEQ ID NO:33), LAHQDTTKNA (SEQ ID NO:34), LANKTTNKDA (SEQ ID NO:35), LPISNENEHA (SEQ ID NO:36), LPQANANENA (SEQ ID NO:37), LAGKSKVIDA (SEQ ID NO:38), LATNRTSPDA (SEQ ID NO:39), LAPNSTHGSA (SEQ ID NO:40) and LAKDRAPSTA (SEQ ID NO:41), wherein the peptide insertion is located between amino acids 587 and 588 of the VP1 of the AAV2 capsid or the corresponding amino acids of a VP1 of another parental AAV, e.g. between amino acids 588 and 589 of VP1 of AAV1, AAV3A, AAV3B, AAV6 or AAV9, between amino acids 586 and 587 of VP1 of AAV4, between amino acids 577 and 578 of VP1 of AAV5, between amino acids 589 and 590 of VP1 of AAV7, between amino acids 590 to 591 of VP1 of AAV8 or AAV10, etc. wherein the variant AAV capsid protein sequence is otherwise identical to the corresponding parental AAV capsid protein sequence, e.g. any one of SEQ ID NOs:1-12.

In other embodiments, the subject variant AAV capsid protein, in addition to comprising a peptide insertion, e.g. as disclosed herein or as known in the art, in the GH loop, comprises from about 1 to about 100 amino acid substitutions or deletions, e.g. 1 to about 5, from about 2 to about 4, from about 2 to about 5, from about 5 to about 10, from about 10 to about 15, from about 15 to about 20, from about 20 to about 25, from about 25-50, from about 50-100 amino acid substitutions or deletions compared to the parental AAV capsid protein. Thus, in some embodiments, a subject variant capsid protein comprises an amino acid sequence having a sequence identity of 85% or more, 90% or more, 95% or more, or 98% or more, e.g. or 99% identity to the corresponding parental AAV capsid, e.g. a wild type capsid protein as set forth in SEQ ID NOs:1-12.

In a further embodiment, the one or more amino acid substitutions are at amino acid residue(s) 1, 15, 34, 57, 66, 81, 101, 109, 144, 164, 176, 188, 196, 226, 236, 240, 250, 312, 363, 368, 449, 456, 463, 472, 484, 524, 535, 551, 593, 698, 708, 719, 721, and/or 735 of AAV2 VP1 capsid protein as numbered prior to insertion of the peptide, or the corresponding amino acid residue(s) of another AAV capsid protein. In some such embodiments, the one or more amino acid substitutions are selected from the group consisting of M1L, L15P, P34A, N57D, N66K, R81Q, Q101R, S109T, R144K, R144M, Q164K, T176P, L188I, S196Y, G226E, G236V, I240T, P250S, N312K, P363L, D368H, N449D, T456K, S463Y, D472N, R484C, A524T, P535S, N551S, A593E, I698V, V708I, V719M, S721L, and L735Q of AAV2 VP1 capsid protein as numbered prior to the insertion of the peptide, or the corresponding amino acid residue(s) of another AAV capsid protein.

In a preferred embodiment, a variant AAV capsid protein is provided comprising a) a peptide insertion in the GH-loop of the capsid protein, wherein the peptide insertion comprises an amino acid sequence selected from ISDQTKH (SEQ ID NO:14), LGISDQTKHA (SEQ ID NO:29) and LAISDQTKHA (SEQ ID NO:28), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: M1L, L15P, P34A, N57D, N66K, R81Q, Q101R, S109T, R144K, R144M, Q164K, T176P, 188I, S196Y, G226E, G236V, I240T, P250S, N312K, P363L, D368H, N449D, T456K, S463Y, D472N, R484C, A524T, P535S, N551S, A593E, I698V, V708I, V719M, S721L, L735Q and a combination thereof. In some embodiments, the one or more amino acid substitutions are selected from the group consisting of: M1L+L15P+P535S, P34A, P34A+S721L, N57D, N66K, R81Q, Q101R, S109T, R144K, R144M, Q164K, Q164K+V708I, T176P, L188I, S196Y, G226E, G236V, I240T, N312K, N312K+N449D+D472N+N551S+I698V+L735Q, P363L, R484C+V708I, T456K and V708I. Preferably, the peptide insertion site is located between amino acids 587 and 588 of AAV2 capsid or the corresponding position in the capsid protein of another AAV serotype.

In a particularly preferred embodiment, the variant AAV capsid comprises a peptide insertion comprising the amino acid sequence ISDQTKH (SEQ ID NO:14) or comprising, consisting essentially of, or consisting of the amino acid sequence LAISDQTKHA (SEQ ID NO:28) or LGISDQTKHA (SEQ ID NO:29) between amino acids 587 and 588 of VP1 of AAV2 or the corresponding amino acids of another AAV capsid, and further comprises a P34A amino acid substitution at residue 34 relative to the amino acid sequence of AAV2 capsid (SEQ ID NO:2) or the corresponding residue of another AAV capsid. The variant AAV capsid may have at least about 85%, at least about 90%, at least about 95%, at least about 98%, or at least about 99%, or greater, amino acid sequence identity to the entire length of the amino acid sequence set forth in SEQ ID NO:2 or the corresponding parental AAV capsid. In a particularly preferred embodiment, the variant AAV capsid has an amino acid sequence having at least about 85%, at least about 90%, at least about 95%, at least about 98% sequence identity to or is 100% identical to the following amino acid sequence:

(SEQ ID NO: 42)
MAADGYLPDWLEDTLSEGIRQWWKLKPGPPPPKAAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYNTSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLAISDQTKHARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL

In another particularly preferred embodiment, the variant AAV capsid comprises a peptide insertion comprising the amino acid sequence ISDQTKH (SEQ ID NO:14) or comprising, consisting essentially of, or consisting of the amino acid sequence LAISDQTKHA (SEQ ID NO:28) or LGISDQTKHA (SEQ ID NO:29) between amino acids 587 and 588 of AAV2 capsid protein or the corresponding position in the capsid protein of another AAV serotype and comprises an N312K amino acid substitution compared to the amino acid sequence of AAV2 capsid (SEQ ID NO:2) or the corresponding substitution in another AAV parental serotype and optionally further comprises N449D, D472N, N551S, I698V and/or L735Q amino acid substitutions compared to the amino acid sequence of AAV2 capsid or the corresponding substitutions in another AAV parental serotype. In another particularly preferred embodiment, the variant AAV capsid comprises a peptide insertion comprising the amino acid sequence ISDQTKH (SEQ ID NO:14) or comprising, consisting essentially of, or consisting of the amino acid sequence LAISDQTKHA (SEQ ID NO:28) or LGISDQTKHA (SEQ ID NO:29) between amino acids 587 and 588 of AAV2 capsid or the corresponding position in the capsid protein of another AAV serotype and comprises N312K, N449D, D472N, N551S, I698V and L735Q amino acid substitutions compared to the amino acid sequence of AAV2 capsid (SEQ ID NO:2) or substitutions at the corresponding residues in another AAV parental serotype. The variant AAV capsid may have at least about 85%, at least about 90%, at least about 95%, at least about 98%, or greater, amino acid sequence identity to the entire length of the amino acid sequence set forth in SEQ ID NO:2. In a particularly preferred embodiment, the variant AAV capsid has an amino acid sequence having at least about 85%, at least about 90%, at least about 95%, at least about 98% sequence identity to or is 100% identical to the following amino acid sequence:

(SEQ ID NO: 43)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLKFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTDT

PSGTTTQSRLQFSQAGASDIRNQSRNWLPGPCYRQQRVSKTSADNNNSEY

SWTGATKYHLNGRDSLVNPGPAMASHKDDEEKFFPQSGVLIFGKQGSEKT

SVDIEKVMITDEEEIRTTNPVATEQYGSVSTNLQRGNLAISDQTKHARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEVQYTSNYNKSVNVDFTVDTNGVYSEPRPIGTRYLTRNQ

In another embodiment, a variant AAV capsid protein is provided comprising a) a peptide insertion located between amino acids 588 and 589 of VP1 of AAV1, AAV3A, AAV3B, AAV6 or AAV9, amino acids 586 and 587 of AAV4, amino acids 577 and 578 of AAV5, amino acids 589 and 590 of AAV7, or amino acids 590 to 591 of AAV8 or AAV10, the peptide insertion comprising an amino acid sequence selected from ISDQTKH (SEQ ID NO:14), LGISDQTKHA (SEQ ID NO:29) and LAISDQTKHA (SEQ ID NO:28), and b) a valine to isoleucine substitution at amino acid 709 of AAV3A or AAV3B, an alanine to isoleucine substitution at position 709 of AAV1 or AAV6, an asparagine to isoleucine substitution at amino acid 707 of AAV4 or amino acid 709 of AAV9 or a threonine to isoleucine substitution at amino acid 710 of AAV7 or amino acid 711 of AAV8 or AAV10 or a glutamine to isoleucine substitution at amino acid 697 of AAV5 and is optionally otherwise identical to any one of SEQ ID NOs: 1 and 3-12. In preferred embodiments, the variant capsid protein comprises a) a peptide insertion comprising the amino acid sequence ISDQTKH (SEQ ID NO:14) or comprising, consisting essentially of, or consisting of the amino acid sequence LAISDQTKHA (SEQ ID NO:28) or LGISDQTKHA (SEQ ID NO:29) between amino acids 587 and 588 of AAV2 capsid and b) a valine to isoleucine amino acid substitution at amino acid 708 compared to the amino acid sequence of AAV2, wherein the variant capsid protein comprises from 2 to 5, from 5 to 10, or from 10 to 15 amino acid substitutions.

In yet another embodiment, the variant capsid protein comprises a) a peptide insertion comprising the amino acid sequence ISDQTKH (SEQ ID NO:14) or comprising, consisting essentially of, or consisting of the amino acid sequence LAISDQTKHA (SEQ ID NO:28) or LGISDQTKHA (SEQ ID NO:29) between amino acids 587 and 588 of AAV2 capsid and b) a valine to isoleucine amino acid substitution at amino acid 708 compared to the amino acid sequence of AAV2 and is otherwise identical to the amino acid sequence of SEQ ID NO:2.

In yet another embodiment, the variant capsid protein comprises a) a peptide insertion comprising the amino acid sequence ISDQTKH (SEQ ID NO:14) or comprising, consisting essentially of, or consisting of the amino acid sequence LAISDQTKHA (SEQ ID NO:28) or LGISDQTKHA (SEQ ID NO:29) between amino acids 587 and 588 of AAV2 capsid and is otherwise identical to the amino acid sequence of SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 44)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGGKKRPVEHS

PVEPDSSSGTGKAGQQPARKRLNFGQTGDADSVPDPQPLGQPPAAPSGLG

TNTMATGSGAPMADNNEGADGVGNSSGNWHCDSTWMGDRVITTSTRTWAL

PTYNNHLYKQISSQSGASNDNHYFGYSTFWGYFDFNRFHCHFSPRDWQRL

INNNWGFRPKRLNFKLFNIQVKEVTQNDGTTTIANNLTSTVQVFTDSEYQ

LPYVLGSAHQGCLPPFPADVFMVPQYGYLTINNGSQAVGRSSFYCLEYFP

SQMLRTGNNFTFSYTFEDVPFHSSYAHSQSLDRLMNPLIDQYLYYLSRTN

TPSGTTTQSRLQFSQAGASDIRDQSRNWLPGPCYRQQRVSKTSADNNNSE

YSWTGATKYHLNGRDSLVNPGPAMASHKDDEEKFFPQSGVLIFGKQGSEK

TNVDIEKVMITDEEEIRTTNPVATEQYGSVSTNLQRGNLGISDQTKHARQ

AATADVNTQGVLGPGMVWQDRDVYLQGPIWAKIPHTDGHFHPSPLMGGFG

LKHPPPQILIKNTPVPANPSTTFSAAKFASFITQYSTGQVSVEIEWELQK

ENSKRWNPEIQYTSNYNKSVNVDFTVDTNGVYSEPRPIGTRYLTRNL

In a preferred embodiment, a variant AAV capsid protein is provided comprising a) a peptide insertion in the GH-loop of the capsid protein, wherein the peptide insertion comprises an amino acid sequence selected from QADTTKN (SEQ ID NO:13) and LAQADTTKNA (SEQ ID NO:27), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: M1L, L15P, P34A, N57D, N66K, R81Q, Q101R, S109T, R144K, R144M, Q164K, T176P, L188I, S196Y, G226E, G236V, I240T, P250S, N312K, P363L, D368H, N449D, T456K, S463Y, D472N, R484C, A524T, P535S, N551S, A593E, I698V, V719M, S721L, L735Q and a combination thereof, preferably selected from S109T, P250S, A524T, A593E, I698V, V708I, and/or V719M. The peptide insertion site is preferably located between amino acids 587 and 588 of AAV2 capsid or the corresponding position in the capsid protein of another AAV serotype. In a particularly preferred embodiment, the variant AAV capsid comprises a peptide insertion comprising the amino acid sequence QADTTKN (SEQ ID NO:13) or comprising, consisting essentially of, or consisting of the amino acid sequence LAQADTTKNA (SEQ ID NO:27) between amino acids 587 and 588 of AAV2 capsid or the corresponding position in the capsid protein of another AAV serotype and comprises an I698V amino acid substitution compared to the amino acid sequence of AAV2 or the corresponding substitution in another AAV parental serotype, wherein the substituted amino acid(s) do not naturally occur at the corresponding position. The variant AAV capsid may have at least about 85%, at least about 90%, at least about 95%, at least about 98%, or greater, amino acid sequence identity to the entire length of the amino acid sequence set forth in SEQ ID NO:2. In some embodiments, the corresponding amino acid substitution is an I699V amino acid substitution compared to the amino acid sequence of AAV3A, AAV3B or AAV9 capsid, an I687V substitution compared to the amino acid sequence of AAV5 capsid, an I700V substitution compared to the amino acid sequence of AAV7, an I701V substitution compared to the amino acid sequence of AAV8 or AAV10. In a particularly preferred embodiment, the variant AAV capsid has an amino acid sequence having at least about 85%, at least about 90%, at least about 95%, at least about 98% sequence identity to or is 100% identical to the following amino acid sequence:

(SEQ ID NO: 45)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

-continued

NVDIEKVMITDEEEIRTTNPVATEQYGSVSTNLQRGNLAQADTTKNARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEVQYTSNYNKSVNVDFTVDTNGVYSEPRPIGTRYLTRNL

In other preferred embodiments, the variant AAV capsid comprises a peptide insertion comprising the amino acid sequence QADTTKN (SEQ ID NO:13) or comprising, consisting essentially of, or consisting of the amino acid sequence LAQADTTKNA (SEQ ID NO:27) between amino acids 587 and 588 of AAV2 capsid or the corresponding position in the capsid protein of another AAV serotype and comprises a V719M amino acid substitution and optionally a V708I substitution compared to the amino acid sequence of AAV2 or the corresponding substitution in another AAV parental serotype, wherein the substituted amino acid(s) do not naturally occur at the corresponding position.

In another embodiment, a variant AAV capsid protein is provided comprising a) a peptide insertion located between amino acids 588 and 589 of VP1 of AAV1, AAV3A, AAV3B, AAV6 or AAV9, amino acids 586 and 587 of AAV4, amino acids 577 and 578 of AAV5, amino acids 589 and 590 of AAV7, or amino acids 590 to 591 of AAV8 or AAV10, the peptide insertion comprising an amino acid sequence selected from QADTTKN (SEQ ID NO:13) and LAQADTTKNA (SEQ ID NO:27), and b) a valine to isoleucine substitution at amino acid 709 of AAV3A or AAV3B, an alanine to isoleucine substitution at position 709 of AAV1 or AAV6, an asparagine to isoleucine substitution at amino acid 707 of AAV4 or amino acid 709 of AAV9 or a threonine to isoleucine substitution at amino acid 710 of AAV7 or amino acid 711 of AAV8 or AAV10 or a glutamine to isoleucine substitution at amino acid 697 of AAV5. In another embodiment, a variant AAV capsid protein is provided comprising a) a peptide insertion located between amino acids 588 and 589 of VP1 of AAV1, AAV3A, AAV3B, AAV6 or AAV9, amino acids 586 and 587 of AAV4, amino acids 577 and 578 of AAV5, amino acids 589 and 590 of AAV7, or amino acids 590 to 591 of AAV8 or AAV10, the peptide insertion comprising an amino acid sequence selected from QADTTKN (SEQ ID NO:13) and LAQADTTKNA (SEQ ID NO:27), and b) a serine to threonine amino acid substitution at position 109 compared to the amino acid sequence of AAV1, AAV3A, AAV3B, AAV4, AAV7, AAV8, AAV9, or AAV10 or at position 108 compared to the amino acid sequence of AAV5 or AAV6. In preferred embodiments, the variant AAV capsid comprises a peptide insertion comprising the amino acid sequence QADTTKN (SEQ ID NO:13) or comprising, consisting essentially of, or consisting of the amino acid sequence LAQADTTKNA (SEQ ID NO:27) between amino acids 587 and 588 of AAV2 capsid and comprises a serine to threonine substitution at amino acid 109 (S109T) or a valine to isoleucine amino acid substitution at amino acid 708 (V708I) compared to the amino acid sequence of AAV2, wherein the variant capsid protein comprises from 1 to 5, from 5 to 10, or from 10 to 15 amino acid substitutions and is preferably at least about 85%, at least about 90%, at least about 95%, at least about 98%, or greater amino acid sequence identity to the entire length of the amino acid sequence set forth in SEQ ID NO:2. In other preferred embodiments, the variant AAV capsid comprises a peptide insertion comprising the amino acid sequence QADTTKN (SEQ ID NO:13) or comprising, consisting essentially of, or consisting of the amino acid sequence LAQADTTKNA (SEQ ID NO:27) between amino acids 587 and 588 of AAV2 capsid or the corresponding position in the capsid protein of another AAV serotype and comprises a serine to threonine substitution at amino acid 109 and a valine to isoleucine amino acid substitution at amino acid 708 compared to the amino acid sequence of AAV2.

In yet another embodiment, the variant capsid protein comprises a) a peptide insertion comprising the amino acid sequence QADTTKN (SEQ ID NO:13) or comprising, consisting essentially of, or consisting of the amino acid sequence LAQADTTKNA (SEQ ID NO:27) between amino acids 587 and 588 of AAV2 capsid and b) at least one amino acid substitution, wherein the amino acid sequence of the variant capsid does not comprise a valine to isoleucine amino acid substitution at amino acid 708 compared to the amino acid sequence of AAV2 and does not comprise a serine to threonine substitution at amino acid 109 compared to the amino acid sequence of AAV2.

In yet another embodiment, the variant capsid protein comprises a) a peptide insertion comprising the amino acid sequence QADTTKN (SEQ ID NO:13) or comprising, consisting essentially of, or consisting of the amino acid sequence LAQADTTKNA (SEQ ID NO:27) between amino acids 587 and 588 of AAV2 capsid and is otherwise identical to the amino acid sequence of SEQ ID NO:2.

In another preferred embodiment, a variant AAV capsid protein is provided comprising a) a peptide insertion in the GH-loop of the capsid protein, wherein the peptide insertion comprises an amino acid sequence selected from HDITKNI (SEQ ID NO:17), IAHDITKNIA (SEQ ID NO:60) and LAHDITKNIA (SEQ ID NO:32), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: M1L, L15P, P34A, N57D, N66K, R81Q, Q101R, S109T, R144K, R144M, Q164K, T176P, L188I, S196Y, G226E, G236V, I240T, P250S, N312K, P363L, D368H, R389S, N449D, T456K, S463Y, D472N, R484C, A524T, P535S, N551S, A593E, I698V, V708I, V719M, S721L, L735Q and a combination thereof. In some embodiments, the AAV capsid protein comprises one or more amino acid substitutions selected from S109T, R389S, A593E and/or V708I. Preferably, the peptide insertion site is located between amino acids 587 and 588 of AAV2 capsid or the corresponding position in the capsid protein of another AAV serotype. In one preferred embodiment, the variant AAV capsid comprises a peptide insertion comprising the amino acid sequence HDITKNI (SEQ ID NO:17) or comprising, consisting essentially of, or consisting of the amino acid sequence IAHDITKNIA (SEQ ID NO:60) or LAHDITKNIA (SEQ ID NO:32) between amino acids 587 and 588 of AAV2 capsid and comprises an S109T amino acid substitution compared to the amino acid sequence of AAV2 capsid or the corresponding substitution in another AAV parental serotype. The variant AAV capsid may have at least about 85%, at least about 90%, at least about 95%, at least about 98%, or greater amino acid sequence identity to the entire length of the amino acid sequence set forth in SEQ ID NO:2.

In yet another embodiment, the variant capsid comprises a) a peptide insertion comprising the amino acid sequence HDITKNI (SEQ ID NO:17) or comprising, consisting essentially of, or consisting of the amino acid sequence IAHDITKNIA (SEQ ID NO:60) or LAHDITKNIA (SEQ ID NO:32) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 46)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPRAAPSGLGT

NTMATGSGAPNIADNNEGADGVGNSSGNWHCDSTWMGDRVITTSTRTWAL

PTYNNHLYKQISSQSGASNDNHYFGYSTPWGYFDFNRFHCHFSPRDWQRL

INNNWGFRPKRLNFKLFNIQVKEVTQNDGTTTIANNLTSTVQVFTDSEYQ

LPYVLGSAHQGCLPPFPADVFMVPQYGYLTLNNGSQAVGRSSFYCLEYFP

SQMLRTGNNFTFSYTFEDVPFHSSYAHSQSLDRLMNPLIDQYLYYLSRTN

TPSGTTTQSRLQFSQAGASDIRDQSRNWLPGPCYRQQRVSKTSADNNNSE

YSWTGATKYHLNGRDSLVNPGPAMASHKDDEEKFFPQSGVLIFGKQGSEK

TNVDIEKVMITDEEEIRTTNPVATEQYGSVSTNLQRGNLAHDITKNIARQ

AATADVNTQGVLPGMVWQDRDVYLQGPIWAKIPHTDGHFHPSPLMGGFGL

KHPPPQILIKNTPVPANPSTTFSAAKFASFITQYSTGQVSVEIEWELQKE

NSKRWNPEIQYTSNYNKSVNVDFTVDTNGVYSEPRPIGTRYLTRNL

In other embodiments, the variant capsid comprises a) a peptide insertion comprising, consisting essentially of, or consisting of the amino acid sequence LAHDITKNIA between amino acids 587 and 588 of AAV2 capsid and b) at least one amino acid substitution, wherein the amino acid sequence of the variant capsid does not comprise a valine to isoleucine amino acid substitution at amino acid 708 compared to the amino acid sequence of AAV2. In yet other embodiments, the variant capsid comprises a) a peptide insertion comprising the amino acid sequence DITKNIA (SEQ ID NO:61) or comprising, consisting essentially of or consisting of the amino acid sequence IAHDITKNIA (SEQ ID NO:60) or LAHDITKNIA (SEQ ID NO:32) between amino acids 587 and 588 of AAV2 capsid and b) a V708I substitution compared to the amino acid sequence of AAV2. In other embodiments, the variant capsid comprises a) a peptide insertion comprising, consisting essentially of, or consisting of the amino acid sequence LAHDITKNIA (SEQ ID NO:32) between amino acids 587 and 588 of AAV2 capsid and b) two or more amino acid substitutions, wherein the amino acid sequence of the variant capsid comprises a valine to isoleucine amino acid substitution at amino acid 708 compared to the amino acid sequence of AAV2.

In another preferred embodiment, a variant AAV capsid protein is provided comprising a) a peptide insertion in the GH-loop of the capsid protein, wherein the peptide insertion comprises an amino acid sequence selected from NQDYTKT (SEQ ID NO:16) and LANQDYTKTA (SEQ ID NO:31), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: M1L, L15P, P34A, N57D, N66K, R81Q, Q101R, S109T, R144K, R144M, Q164K, T176P, L188I, S196Y, G226E, G236V, I240T, P250S, P363L, D368H, N449D, T456K, S463Y, D472N, R484C, A524T, P535S, N551S, A593E, I698V, V708I, V719M, S721L, L735Q and a combination thereof. In some embodiments, the AAV capsid protein comprises one or more amino acid substitutions selected from S109T, S109T+S463Y, D368H and V708I. Preferably, the peptide insertion site is located between amino acids 587 and 588 of AAV2 capsid or the corresponding position in the capsid protein of another AAV serotype. In one preferred embodiment, the variant AAV capsid comprises a peptide insertion comprising the amino acid sequence NQDYTKT (SEQ ID NO:16) or comprising, consisting essentially of, or consisting of the amino acid sequence LANQDYTKTA (SEQ ID NO:31) between amino acids 587 and 588 of AAV2 capsid and comprises a V708I amino acid substitution compared to the amino acid sequence of AAV2 capsid or the corresponding substitution in another AAV parental serotype. The variant AAV capsid may have at least about 85%, at least about 90%, at least about 95%, at least about 98%, or greater amino acid sequence identity to the entire length of the amino acid sequence set forth in SEQ ID NO:2. In yet another embodiment, the variant capsid comprises a) a peptide insertion comprising the amino acid sequence NQDYTKT (SEQ ID NO:16) or comprising, consisting essentially of, or consisting of the amino acid sequence LANQDYTKTA (SEQ ID NO:31) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 47)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLANQDYTKTARQA

ATADVNTQGVLPGMVWQDRDVYLQGPIWAKIPHTDGHFHPSPLMGGFGLK

HPPPQILIKNTPVPANPSTTFSAAKFASFITQYSIGQVSVEIEWELQKEN

SKRWNPEIQYTSNYNKSVNVDFTVDTNGVYSEPRPIGTRYLTRNI

In other embodiments, the variant capsid comprises a) a peptide insertion comprising the amino acid sequence NQDYTKT (SEQ ID NO:16) or comprising, consisting essentially of, or consisting of the amino acid sequence LANQDYTKTA (SEQ ID NO:31) between amino acids 587 and 588 of AAV2 capsid and b) an S109T amino acid substitution compared to the sequence of SEQ ID NO:2 and optionally an S463Y amino acid substitution, wherein the variant capsid is at least about 85%, at least about 90%, at least about 95%, at least about 98% identical to the entire length of the amino acid sequence set forth in SEQ ID NO:2. In related embodiments, the variant capsid comprises a) a peptide insertion comprising the amino acid sequence NQDYTKT (SEQ ID NO:16) or comprising, consisting essentially of, or consisting of the amino acid sequence LANQDYTKTA (SEQ ID NO:31) between amino acids 587 and 588 of AAV2 capsid and b) an S109T amino acid substitution compared to the amino acid sequence of SEQ ID NO:2 and is otherwise identical to the amino acid sequence of SEQ ID NO:2.

In another embodiment, a variant AAV capsid protein is provided comprising a) a peptide insertion located between amino acids 588 and 589 of VP1 of AAV1, AAV3A, AAV3B, AAV6 or AAV9, amino acids 586 and 587 of AAV4, amino acids 577 and 578 of AAV5, amino acids 589 and 590 of AAV7, or amino acids 590 to 591 of AAV8 or AAV10, the peptide insertion comprising an amino acid sequence selected from NQDYTKT (SEQ ID NO:16) and LANQDYTKTA (SEQ ID NO:31), and b) an asparagine to lysine amino acid substitution at position 313 compared to the amino acid sequence of AAV1 or AAV6, or at position 314 compared to the amino acid sequence of AAV9, or a serine to lysine substitution at position 312 of AAV3A or AAV3B or at position 315 of AAV8 or AAV10, or an arginine to lysine substitution at position 303 of AAV4 or AAV5, or at position 314 of AAV7. In another embodiment, the variant capsid comprises a) a peptide insertion comprising the amino acid sequence NQDYTKT (SEQ ID NO:16) or comprising, consisting essentially of or consisting of the amino acid sequence LANQDYTKTA (SEQ ID NO:31) between amino acids 587 and 588 of AAV2 capsid and b) an N312K amino acid substitution, wherein the variant capsid protein comprises from 1 to 5, from 5 to 10, or from 10 to 15 amino acid substitutions.

In another embodiment, a variant AAV capsid protein is provided comprising a) a peptide insertion in the GH-loop of the capsid protein, wherein the peptide insertion comprises an amino acid sequence selected from PNSTHGS (SEQ ID NO:25) and LAPNSTHGSA (SEQ ID NO:40), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: M1L, L15P, P34A, N57D, N66K, R81Q, Q101R, S109T, R144K, R144M, Q164K, T176P, L188I, S196Y, G226E, G236V, I240T, P250S, N312K, P363L, D368H, N449D, T456K, S463Y, D472N, R484C, A524T, P535S, N551S, A593E, I698V, V708I, V719M, S721L, L735Q and a combination thereof. Preferably, the peptide insertion site is located between amino acids 587 and 588 of AAV2 capsid or the corresponding position in the capsid protein of another AAV serotype. In one preferred embodiment, the variant AAV capsid comprises a peptide insertion comprising the amino acid sequence PNSTHGS (SEQ ID NO:25) or comprising, consisting essentially of, or consisting of the amino acid sequence LAPNSTHGSA (SEQ ID NO:40) between amino acids 587 and 588 of AAV2 capsid and comprises a V708I amino acid substitution compared to the amino acid sequence of AAV2 capsid or the corresponding substitution in another AAV parental serotype. The variant AAV capsid may have at least about 85%, at least about 90%, at least about 95%, at least about 98%, or greater amino acid sequence identity to the entire length of the amino acid sequence set forth in SEQ ID NO:2. In yet another embodiment, the variant capsid comprises a) a peptide insertion comprising the amino acid sequence PNSTHGS (SEQ ID NO:25) or comprising, consisting essentially of, or consisting of the amino acid sequence LAPNSTHGSA (SEQ ID NO:40) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

```
(SEQ ID NO: 48)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSFGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDCTTTTIANNLTSTVQVFTDSEYQLPYVLGS

AHQGCLPPFPADVFMVPQYGYLTLNNGSQAVGRSSFYCLEYFPSQMLRTGN

NFTFSYTFEDVPFHSSYAHSQSLDRLMNPLIDQYLYYLSRTNTPSGTTTQS

RLQFSQAGASDIRDQSRNWLPGPCYRQQRVSKTSADNNNSEYSWTGATKYH

LNGRDSLVNPGPAMASHKDDEEKFFPQSGVLIFGKQGSEKTNVDIEKVMIT

DEEEIRTTNPVATEQYGSVSTNLQRGNLAPNSTHGSARQAATADVNTQGVL

PGMVWQDRDVYLQGPIWAKIPHTDGHFHPSPLMGGFGLKHPPPQILIKNTP

VPANPSTTFSAAKFASFITQYSTGQVSVEIEWELQKENSKRWNPEIQYTSN

YNKSVNVDFTVDTNGVYSEPRPIGTRYLTRNL
```

In another embodiment, a variant AAV capsid protein is provided comprising a) a peptide insertion in the GH-loop of the capsid protein, wherein the peptide insertion comprises an amino acid sequence selected from NKTTNKDA (SEQ ID NO:62) and LANKTTNKDA (SEQ ID NO:35), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: M1L, L15P, P34A, N57D, N66K, R81Q, Q101R, S109T, R144K, R144M, Q164K, T176P, L188I, S196Y, G226E, G236V, I240T, P250S, N312K, P363L, D368H, N449D, T456K, S463Y, D472N, R484C, A524T, P535S, N551S, A593E, I698V, V708I, V719M, S721L, L735Q and a combination thereof. Preferably, the peptide insertion site is located between amino acids 587 and 588 of AAV2 capsid or the corresponding position in the capsid protein of another AAV serotype. In one preferred embodiment, the variant AAV capsid comprises a peptide insertion comprising the amino acid sequence NKTTNKDA (SEQ ID NO:62) or comprising, consisting essentially of, or consisting of the amino acid sequence LANKTTNKDA (SEQ ID NO:35) between amino acids 587 and 588 of AAV2 capsid and comprises an N449D amino acid substitution compared to the amino acid sequence of AAV2 capsid or the corresponding substitution in another AAV parental serotype. The variant AAV capsid may have at least about 85%, at least about 90%, at least about 95%, at least about 98%, or greater amino acid sequence identity to the entire length of the amino acid sequence set forth in SEQ ID NO:2. In yet another embodiment, the variant capsid comprises a) a peptide insertion comprising the amino acid sequence NKTTNKDA (SEQ ID NO:62) or comprising, consisting essentially of, or consisting of the amino acid sequence LANKTTNKDA (SEQ ID NO:35) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 49)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSFGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDPNRFHCHFSPRDWQRLINNNWGF

RPKRLNFKLFNIQVKEVTQNDGTTTIANNLTSTVQVFTDSEYQLPYVLGSA

HQGCLPPFPADVFMVPQYGYLTLNNGSQAVGRSSFYCLEYFPSQMLRTGNN

FTFSYTFEDVPFHSSYAHSQSLDRLMTNPLIDQYLYYLSRTNTPSGTTTQS

RLQFSQAGASDIRDQSRNWLPGPCYRQQRVSKTSADNNNSEYSWTGATKYH

LNGRDSLVNPGPAMASHKDDEEKFFPQSGVLIFGKQGSEKTNVDIEKVMIT

DEEEIRTTNPVATEQYGSVSTNLQRGNLANKTTNKDARQAATADVNTQGVL

PGMVWQDRDVYLQGPIWAKIPHTDGHFHPSPLMGGFGLKHPPPQILIKNTP

VPANPSTTFSAAKFASFITQYSTGQVSVEIEWELQKENSKRWNPEIQYTSN

YNKSVNVDFTVDTNGVYSEPRPIGTRYLTRNL

In another embodiment, a variant AAV capsid protein is provided comprising a) a peptide insertion in the GH-loop of the capsid protein, wherein the peptide insertion comprises an amino acid sequence selected from TNRTSPD (SEQ ID NO:24) and LATNRTSPDA (SEQ ID NO:39), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: M1L, L15P, P34A, N57D, N66K, R81Q, Q101R, S109T, R144K, R144M, Q164K, T176P, L188I, S196Y, G226E, G236V, I240T, P250S, N312K, P363L, D368H N449D, T456K, S463Y, D472N, R484C, A524T, P535S, N551S, A593E, I698V, V719M, S721L, L735Q and a combination thereof. Preferably, the peptide insertion site is located between amino acids 587 and 588 of AAV2 capsid or the corresponding position in the capsid protein of another AAV serotype. In a related embodiment, a variant AAV capsid protein is provided comprising a) a peptide insertion located between amino acids 588 and 589 of VP1 of AAV1, AAV3A, AAV3B, AAV6 or AAV9, amino acids 586 and 587 of AAV4, amino acids 577 and 578 of AAV5, amino acids 589 and 590 of AAV7, or amino acids 590 to 591 of AAV8 or AAV10, the peptide insertion comprising an amino acid sequence selected from TNRTSPD (SEQ ID NO:24) and LATNRTSPDA (SEQ ID NO:39), and b) a valine to isoleucine substitution at amino acid 709 of AAV3A or AAV3B, an alanine to isoleucine substitution at position 709 of AAV1 or AAV6, an asparagine to isoleucine substitution at amino acid 707 of AAV4 or amino acid 709 of AAV9 or a threonine to isoleucine substitution at amino acid 710 of AAV7 or amino acid 711 of AAV8 or AAV10 or a glutamine to isoleucine substitution at amino acid 697 of AAV5. In other embodiments, the variant capsid protein comprises a) a peptide insertion comprising, consisting essentially of, or consisting of the amino acid sequence LATNRTSPDA (SEQ ID NO:39) between amino acids 587 and 588 of AAV2 capsid and b) a valine to isoleucine amino acid substitution at amino acid 708 compared to the amino acid sequence of AAV2, wherein the variant capsid protein comprises from 1 to 5, from 5 to 10, or from 10 to 15 amino acid substitutions. In yet another embodiment, the variant capsid protein comprises a) a peptide insertion comprising the amino acid sequence TNRTSPD (SEQ ID NO:24) between amino acids 587 and 588 of AAV2 capsid and b) a valine to isoleucine amino acid substitution at amino acid 708 compared to the amino acid sequence of AAV2. The variant AAV capsid may have at least about 85%, at least about 90%, at least about 95%, at least about 98%, or greater amino acid sequence identity to the entire length of the amino acid sequence set forth in SEQ ID NO:2.

In yet another embodiment, the variant capsid protein comprises a) a peptide insertion comprising the amino acid sequence TNRTSPD (SEQ ID NO:24) or comprising, consisting essentially of, or consisting of the amino acid sequence LATNRTSPDA (SEQ ID NO:39) between amino acids 587 and 588 of AAV2 capsid and is otherwise identical to the amino acid sequence of SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 50)
MAADGYLPDWLEDTLSEGIRQWWKLKPGPPPPKPAERHKDDSRGLVLPQYK

YLGPFNGLDKGEPVNEADAAALEHDKAYDRQLDSGDNPYLKYNHADAEFQE

RLKEDTSFGGNLGRAVFQAKKRVLEPLGLVEEPVKTAPGKKRPVEHSPVEP

DSSSGTGKAGQQPARKRLNFGQTGDADSVPDPQPLCQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDPNRFHCHFSPRDWQRLINNNWGF

RPKRLNFKLFNIQVKEVTQNDGTTTIANNLTSTVQVFTDSEYQLPYVLGSA

HQGCLPPFRADVFMVPQYGYLTLNNGSQAVGRSSFYCLEYFPSQMLRTGNN

FTFSYTFEDVPFHSSYAHSQSLDRLMNPLIDQYLYYLSRTNTPSGTTTQSR

LQFSQAGASDIRDQSRNWLPGPCYRQQRVSKTSADNNNSEYSWTGATKYHL

NGRDSLVNPGPAMASHKDDEEKFFPQSGVLIFGKQGSEKTNVDIEKVMITD

EEEIRTTNPVATEQYGSVSTNLQRGNLATNRTSPDARQAATADVNTQGVLP

GMVWQDRDVYLQGPIWAKIPHTDGHFHPSPLMGGFGLKHPPPQILIKNTPV

PANPSTTFSAAKFASFITQYSTGQVSVEIEWELQKENSKRWNPEIQYTSNY

NKSVNVDFTVDTNGVYSEPRPIGTRYLTRNL

In another embodiment, a variant AAV capsid protein is provided comprising a) a peptide insertion in the GH-loop of the capsid protein, wherein the peptide insertion comprises an amino acid sequence selected from GKSKVID (SEQ ID NO:23) and LAGKSKVIDA (SEQ ID NO:38), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: M1L, L15P, P34A, N57D, N66K, R81Q, Q101R, S109T, R144K, R144M, Q164K, T176P, L188I, S196Y, G226E, G236V, I240T, P250S, N312K, P363L, D368H, N449D, T456K, S463Y, D472N, R484C, A524T, P535S, N551S, A593E, I698V, V708I, V719M, S721L, L735Q and a combination thereof. Preferably, the peptide insertion site is located between amino acids 587 and 588 of AAV2 capsid or the corresponding position in the capsid protein of another AAV serotype. The variant AAV capsid may have at least about 85%, at least about 90%, at least about 95%, at least about 98%, or greater amino acid sequence identity to the entire length of the amino acid sequence set forth in SEQ ID NO:2. In some embodiments, the variant AAV capsid comprises a peptide insertion located between amino acids 587 and 588 of AAV2 capsid comprising the amino acid sequence GKSKVID (SEQ ID NO:23) or comprising, consisting essentially of or consisting of the amino acid sequence LAGKSKVIDA (SEQ ID NO:38) and is otherwise identical to the amino acid sequence of SEQ ID NO:2. In other embodiments, the variant AAV capsid comprises a) a peptide insertion comprising, consisting essentially of, or consisting of the amino acid sequence LAGKSKVIDA (SEQ ID NO:38) between amino acids 587 and 588 of AAV2 capsid and comprises at least one amino acid substitution.

In some embodiments, the variant AAV capsid has an amino acid sequence having at least about 85%, at least about 90%, at least about 95%, at least about 98% sequence identity to or is 100% identical to the following amino acid sequence:

(SEQ ID NO: 51)
MAADGYLPDWLEDTLSEGIRQWWKLKPGPPPPKRAERHKDDSRGLVLPGYK

YLGPFNGLDKGEPVNEADAAALEHDKAYDRQLDSGDNPYLKYNHADAEFQE

RLKEDTSFGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGSA

HQGCLPPFPADVFMVPQYGYLTLNNGSQAVGRSSFYCLEYFPSQMLRTGNN

FTFSYTFEDVPFHSSYAHSQSLDRLMNPLIDQYLYYLSRTNTPSGTTTQSR

LQFSQAGASDIRDQSRNWLPGPCYRQQRVSKTSADNNNSEYSWTGATKYHL

NGRDSLVNPGPAMASHKDDEEKFFPQSGVLIFGKQGSEKTNVDIEKVMITD

EEEIRTTNPVATEQYGSVSTNLQRGNLAGKSKVIDARQAATADVNTQGVLP

GMVWQDRDVYLQGPIWAKIPHTDGHFHPSPLMGGFGLKHPPPQILIKNTPV

ANPSTTFSAAKFASFITQYSTGQVSVEIEWELQKENSKRWNPEIQYTSNYN

KSVNVDFTVDTNGVYSEPRPIGTRYLTRNL

In another embodiment, a variant AAV capsid protein is provided comprising a) a peptide insertion in the GH-loop of the capsid protein, wherein the peptide insertion comprises an amino acid sequence selected from ASDSTKA (SEQ ID NO:15) and LAASDSTKAA (SEQ ID NO:30), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: M1L, L15P, P34A, N57D, N66K, R81Q, Q101R, S109T, R144K, R144M, Q164K, T176P, L188I, S196Y, G226E, G236V, I240T, P250S, N312K, P363L, D368H, N449D, T456K, S463Y, D472N, R484C, A524T, P535S, N551S, A593E, I698V, V708I, V719M, S721L, L735Q and a combination thereof. Preferably, the peptide insertion site is located between amino acids 587 and 588 of AAV2 capsid or the corresponding position in the capsid protein of another AAV serotype. The variant AAV capsid may have at least about 85%, at least about 90%, at least about 95%, at least about 98%, or greater amino acid sequence identity to the entire length of the amino acid sequence set forth in SEQ ID NO:2. In yet another embodiment, the variant capsid comprises a peptide insertion comprising the amino acid sequence ASDSTKA (SEQ ID NO:15) or comprising, consisting essentially of, or consisting of the amino acid sequence LAASDSTKAA (SEQ ID NO:30) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 52)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSFGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGSA

HQGCLPPFPADVFMVPQYGYLTLNNGSQAVGRSSFYCLEYFPSQMLRTGNN

FTFSYTFEDVPFHSSYAHSQSLDRLMNPLIDQYLYYLSRTNTPSGTTTQSR

LQFSQAGASDIRDQSRNWLPGPCYRQQRVSKTSADNNNSEYSWTGATKYHL

NGRDSLVNPGPAMASHKDDEEKFFPQSGVLIFGKQGSEKTNVDIEKVMITD

EEEIRTTNPVATEQYGSVSTNLQRGNLAASDSTKAARQAATADVNTQGVLP

QMVWQDRDVYLQGPIWAKIPHTDGHFHPSPLMGGFGLKHPPPQILIKNTPV

PANPSTTFSAAKFASFITQYSTGQVSVEIEWELQKENSKRWNPEIQYTSNY

NKSVNVDFTVDTNGVYSEPRPIGTRYLTRNL

In another embodiment, a variant AAV capsid protein is provided comprising a) a peptide insertion in the GH-loop of the capsid protein, wherein the peptide insertion comprises an amino acid sequence selected from KDRAPST (SEQ ID NO:26) and LAKDRAPTSA (SEQ ID NO:41), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: M1L, L15P, P34A, N57D, N66K, R81Q, Q101R, S109T, R144K, R144M, Q164K, T176P, L188I, S196Y, G226E, G236V, I240T, P250S, N312K, P363L, D368H, N449D, T456K, S463Y, D472N, R484C, A524T, P535S, N551S, A593E, I698V, V708I, V719M, S721L, L735Q and a combination thereof. Preferably, the peptide insertion site is located between amino acids 587 and 588 of AAV2 capsid or the corresponding position in the capsid protein of another AAV serotype. The variant AAV capsid may have at least about 85%, at least about 90%, at least about 95%, at least about 98%, or greater amino acid sequence identity to the entire length of the amino acid sequence set forth in SEQ ID NO:2. In yet another embodiment, the variant capsid comprises a peptide insertion comprising the amino acid sequence KDRAPST (SEQ ID NO:26) or comprising, consisting essentially of, or consisting of the amino acid sequence LAKDRAPTSA (SEQ ID NO:41) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 53)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSFGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGSA

HQGCLPPFPADVFMVPQYGYLTLNNGSQAVGRSSFYCLEYFPSQMLRTGNN

FTFSYTFEDVPFHSSYAHSQSLDRLMNPLIDQYLYYLSRTNTPSGTTTQSR

LQFSQAGASDIRDQSRNWLPGPCYRQQRVSKTSADNNNSEYSWTGATKYHL

NGRDSLVNPGPAMASHKDDEEKFFPQSGVLIFGKQGSEKTNVDIEKVMITD

EEEIRTTNPVATEQYGSVSTNLQRGNLAKDRAPSTARQAATADVNTQGVLP

GMVWQDRDVYLQGPIWAKIPHTDGHFHPSPLMGGFGLKHPPPQILIKNTPV

PANPSTTFSAAKFASFITQYSTGQVSVEIEWELQKENSKRWNPEIQYTSNY

NKSVNVDFTVDTNGVYSEPRPIGTRYLTRNL

In another embodiment, a variant AAV capsid protein is provided comprising a) a peptide insertion in the GH-loop of the capsid protein, wherein the peptide insertion comprises an amino acid sequence selected from HQDTTKN (SEQ ID NO:19) and LAHQDTTKNA (SEQ ID NO:34), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at one or more of the corresponding positions: M1L, L15P, P34A, N57D, N66K, R81Q, Q101R, S109T, R144K, R144M, Q164K, T176P, L188I, S196Y, G226E, G236V, I240T, P250S, N312K, P363L, D368H, N449D, T456K, S463Y, D472N, R484C, A524T, P535S, N551S, A593E, I698V, V708I, V719M, S721L, L735Q and a combination thereof. Preferably, the peptide insertion site is located between amino acids 587 and 588 of AAV2 capsid or the corresponding position in the capsid protein of another AAV serotype. The variant AAV capsid may have at least about 85%, at least about 90%, at least about 95%, at least about 98%, or greater amino acid sequence identity to the entire length of the amino acid sequence set forth in SEQ ID NO:2. In yet another embodiment, the variant capsid comprises a peptide insertion comprising the amino acid sequence HQDTTKN (SEQ ID NO:19) or comprising, consisting essentially of, or consisting of the amino acid sequence LAHQDTTKNA (SEQ ID NO:34) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 54)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSFGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGSA

HQGCLPPFPADVFMVPQYGYLTLNNGSQAVGRSSFYCLEYFPSQMLRTGNN

FTFSYTFEDVPFHSSYAHSQSLDRLMNPLIDQYLYYLSRTNTPSGTTTQSR

LQFSQAGASDIRDQSRNWLPGPCYRQQRVSKTSADNNNSEYSWTGATKYHL

NGRDSLVNPGPAMASHKDDEEKFFPQSGVLIFGKQGSEKTNVDIEKVMITD

EEEIRTTNPVATEQYGSVSTNLQRGNLAHQDTTKNARQAATADVNTQGVLP

GMVWQDRDVYLQGPIWAKIPHTDGHFHPSPLMGGFGLKHPPPQILIKNTPV

PANPSTTFSAAKFASFITQYSTGQVSVEIEWELQKENSKRWNPEIQYTSNY

NKSVNVDFTVDTNGVYSEPRPIGTRYLTRNL

In another embodiment, a variant AAV capsid protein is provided comprising a) a peptide insertion in the GH-loop of the capsid protein, wherein the peptide insertion comprises an amino acid sequence selected from ISNENEH (SEQ ID NO:21) and LPISNENEHA (SEQ ID NO:36), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at one or more of the corresponding positions: M1L, L15P, P34A, N57D, N66K, R81Q, Q101R, S109T, R144K, R144M, Q164K, T176P, L188I, S196Y, G226E, G236V, I240T, P250S, N312K, P363L, D368H, N449D, T456K, S463Y, D472N, R484C, A524T, P535S, N551S, A593E, I698V, V708I, V719M, S721L, L735Q and a combination thereof. Preferably, the peptide insertion site is located between amino acids 587 and 588 of AAV2 capsid or the corresponding position in the capsid protein of another AAV serotype. The variant AAV capsid may have at least about 85%, at least about 90%, at least about 95%, at least about 98%, or greater amino acid sequence identity to the entire length of the amino acid sequence set forth in SEQ ID NO:2. In yet another embodiment, the variant capsid comprises a peptide insertion comprising the amino acid sequence ISNENEH (SEQ ID NO:21) or comprising, consisting essentially of, or consisting of the amino acid sequence LPISNENEHA (SEQ ID NO:36) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 55)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSFGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNYKLFNIQVKEVTQNDGTTTIANNLTSTVQVFTDSEYQLPYVLGSA

HQGCLPPFPADVFMVPQYGYLTLNNGSQAVGRSSFYCLEYFRSQMLRTGNN

FTFSYTFEDVPFHSSYAHSQSLDRLMNPLIDQYLYYLSRTNTPSGTTTQSR

LQFSQAGASDIRDQSRNWLPGPCYRQQRVSKTSADNNNSEYSWTGATKYHL

NGRDSLVNPGPAMASHKDDEEKFFPQSGVLIFGKQGSEKTNVDIEKVMITD

EEEIRTTNPVATEQYGSVSTNLQRGNLPISNENEHARQAATADVNTQGVLP

GMVWQDRDVYLQGPIWAKIPHTDGHFHPSPLMGGFGLKHPPPQILIKNTPV

PANPSTTFSAAKFASFITQYSTGQVSVEIEWELQKENSKRWNPEIQYTSNY

NKSVNVDFTVDTNGVYSEPRPIGTRYLTRNL

In another embodiment, a variant AAV capsid protein is provided comprising a) a peptide insertion in the GH-loop of the capsid protein, wherein the peptide insertion comprises an amino acid sequence selected from QANANEN (SEQ ID NO:22) and LPQANANENA (SEQ ID NO:37), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: M1L, L15P, P34A, N57D, N66K, R81Q, Q101R, S109T, R144K, R144M, Q164K, T176P, L188I, S196Y, G226E, G236V, I240T, P250S, N312K, P363L, D368H, N449D, T456K, S463Y, D472N, R484C, A524T, P535S, N551S, A593E, I698V, V708I, V719M, S721L, L735Q and a combination thereof. Preferably, the peptide insertion site is located between amino acids 587 and 588 of AAV2 capsid or the corresponding position in the capsid protein of another AAV serotype. The variant AAV capsid may have at least about 85%, at least about 90%, at least about 95%, at least about 98%, or greater amino acid sequence identity to the entire length of the amino acid sequence set forth in SEQ ID NO:2. In yet another embodiment, the variant capsid comprises a peptide insertion comprising the amino acid sequence QANANEN (SEQ ID NO:22) or comprising, consisting essentially of, or consisting of the amino acid sequence LPQANANENA (SEQ ID NO:37) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 56)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSFGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGSA

HQGCLPPFPADVFMVPQYGYLTLNNGSQAVGRSSFYCLEYFPSQMLRTGNN

FTFSYTFEDVPFHSSYAHSQSLDRLMNPLIDQYLYYLSRTNTPSGTTTQSR

LQFSQAGASDIRDQSRNWLPGPCYRQQRVSKTSADNNNSEYSWTGATKYHL

NGRDSLVNPGPAMASHKDDEEKFFPQSGVLIFGKQGSEKTNVDIEKVMITD

EEEIRTTNPVATEQYGSVSTNLQRGNLPQANANENARQAATADVNTQGVLP

GMVWQDRDVYLQGPIWAKIPHTDGHFHPSPLMGGFGLKHPPPQILIKNTPV

PANPSTTFSAAKFASFITQYSTGQVSVEIEWELQKENSKRWNPEIQYTSNY

NKSVNVDFTVDTNGVYSEPRPIGTRYLTRNI

In another embodiment, a variant AAV capsid protein is provided comprising a) a peptide insertion in the GH-loop of the capsid protein, wherein the peptide insertion comprises an amino acid sequence selected from HPDTTKN (SEQ ID NO:18) and LAHPDTTKNA (SEQ ID NO:33), and b) one or more of the following amino acid substitutions compared to the amino acid sequence of AAV2 (SEQ ID NO:2) or the corresponding substitution in another AAV parental serotype (i.e. other than AAV2), wherein the substituted amino acid(s) do not naturally occur at the corresponding positions: M1L, L15P, P34A, N57D, N66K, R81Q, Q101R, S109T, R144K, R144M, Q164K, T176P, L188I, S196Y, G226E, G236V, I240T, P250S, N312K, P363L, D368H, N449D, T456K, S463Y, D472N, R484C, A524T, P535S, N551S, A593E, I698V, V708I, V719M, S721L, L735Q and a combination thereof. Preferably, the peptide insertion site is located between amino acids 587 and 588 of AAV2 capsid or the corresponding position in the capsid protein of another AAV serotype. The variant AAV capsid may have at least about 85%, at least about 90%, at least about 95%, at least about 98%, or greater amino acid sequence identity to the entire length of the amino acid sequence set forth in SEQ ID NO:2. In yet another embodiment, the variant capsid comprises a peptide insertion comprising the amino acid sequence HPDTTKN (SEQ ID NO:18) or comprising, consisting essentially of, or consisting of the amino acid sequence LAHPDTTKNA (SEQ ID NO:33) between amino acids 587 and 588 of AAV2 capsid and is otherwise identical to the amino acid sequence set forth in SEQ ID NO:2. In some embodiments, the variant AAV capsid has an amino acid sequence having at least about 85%, at least about 90%, at least about 95%, at least about 98% sequence identity to or is 100% identical to the following amino acid sequence:

(SEQ ID NO: 57)
MAADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFQE

RLKEDTSFGGNLGRAVFQAKKRVLEPLGLVEEPVKTAPGKKRPVEHSPVEP

DSSSGTGKAGQQPARKRLNFGQTGDADSVPDPQPLGQPPAAPSGLGTNTMA

TGSGAPMADNNEGADGVGNSSGNWHCDSTWMGDRVITTSTRTWALPTYNNH

LYKQISSQSGASNDNHYFGYSTPWGYFDFNRFHCHFSPRDWQRLINNNWGF

RPKRLNFKLFNIQVKEVTQNDGTTTIANNLTSTVQVFTDSEYQLPYVLGSA

HQGCLPPFPADVFMVPQYGYLTLNNGSQAVGRSSFYCLEYFPSQMLRTGNN

FTFSYTFEDVPFHSSYAHSQSLDRLMNPLIDQYLYYLSRTNTPSGTTTQSR

LQFSQAGASDIRDQSRNWLPGPCYRQQRVSKTSADNNNSEYSWTGATKYHL

NGRDSLVNPGPAMASHKDDEEKFFPQSGVLIFGKQGSEKTNVDIEKVMITD

EEEIRTTNPVATEQYGSVSTNLQRGNLAHPDTTKNARQAATADVNTQGVLP

GMVWQDRDVYLQGPIWAKIPHTDGHFHPSPLMGGFGLKHPPPQILIKNTPV

PANPSTTFSAAKFASFITQYSTGQVSVEIEWELQKENSKRWNPEIQYTSNY

NKSVNVDFTVDTNGVYSEPRPIGTRYLTRNL.

In several aspects, a variant AAV capsid protein is provided comprising one or more amino acid substitutions relative to a corresponding parental AAV capsid protein, wherein the variant capsid protein, when present in an AAV virion, confers increased infectivity of a retinal cell compared to the infectivity of a retinal cell by an AAV virion comprising the corresponding parental AAV capsid protein.

In some embodiments, a variant AAV capsid protein comprises a P34A amino acid substitution compared to the amino acid sequence of AAV2 capsid (SEQ ID NO:2) or a P33A amino acid substitution compared to the amino acid sequence of AAV5 capsid (SEQ ID NO:6). In some preferred embodiments, the variant capsid protein comprises an amino acid sequence having at least about 85%, at least about 90%, at least about 95%, at least about 98%, or at least about 99%, or greater, amino acid sequence identity to the entire length of the amino acid sequence set forth in SEQ ID NO:2 or SEQ ID NO:6 and comprises a P34A or P33A amino acid substitution compared to the amino acid sequence of AAV2 or AAV5 capsid respectively. In some preferred embodiments, the variant capsid protein comprises an amino acid sequence comprising a P34A amino acid substitution compared to the amino acid sequence set forth in SEQ ID NO 2 and is otherwise identical to the amino acid sequence set forth in SEQ ID NO:2. In related embodiments, the variant capsid protein comprises a P34A amino acid substitution compared to the amino acid sequence of SEQ ID NO:2, wherein the variant capsid protein comprises from 1 to 5, from 5 to 10, or from 10 to 15 amino acid substitutions compared to the amino acid sequence of an AAV2 capsid protein set forth in SEQ ID NO:2.

In other embodiments a variant AAV capsid protein comprises an amino acid substitution at amino acid 164 compared to the amino acid sequence of AAV2 capsid (SEQ ID NO:2) or the corresponding position in another AAV parental serotype (i.e. other than AAV2), wherein the substituted amino acid does not naturally occur at the corresponding position. In some preferred embodiments, the variant capsid protein comprises an amino acid sequence having at least about 85%, at least about 90%, at least about 95%, at least about 98%, or at least about 99%, or greater, amino acid sequence identity to the entire length of the amino acid sequence set forth in SEQ ID NO 2 and comprises an amino acid substitution at amino acid 164 compared to the amino acid sequence of AAV2 capsid (SEQ ID NO:2). In some embodiments, the rAAV virion comprises a glutamine to lysine amino acid substitution at amino acid 164 compared to amino acid sequence of AAV1, AAV2 or AAV6 or at amino acid 165 compared to the amino acid sequence of AAV7, AAV8, or AAV10; or comprises a serine to lysine substitution at amino acid 160 of AAV5 or comprises an alanine to lysine substitution at amino acid 164 of AAV9. In related embodiments, the variant capsid protein comprises an amino acid substitution at amino acid 164 (e.g. Q164K) compared to the amino acid sequence of AAV2 capsid (SEQ ID NO:2), wherein the variant capsid protein comprises from 1 to 5, from 5 to 10, or from 10 to 15 amino acid substitutions compared to the amino acid sequence of an AAV2 capsid protein set forth in SEQ ID NO:2. In some preferred embodiments, the variant capsid protein comprises an amino acid sequence comprising a Q164K amino acid substitution compared to the amino acid sequence set forth in SEQ ID NO:2 and is otherwise identical to the amino acid sequence set forth in SEQ ID NO:2. In other embodiments the variant capsid protein comprises Q164K and V708I amino acid substitutions compared to the amino acid sequence of AAV2 capsid (SEQ ID NO:2) or the corresponding substitutions in another AAV parental serotype (i.e. other than AAV2) and is at least about 85%, at least about 90%, at least about 95%, at least about 98%, or at least about 99%, or greater, amino acid sequence identity to the entire length of the amino acid sequence set forth in SEQ ID NO:2.

In other embodiments a variant AAV capsid protein comprises an amino acid substitution at amino acid 698 compared to the amino acid sequence of AAV2 capsid (SEQ ID NO:2) or the corresponding position in another AAV parental serotype (i.e. other than AAV2), wherein the substituted amino acid does not naturally occur at the corresponding position. In some preferred embodiments, the variant capsid protein comprises an amino acid sequence having at least about 85%, at least about 90%, at least about 95%, at least about 98%, or at least about 99%, or greater, amino acid sequence identity to the entire length of the amino acid sequence set forth in SEQ ID NO 2 and comprises an amino acid substitution at amino acid 698 compared to the amino acid sequence of AAV2 capsid (SEQ ID NO:2). In some embodiments, the rAAV virion comprises an isoleucine to valine amino acid substitution at amino acid 698 compared to amino acid sequence of AAV2, or at amino acid 699 compared to the amino acid sequence of AAV3A, AAV3B, or AAV9, or at amino acid 687 of AAV5, or at amino acid 700 of AAV7, or at amino acid 701 of AAV8 or AAV10. In related embodiments, the variant capsid protein comprises an amino acid substitution at amino acid 699 (e.g. I698V) compared to the amino acid sequence of AAV2 capsid (SEQ ID NO:2), wherein the variant capsid protein comprises from 1 to 5, from 5 to 10, or from 10 to 15 amino acid substitutions compared to the amino acid sequence of an AAV2 capsid protein set forth in SEQ ID NO:2. In some preferred embodiments, the variant capsid protein comprises an amino acid sequence comprising an I698V amino acid substitution compared to the amino acid sequence set forth in SEQ ID NO:2 and is otherwise identical to the amino acid sequence set forth in SEQ ID NO:2.

In other embodiments a variant AAV capsid protein comprises an amino acid substitution at amino acid 109 compared to the amino acid sequence of AAV2 capsid (SEQ ID NO:2) or the corresponding position in another AAV parental serotype (i.e. other than AAV2). In some preferred embodiments, the variant capsid protein comprises an amino acid sequence having at least about 85%, at least about 90, at least about 95%, at least about 98%, or at least about 99%, or greater, amino acid sequence identity to the entire length of the amino acid sequence set forth in SEQ ID NO 2 and comprises an amino acid substitution at amino acid 109 compared to the amino acid sequence of AAV2 capsid (SEQ ID NO:2). In some embodiments, the variant capsid protein comprises a serine to threonine amino acid substitution at position 109 compared to the amino acid sequence of AAV1, AAV3A, AAV3B, AAV4, AAV7, AAV8, AAV9, or AAV10 or at position 108 compared to the amino acid sequence of AAV5 or AAV6. In related embodiments, the variant capsid protein comprises an S109T amino acid substitution compared to the amino acid sequence AAV2, wherein the variant capsid protein comprises from 1 to 5, from 5 to 10, or from 10 to 15 amino acid substitutions. In other related embodiments, the variant capsid protein comprises an S109T amino acid substitution and an A593E amino acid substitution compared to the amino acid sequence of AAV2. In some embodiments the variant capsid protein comprises S109T and A493V and optionally A593E and/or V708I amino acid substitutions compared to the amino acid sequence of AAV2 capsid (SEQ ID NO:2) or the corresponding substitutions in another AAV parental serotype (i.e. other than AAV2) and has at least about 85%, at least about 90%, at least about 95%, at least about 98%, or at least about 99%, or greater, amino acid sequence identity to the entire length of the amino acid sequence set forth in SEQ ID NO 2. In some preferred embodiments the variant capsid protein comprises S109T, A493V, A593E and V708I amino acid substitutions compared to the amino acid sequence of AAV2 capsid (SEQ ID NO:2) or the corresponding substitutions in another AAV parental serotype (i.e. other than AAV2) and is at least about 85%, at least about 90%, at least about 95%, at least about 98%, or at least about 99%, or greater, amino acid sequence identity to the entire length of the amino acid sequence set forth in SEQ ID NO 2. In other preferred embodiments, the variant capsid protein comprises S109T and V708I amino acid substitutions compared to the amino acid sequence of AAV2 capsid and has at least about 85%, at least about 90%, at least about 95%, at least about 98%, or at least about 99%, or greater, amino acid sequence identity to the entire length of the amino acid sequence set forth in SEQ ID NO 2 or is otherwise identical to the amino acid sequence of SEQ ID NO:2.

In other embodiments a variant AAV capsid protein comprises an amino acid substitution at amino acid 593 compared to the amino acid sequence of AAV2 capsid (SEQ ID NO:2) or the corresponding position in another AAV parental serotype (i.e. other than AAV2). In some preferred embodiments, the variant capsid protein comprises an amino acid sequence having at least about 85%, at least about 90%, at least about 95%, at least about 99%, or at least about 99%, or greater, amino acid sequence identity to the entire length of the amino acid sequence set forth in SEQ ID NO 2 and comprises an amino acid substitution at amino acid 593 compared to the amino acid sequence of AAV2 capsid (SEQ ID NO:2). In some embodiments, the variant capsid protein comprises a glycine to glutamate amino acid substitution at amino acid 594 compared to the amino acid sequence of AAV1, AAV3A, AAV6, or AAV9, or at amino acid 583 of AAV5, or at amino acid 596 of AAV8 or AAV10, or an arginine to glutamate amino acid substitution at amino acid 594 of AAV3B, or an aspartate to glutamate amino acid substitution at amino acid 592 of AAV4 or a glutamine to glutamate amino acid substitution at position 595 of AAV7. In other embodiments, the variant capsid protein comprises an A593E amino acid substitution compared to the amino acid sequence of AAV2 and does not comprise one or more of the following amino acid substitutions compared to the amino acid sequence of AAV2: I19V, V369A, K26R, N215D, G355S, V46A and S196P. In related embodiments, the variant capsid protein comprises A593E and N596D amino acid substitutions compared to the amino acid sequence of AAV2 and has at least about 85%, at least about 90%, at least about 95%, at least about 98% or at least about 99% identity to the entire length of the amino acid sequence set forth in SEQ ID NO 2. In other embodiments, the variant capsid comprises A593E and N596D amino acid substitutions compared to the amino acid sequence of AAV2 and is otherwise identical to the amino acid sequence of AAV2. In other embodiments, the variant capsid comprises A593E and V708I amino acid substitutions compared to the amino acid sequence of AAV2 and has at least about 85%, at least about 90%, at least about 95%, at least about 98% or at least about 99% identity to the entire length of the amino acid sequence set forth in SEQ ID NO 2. In other embodiments, the variant capsid comprises A593E and V708I amino acid substitutions compared to the amino acid sequence of AAV2 and is otherwise identical to the amino acid sequence of AAV2.

In other embodiments a variant AAV capsid protein comprises an amino acid substitution at amino acid 708 compared to the amino acid sequence of AAV2 capsid (SEQ ID NO:2) or the corresponding position in another AAV parental serotype (i.e. other than AAV2) wherein the substituted amino acid does not naturally occur at the corresponding position. Preferably, the rAAV virion does not comprise a proline to serine substitution at amino acid 250 compared to AAV2 or a corresponding amino acid in another AAV parental serotype. In some embodiments, the variant capsid protein comprises an amino acid sequence having at least about 85%, at least about 90%, at least about 95%, at least about 98%, or at least about 99%, or greater, amino acid sequence identity to the entire length of the amino acid sequence set forth in SEQ ID NO 2 and comprises an amino acid substitution at amino acid 708 compared to the amino acid sequence of AAV2 capsid (SEQ ID NO:2). In preferred embodiments, the variant capsid protein comprises a valine to isoleucine (V708I) substitution at amino acid 708 compared to the amino acid sequence of AAV2 capsid and has at least about 85%, at least about 90%, at least about 95%, at least about 98%, or at least about 99%, or greater, amino acid sequence identity to the entire length of the amino acid sequence set forth in SEQ ID NO 2 or is otherwise identical to the amino acid sequence of SEQ ID NO:2, wherein the variant capsid protein does not comprise a P250S amino acid substitution. In some embodiments, the variant capsid protein comprises a valine to isoleucine substitution at amino acid 709 of AAV3A or AAV3B, an alanine to isoleucine substitution at position 709 of AAV1 or AAV6, an asparagine to isoleucine substitution at amino acid 707 of AAV4 or amino acid 709 of AAV9 or a threonine to isoleucine substitution at amino acid 710 of AAV7 or amino acid 711 of AAV8 or AAV10 or a glutamine to isoleucine substitution at amino acid 697 of AAV5. In related embodiments, the variant capsid protein comprises a V708I amino acid substitution compared to the amino acid sequence of AAV2, wherein the variant capsid protein comprises from 2 to 5, from 5 to 10, or from 10 to 15 amino acid substitutions and wherein the variant capsid protein does not comprise a P250S amino acid substitution. In other embodiments, the variant capsid protein comprises a V708I amino acid substitution and also comprises an A593E and/or an S109T amino acid substitution compared to the amino acid sequence of AAV2. In other related embodiments, the variant capsid comprises V708I and A593E amino acid substitutions compared to the amino acid sequence of AAV2, wherein the variant capsid protein is otherwise identical to the amino acid sequence of AAV2. In other related embodiments, the variant capsid comprises V708I and S109T amino acid substitutions compared to the amino acid sequence of AAV2, wherein the variant capsid protein is otherwise identical to the amino acid sequence of AAV2. In other embodiments, the variant capsid protein comprises V708I and V719M amino acid substitutions compared to the amino acid sequence of AAV2 and has at least about 85%, at least about 90%, at least about 95%, at least about 98%, or at least about 99%, or greater, amino acid sequence identity to the entire length of the amino acid sequence set forth in SEQ ID NO 2 or is otherwise identical to the amino acid sequence of SEQ ID NO:2. In other embodiments, the variant capsid protein comprises V708I and R733C amino acid substitutions compared to the amino acid sequence of AAV2 and has at least about 85%, at least about 90%, at least about 95%, at least about 98%, or at least about 99%, or greater, amino acid sequence identity to the entire length of the amino acid sequence set forth in SEQ ID NO 2 or is otherwise identical to the amino acid sequence of SEQ ID NO:2. In other embodiments, the variant capsid protein comprises V708I and G727D amino acid substitutions compared to the amino acid sequence of AAV2 and has at least about 85%, at least about 90%, at least about 95%, at least about 98%, or at least about 99%, or greater, amino acid sequence identity to the entire length of the amino acid sequence set forth in SEQ ID NO 2 or is otherwise identical to the amino acid sequence of SEQ ID NO:2.

In other embodiments a variant AAV capsid protein comprises an amino acid substitution at amino acid 196 compared to the amino acid sequence of AAV2 capsid (SEQ ID NO:2) or the corresponding position in another AAV parental serotype (i.e. other than AAV2), wherein the substituted amino acid does not naturally occur at the corresponding position and is optionally other than proline. In some preferred embodiments, the variant capsid protein comprises an amino acid sequence having at least about 85%, at least about 90%, at least about 95%, at least about 98%, or at least about 99%, or greater, amino acid sequence identity to the entire length of the amino acid sequence set forth in SEQ ID NO 2 and comprises an amino acid substitution at amino acid 196 compared to the amino acid sequence of AAV2 capsid (SEQ ID NO:2) and is optionally other than an S196P substitution. In preferred embodiments, the variant capsid protein comprises a serine to tyrosine amino acid substitution at amino acid 196 of AAV2 or AAV9 or at amino acid 197 of AAV7, AAV8 or AAV10 or at amino acid 186 of AAV5; or an alanine to tyrosine substitution at amino acid 196 of AAV1 or AAV6; or a methionine to tyrosine substitution at amino acid 191 of AAV4; or a threonine to tyrosine substitution at amino acid 196 of AAV3A or AAV3B. In a related embodiment, the variant capsid protein comprises an amino acid sequence comprising an S196Y amino acid substitution compared to the amino acid sequence set forth in SEQ ID NO:2 and is otherwise identical to the amino acid sequence set forth in SEQ ID NO:2. In related embodiments, the variant capsid protein comprises an amino acid substitution at amino acid 196 other than an S196P substitution (e.g. comprises an S196Y substitution) compared to the amino acid sequence of AAV2 capsid (SEQ ID NO:2), wherein the variant capsid protein comprises from 1 to 5, from 5 to 10, or from 10 to 15 amino acid substitutions compared to the amino acid sequence of an AAV2 capsid protein set forth in SEQ ID NO:2.

In other embodiments a variant AAV capsid protein comprises an amino acid substitution at amino acid 175 compared to the amino acid sequence of AAV2 capsid (SEQ ID NO:2) or the corresponding position in another AAV parental serotype (i.e. other than AAV2), wherein the substituted amino acid does not naturally occur at the corresponding position. In some preferred embodiments, the variant capsid protein comprises an amino acid sequence having at least about 85%, at least about 90%, at least about 95%, at least about 98%, or at least about 99%, or greater, amino acid sequence identity to the entire length of the amino acid sequence set forth in SEQ ID NO 2 and comprises an amino acid substitution at amino acid 175 compared to the amino acid sequence of AAV2 capsid (SEQ ID NO:2). In some embodiments, the variant capsid comprises a Q175H amino acid substitution compared to the amino acid sequence of AAV2 as set forth in SEQ ID NO:2 or a glutamine to histidine substitution at the corresponding position in another AAV parental serotype. In related embodiments, the variant capsid protein comprises an amino acid substitution at amino acid 175 (e.g. Q175H) compared to the amino acid sequence of AAV2 capsid (SEQ ID NO:2), wherein the variant capsid protein comprises from 1 to 5, from 5 to 10, or from 10 to 15 amino acid substitutions compared to the amino acid sequence of an AAV2 capsid protein set forth in SEQ ID NO:2.

In other embodiments a variant AAV capsid protein comprises an amino acid substitution at amino acid 64 compared to the amino acid sequence of AAV2 capsid (SEQ ID NO:2) or the corresponding position in another AAV parental serotype (i.e. other than AAV2), wherein the substituted amino acid does not naturally occur at the corresponding position. In some preferred embodiments, the variant capsid protein comprises an amino acid sequence having at least about 85%, at least about 90%, at least about 95%, at least about 98%, or at least about 99%, or greater, amino acid sequence identity to the entire length of the amino acid sequence set forth in SEQ ID NO 2 and comprises an amino acid substitution at amino acid 64 compared to the amino acid sequence of AAV2 capsid (SEQ ID NO:2). In some embodiments, the rAAV virion comprises a P64S amino acid substitution compared to the amino acid sequence of AAV2 as set forth in SEQ ID NO:2 or a proline to serine substitution at the corresponding position in another AAV parental serotype. In related embodiments, the variant capsid protein comprises an amino acid substitution at amino acid 64 (e.g. P64S) compared to the amino acid sequence of AAV2 capsid (SEQ ID NO:2), wherein the variant capsid protein comprises from 1 to 5, from 5 to 10, or from 10 to 15 amino acid substitutions compared to the amino acid sequence of an AAV2 capsid protein set forth in SEQ ID NO:2.

In other embodiments, a variant AAV capsid protein comprises an amino acid sequence at least 85%, at least 90%, at least 95% or at least 98% identical to a wild-type AAV capsid sequence selected from the group consisting of SEQ ID NOS: 1, 2, 3, 4, 5, 6, 7, 8, 10, 11 and 12 and also comprises i) one or more amino acid substitutions selected from the group consisting of P34A, S109T+V708I, A593E+N596D, V708I+V719M, V708I+G727D, S109T+A493V+A593E+V708I, V708I+R733C, Q164K, and I698V and/or (ii) a peptide insertion selected from the group consisting of QADTTKN (SEQ ID NO:13), ISDQTKH (SEQ ID NO:14), ASDSTKA (SEQ ID NO:15), NQDYTKT (SEQ ID NO:16), HDITKNI (SEQ ID NO:17), PQANANEN (SEQ ID NO:63), TNRTSPD (SEQ ID NO:24), PNSTHGS (SEQ ID NO:25), KDRAPST (SEQ ID NO:26), HQDTTKN (SEQ ID NO:19), HPDTTKN (SEQ ID NO:18), NKTTNKD (SEQ ID NO:20), GKSKVID (SEQ ID NO:23), PISNENEH (SEQ ID NO:64), LAQADTTKNA (SEQ ID NO:27), LAISDQTKHA (SEQ ID NO:28), LGISDQTKHA (SEQ ID NO:29), LAASDSTKAA (SEQ ID NO:30), LAHDITKNIA (SEQ ID NO:32), LPQANANENA (SEQ ID NO:37), LANQDYTKTA (SEQ ID NO:31), LATNRTSPDA (SEQ ID NO:39), LAPNSTHGSA (SEQ ID NO:40), LAKDRAPSTA (SEQ ID NO:41), LAHQDTTKNA (SEQ ID NO:34), LAHPDTTKNA (SEQ ID NO:33), LANKTTNKDA (SEQ ID NO:35), LAGKSKVIDA (SEQ ID NO:38), and LPISNENEHA (SEQ ID NO:36). In some embodiments, the variant AAV capsid comprises the specified one or more amino acid substitutions and/or peptide insertions and is otherwise identical to a sequence selected from the group consisting of SEQ ID NOS: 1-12.

In some embodiments, a variant AAV capsid protein is an ancestral capsid protein. By an ancestral capsid protein it is meant an evolutionary ancestor of a capsid protein that is found in nature today, e.g. AAV1, AAV2, AAV3, AAV4, AAV5, AAV6, AAV7, AAV8, AAV9, AAVrh10, AAV11, AAV12, AAV13, which is generated in silico by random amino acid substitution at positions of degeneracy between AAV capsid proteins that are found in nature today. One nonlimiting example of an ancestral capsid is provided below, wherein the positions of degeneracy (residues 264, 266, 268, 448, 459, 460, 467, 470, 471, 474, 495, 516, 533, 547, 551, 555, 557, 561, 563, 577, 583, 593, 596, 661, 662, 664, 665, 710, 717, 718, 719, 723) are marked as an "X":

```
                                          (SEQ ID NO: 58)
MAADGYLPDWLEDNLSEGIREWWDLKPGAPKPKANQQKQDDGRGLVLPGYK

YLGPFNGLDKGEPVNAADAAALEHDKAYDQQLKAGDNPYLRYNHADAEFQE

RLQEDTSFGGNLGRAVFQAKKRVLEPLGLVEEGAKTAPGKKRPVERSPQRS

PDSSTGIGKKGQQPAKKRLNFGQTGDSESVPDPQPLGEPPAGPSGLGSGTM

AAGGGAPMADNNEGADGVGNASGNWHCDSTWLGDRVITTSTRTWALPTYNN

HLYKQISSXSXGXTNDNHYFGYSTPWGYFDFNRFHCHFSPRDWQRLINNNW

GFRPKRLNFKLFNIQVKEVTTNDGVTTIANNLTSTVQVFSDSEYQLPYVLG

SAHQGCLPPFPADVFMIPQYGYLTLNNGSQAVGRSSFYCLEYFPSQMLRTG

NNFTFSYTFEDVPFHSSYAHSQSLDRLMNPLIDQYLYYLXRTQSTGGTAGX

XELLFSQXGPXXMSXQAKNWLPGPCYRQQRVSKTLXQNNNSNFAWTGATKY

HLNGRXSLVNPGVAMATHKDDEXRFFPSSGVLIFGKXGAGXNNTXLXNVMX

TXEEEIKTTNPVATEXYGVVAXNLQSSNTAPXTGXVNSQGALPGMVWQNRD

VYLQGPIWAKIPHTDGNFHPSPLMGGFGLKHPPPQILIKNTPVPANPPXXF

XXAKFASFITQYSTGQVSVEIEWELQKENSKRWNPEIQYTSNYAKSXNVDF

AVXXXGVYXEPRPIGTRYLTRNL
```

In some embodiments, the ancestral capsid protein comprises an amino acid sequence having at least about 85%, at least about 90%, at least about 95%, at least about 98%, or at least about 99%, or greater, amino acid sequence identity to the entire length of the amino acid sequence set forth in SEQ ID NO:58. In some embodiments, the ancestral capsid protein comprises an amino acid sequence having at least about 85%, at least about 90%, at least about 95%, at least about 98%, or at least about 99%, or greater, amino acid sequence identity to the entire length of the amino acid sequence of AAV2, e.g. as set forth in SEQ ID NO 2. In some embodiments, the ancestral capsid protein comprises an amino acid sequence having at least about 85%, at least about 90%, at least about 95%, at least about 98%, or at least about 99%, or greater, amino acid sequence identity to the entire length of the amino acid sequence of the ancestral sequence disclosed in SEQ ID NO:58 or in SEQ ID NO:2 and comprises one or more amino acid residues selected from the group consisting of: Alanine (A) at 264, Alanine (A) at 266, Serine (S) at 268, Alanine (A) at 448, Threonine (T) at 459, Arginine (R) at 460, Alanine (A) at 467, Serine (S) at 470, Asparagine (N) at 471, Alanine (A) at 474, Serine (S) at 495, Asparagine (D) at 516, Asparagine (D) at 533, Glutamine (Q) at 547, Alanine (A) at 551, Alaninet (A) at 555, Glutamic acid (E) at 557, Methionine (M) at 561, Serine (S) at 563, Glutamine (Q) at 577, Serine (S) at 583, Valine (V) at 593, Threonine T) at 596, Alanine (A) at 661, Valine (V) at 662, Threonine (T) at 664, Proline (P) at 665, Threonine (T) at 710, Aspartic Acid (D) at 717, Asparagine (N) at 718, Glutamic acid (E) at 719, and Serine (S) at 723. In some preferred embodiments, the variant capsid protein comprises an amino acid sequence having at least about 85%, at least about 90%, at least about 95%, at least about 98%, or at least about 99%, in some instances 100% amino acid sequence identity to the entire length of the following amino acid sequence and comprises one or more amino acid residues selected from the group consisting of: Alanine (A) at 264, Alanine (A) at 266, Serine (S) at 268, Alanine (A) at 448, Threonine (T) at 459, Arginine (R) at 460, Alanine (A) at 467, Serine (S) at 470, Asparagine (N) at 471, Alanine (A) at 474, Serine (S) at 495, Asparagine (D) at 516, Asparagine (D) at 533, Glutamine (Q) at 547, Alanine (A) at 551, Alanine (A) at 555, Glutamic acid (E) at 557, Methionine (M) at 561, Serine (S) at 563, Glutamine (Q) at 577, Serine (S) at 583, Valine (V) at 593, Threonine (T) at 596, Alanine (A) at 661, Valine (V) at 662, Threonine (T) at 664, Proline (P) at 665, Threonine (T) at 710, Aspartic Acid (D) at 717, Asparagine (N) at 718, Glutamic acid (E) at 719, and Serine (S) at 723:

```
                                          (SEQ ID NO: 59)
MAADGYLPDWLEDNLSEGIREWWDLKPGAPKPKANQQKQDDGRGLVLPGYK

YLGPFNGLDKGEPVNAADAAALEHDKAYDQQLKAGDNPYLRYNHADAEFQE

RLQEDTSFGGNLGRAVFQAKKRVLEPLGLVEEGAKTAPGKKRPVEPSPQRS

PDSSTGIGKKGQQPAKKRLNFGQTGDSESVPDPQPLGEPPAGPSGLGSGTM

AAGGGAPMADNNEGADGVGNASGNWHCDSTWLGDRVITTSTRTWALPTYNN

HLYKQISSASAGSTNDNHYFGYSTPWGYFDFNRFHCHFSPRDWQRLINNNW

GFRPKRLNFKLFNIQVKEVTTNDGVTTIANNLTSTVQVFSDSEYQLPYVLG

SAHQGCLPPFPADVFMIPQYGYLTLNNGSQAVGRSSFYCLEYFPSQMLRTG

NNFTFSYTFEDVPFHSSYAHSQSLDRLMNPLIDQYLYYLARTQSTGGTAGT

RELLFSQAGPSNMSAQAKNWLPGPCYRQQRVSKTLSQNNNSNFAWTGATKY

HLNGRDSLVNPGVAMATHKDDEDRFFPSSGVLIFGKQGAGANNTALENVMM

TSEEEIKTTNPVATEQYGVVASNLQSSNTAPVTGTVNSQGALPGMVWQNRD

VYLQGPIWAKIPHTDGNFHPSPLMGGFGLKHPPPQILIKNTPVPANPPAVF
```

-continued

TPAKFASFITQYSTGQVSVEIEWELQKENSKRWNPEIQYTSNYAKSTNVDF
AVDNEGVYSEPRPIGTRYLTRNL.

In other embodiments, a variant AAV capsid protein comprises an amino acid sequence at least 85%, at least 90%, at least 95% or at least 98% identical to a wild-type AAV capsid sequence selected from the group consisting of the ancestral variant disclosed herein as SEQ ID NO:58, comprises one or more amino acid residues selected from the group consisting of: Alanine (A) at 264, Alanine (A) at 266, Serine (S) at 268, Alanine (A) at 448, Threonine (T) at 459, Arginine (R) at 460, Alanine (A) at 467, Serine (S) at 470, Asparagine (N) at 471, Alanine (A) at 474, Serine (S) at 495, Asparagine (D) at 516, Asparagine (D) at 533, Glutamine (Q) at 547, Alanine (A) at 551, Alanine (A) at 555, Glutamic acid (E) at 557, Methionine (M) at 561, Serine (S) at 563, Glutamine (Q) at 577, Serine (S) at 583, Valine (V) at 593, Threonine (T) at 596, Alanine (A) at 661, Valine (V) at 662, Threonine (T) at 664, Proline (P) at 665, Threonine (T) at 710, Aspartic Acid (D) at 717, Asparagine (N) at 718, Glutamic acid (E) at 719, and Serine (S) at 723; and also comprises i) one or more amino acid substitutions selected from the group consisting of P34A, S109T+V708I, A593E+N596D, V708I+V719M, V708I+G727D, S109T+A493V+A593E+V708I, V708I+R733C, Q164K, and I698V and/or (ii) a peptide insertion selected from the group consisting of QADTTKN (SEQ ID NO:13), ISDQTKH (SEQ ID NO:14), ASDSTKA (SEQ ID NO:15), NQDYTKT (SEQ ID NO:16), HDITKNI (SEQ ID NO:17), PQANANEN (SEQ ID NO:63), TNRTSPD (SEQ ID NO:24), PNSTHGS (SEQ ID NO:25), KDRAPST (SEQ ID NO:26), HQDTTKN (SEQ ID NO:19), HPDTTKN (SEQ ID NO:18), NKTTNKD (SEQ ID NO:20), GKSKVID (SEQ ID NO:23), PISNENEH (SEQ ID NO:64), LAQADTTKNA (SEQ ID NO:27), LAISDQTKHA (SEQ ID NO:28), LGISDQTKHA (SEQ ID NO:29), LAASDSTKAA (SEQ ID NO:30), LAHDITKNIA (SEQ ID NO:32), LPQANANENA (SEQ ID NO:37), LANQDYTKTA (SEQ ID NO:31), LATNRTSPDA (SEQ ID NO:39), LAPNSTHGSA (SEQ ID NO:40), LAKDRAPSTA (SEQ ID NO:41), LAHQDTTKNA (SEQ ID NO:34), LAHPDTTKNA (SEQ ID NO:33), LANKTTNKDA (SEQ ID NO:35), LAGKSKVIDA (SEQ ID NO:38), and LPISNENEHA (SEQ ID NO:36). In some embodiments, the variant AAV capsid comprises the specified one or more amino acid substitutions and/or peptide insertions and is otherwise identical to SEQ ID NO:59.

The AAV variants disclosed herein were generated through the use of in vivo directed evolution involving the use of primate retinal screens following intravitreal administration. In some embodiments, the variant capsid proteins disclosed herein, when present in an AAV virion, confer increased transduction of a retinal cell compared to the transduction of the retinal cell by an AAV virion comprising the corresponding parental AAV capsid protein or wild-type AAV. For example, in some embodiments, the variant capsid proteins disclosed herein, when present in an AAV virion, confer more efficient transduction of primate retinal cells than AAV virions comprising the corresponding parental AAV capsid protein or wild-type AAV capsid protein, e.g. the retinal cells take up more AAV virions comprising the subject variant AAV capsid protein than AAV virions comprising the parental AAV capsid protein or wild-type AAV. In some such embodiments, the AAV variant virion or variant rAAV exhibits at least 2-fold, at least 5-fold, at least 10-fold, at least 15-fold, at least 20-fold, at least 25-fold, at least 50-fold, or more than 50-fold, increased transduction of a retinal cell, compared to the transduction of the retinal cell by a wild-type AAV virion or rAAV comprising the corresponding parental AAV capsid protein. In certain such embodiments, the variant capsid proteins disclosed herein, when present in an AAV virion, confer broader transduction of the primate retinal cells than AAV virions comprising the corresponding parental AAV capsid protein or wild type AAV capsid protein. In other words, the variant AAV virion transduces cell types not transduced by virions comprising the corresponding parental AAV capsid protein, and hence more types of cells in the retina than the corresponding parental AAV virion. In some embodiments, the AAV variant virion preferentially transduces a retinal cell, e.g., a subject rAAV virion infects a retinal cell with 2-fold, 5-fold, 10-fold, 15-fold, 20-fold, 25-fold, 50-fold, or more than 50-fold, specificity than another retinal cell or a non-retinal cell, e.g., a cell outside the eye. In some embodiments, the transduced retinal cell is a photoreceptor cell (e.g., rods; cones). In some embodiments, the retinal cell is a retinal ganglion cell (RGC). In some embodiments, the retinal cell is a retinal epithelial cell (RPE cell). In some embodiments, the retinal cell is a Müller glial cell. In some embodiments, the retinal cell is a microglial cell. In some embodiments, the retinal cell is an amacrine cell. In some embodiments, the retinal cell is a bipolar cell. In some embodiments, the retinal cell is a horizontal cell. An increase in transduction of a retinal cell, e.g. increased efficiency of transduction, broader transduction, more preferential transduction, etc. may be readily assessed in vitro or in vivo by any number of methods in the art for measuring gene expression. For example, the AAV may be packaged with a genome comprising an expression cassette comprising a reporter gene, e.g. a fluorescent protein, under the control of a ubiquitous or tissue specific promoter, and the extent of transduction assessed by detecting the fluorescent protein by, e.g., fluorescence microscopy. As another example, the AAV may be packaged with a genome comprising a bar coded nucleic acid sequence, and the extent of transduction assessed by detecting the nucleic acid sequence by, e.g., PCR. As another example, the AAV may be packaged with a genome comprising an expression cassette comprising a therapeutic gene for the treatment of a retinal disease, and the extent of transduction assessed by detecting the treatment of the retinal disease in an afflicted patient that was administered the AAV.

Ocular diseases that can be treated using a variant rAAV vector or virion and/or method disclosed herein include, but are not limited to, monogenic diseases, complex genetic diseases, acquired diseases, and traumatic injuries. Examples of monogenic diseases include, but are not limited to, Bardet-Biedl syndrome; Batten's Disease; Bietti's Crystalline Dystrophy; choroideremia; chorioretinal atrophy; chorioretinal degeneration; cone or cone-rod dystrophies (autosomal dominant, autosomal recessive, and X-linked); congenital stationary night blindness (autosomal dominant, autosomal recessive, and X-linked); disorders of color vision, including achromatopsia (including ACHM2, ACHM3, ACHM4, and ACHM5), protanopia, deuteranopia, and tritanopia; Friedreich's ataxia; Leber's congenital amaurosis (autosomal dominant and autosomal recessive), including, but not limited to, LCA1, LCA2, LCA3, LCA4, LCA6, LCA7, LCA8, LCA12, and LCA15; Leber's Hereditary Optic Neuropathy; macular dystrophy (autosomal dominant and autosomal recessive), including, but not limited to, acute macular degeneration, Best vitelliform macular dystrophy, pattern dystrophy, North Carolina Macular Dystrophy, inherited drusen, Sorsby's fundus dystrophy, malattia levantanese, and genetically-determined retinopathy of prematurity; ocular-retinal developmental disease; ocular albinism; optic atrophies (autosomal dominant, autosomal recessive, and X-linked); retinitis pigmentosa (autosomal dominant, autosomal recessive, X-linked, and mitochondrially-inherited traits), examples of which include RP1, RP2, RP3, RP10, RP20, RP38, RP40, and RP43; X-linked retinoschisis; Stargardt disease; and Usher syndrome, including, but not limited to, USH1B, USH1C, USH1D, USH1F, USH1G, USH2A, USH2C, USH2D, AND USH3. Examples of complex genetic diseases include, but are not limited to, glaucoma (open angle, angle-closure, low-tension, normal-tension, congenital, neovascular, pigmentary, pseudoexfoliation); age-related and other forms of macular degeneration, both exudative and non-exudative forms (autosomal dominant and autosomal recessive), such as acute macular degeneration, vitelliform macular degeneration; retinopathy of prematurity; and Vogt Koyanagi-Harada (VKH) syndrome. Examples of acquired diseases include, but are not limited to, acute macular neuroretinopathy; anterior ischemic optic neuropathy and posterior ischemic optic neuropathy; Behcet's disease; branch retinal vein occlusion; choroidal neovascularization; diabetic retinopathy, including proliferative diabetic retinopathy and associated complications; diabetic uveitis; edema, such as macular edema, cystoid macular edema and diabetic macular edema; epiretinal membrane disorders; macular telangiectasia; multifocal choroiditis; non-retinopathy diabetic retinal dysfunction; ocular tumors; optic atrophies; retinal detachment; retinal disorders, such as central retinal vein occlusion, proliferative vitreoretinopathy (PVR), retinal arterial and venous occlusive disease, vascular occlusion, uveitic retinal disease; uveal effusion; retinal infective and infiltrative disease; optic nerve diseases such as acquired optic atrophy. Examples of traumatic injuries include, but are not limited to, histoplasmosis; optic nerve trauma; ocular trauma which affects a posterior ocular site or location; retinal trauma; viral infection of the eye; viral infection of the optic nerve; a posterior ocular condition caused by or influenced by an ocular laser treatment; posterior ocular conditions caused by or influenced by a photodynamic therapy; photocoagulation, radiation retinopathy; and sympathetic ophthalmia.

In another embodiment, a variant capsid disclosed herein comprises a heterologous nucleic acid comprising a nucleotide sequence encoding a gene product such as, without limitation, an interfering RNA, a long non-coding RNA, a short non-coding RNA, an antisense RNA, an aptamer, a polypeptide, a secreted antibody, a single chain antibody, a $V_{HH}$ domain, a soluble receptor, an affibody, a knottin, a DARPin, a centurin, a chaperone, a site-specific nuclease that provides for site-specific knock-down of gene function or a modified site-specific nuclease that provides for gene-specific activation of transcription.

A rAAV variant virion disclosed herein comprises a heterologous nucleic acid comprising a nucleotide sequence encoding a gene product. In some embodiments, the gene product is an interfering RNA. In some embodiments, the gene product is a long non-coding RNA. In some embodiments, the gene product is a short non-coding RNA. In some embodiments, the gene product is an antisense RNA. In some embodiments, the gene product is an aptamer. In some embodiments, the gene product is a polypeptide. In some embodiments, the gene product is a secreted antibody. In some embodiments, the gene product is a single chain antibody. In some embodiments, the gene product is a $V_{HH}$ domain. In some embodiments, the gene product is a soluble receptor. In some embodiments, the gene product is an affibody. In some embodiments, the gene product is a knottin. In some embodiments, the gene product is a DARPin. In some embodiments, the gene product is a centurin. In some embodiments, the gene product is a chaperone. In some embodiments, the gene product is a site-specific nuclease that provide for site-specific knock-down of gene function.

The uses of the gene product include, but are not limited to, enhancing the level of a factor in a cell, enhancing the level of a factor in a neighboring cell through secretion of a factor, decreasing the level of a factor in a cell, or decreasing the level of a factor in a neighboring cell through secretion of a factor. The gene product can be designed to supplement the level of a defective of missing gene product, decrease the level of a defective of missing gene product, introduce a new supporting gene product, supplement the level of a supporting gene product, decrease the level of a hindering gene product, or both decrease the level of a hindering gene product and introduce or supplement the level of a supporting gene product.

Gene products delivered by the subject AAV variants can be used to alter the level of gene products or gene product activity directly or indirectly linked to retinal diseases and trauma. Genes whose gene products are directly or indirectly linked to genetic diseases include, e.g., ADP-ribosylation factor-like 6 (ARL6); BBSome interacting protein 1 (BBIP1); BBSome protein I (BBS1); BBSome protein 2 (BBS2); BBSome protein 4 (BBS4); BBSome protein 5 (BBS5); BBSome protein 7 (BBS7); BBSome protein 9 (BBS9); BBSome protein 10 (BBS10); BBSome protein 12 (BBS12); centrosomal protein 290 kDa (CEP290); intraflagellar transport protein 172 (IFT172); intraflagellar transport protein 27 (IFT27); inositol polyphosphate-5-phosphatase E (INPP5E); inwardly-rectifying potassium channel subfamily J member 13 (KCNJ13); leucine zipper transcription factor like-1 (LZTFL1); McKusick-Kaufman syndrome protein (MKKS); Meckel syndrome type 1 protein (MKS1); nephronophthisis 3 protein (NPHP1); serologically-defined colon cancer antigen 8 (SDCCAG8); tripartite motif-containing protein 32 (TRIM32); tetratricopeptide repeat domain 8 (TTC8); Batten disease protein (CLN3); cytochrome P450 4V2 (CYP4V2); Rab escort protein 1 (CHM); PR (positive regulatory) domain-containing 13 protein (PRDM13); RPE-retinal G protein-coupled receptor (RGR); TEA domain family member 1 (TEAD1); arylhydrocarbon-interacting receptor protein-like 1 (AIPL1); cone-rod otx-like photoreceptor homeobox transcription factor (CRX); guanylate cyclase activating protein 1A (GUCA1A); retinal-specific guanylate cyclase (GUCY2D); phosphatidylinositol transfer membrane-associated family member 3 (PITPNM3); prominin 1 (PROM1); peripherin (PRPH); peripherin 2 (PRPH2); regulating synaptic membrane exocytosis protein 1 (RIMS1); semaphorin 4A (SEMA4A); human homolog of *C. elegans* unc119 protein (UNC119); ATP-binding cassette transporter—retinal (ABCA4); ADAM metallopeptidase domain 9 (ADAM9); activating transcription factor 6 (ATF6); chromosome 21 open reading frame 2 (C21orf2); chromosome 8 open reading frame 37 (C8orf37); calcium channel; voltage-dependent; alpha 2/delta subunit 4 (CACNA2D4); cadherin-related family member 1 (protocadherin 21) (CDHR1); ceramide kinase-like protein (CERKL); cone photoreceptor cGMP-gated cation channel alpha subunit (CNGA3); cone cyclic nucleotide-gated cation channel beta 3 subunit (CNGB3); cyclin M4 (CNNM4); guanine nucleotide binding protein (G protein); alpha transducing activity polypeptide 2 (GNAT2); potassium channel subfamily V member 2 (KCNV2); Phosphodiesterase 6C (PDE6C); Phosphodiesterase 6H (PDE6H); proteome of centriole 1 centriolar protein B (POC1B); RAB28 member of RAS oncogene family (RAB28); retina and anterior neural fold homeobox 2 transcription factor (RAX2); 11-cis retinol dehydrogenase 5 (RDH5); RP GTPase regulator-interacting protein 1 (RPGRIP1); tubulin tyrosine ligase-like family member 5 (TTLL5); L-type voltage-gated calcium channel alpha-1 subunit (CACNA1F); retinitis pigmentosa GTPase regulator (RPGR); rod transducin alpha subunit (GNAT1); rod cGMP phosphodiesterase beta subunit (PDE6B); rhodopsin (RHO); calcium binding protein 4 (CABP4); G protein-coupled receptor 179 (GPR179); rhodopsin kinase (GRK1); metabotropic glutamate receptor 6 (GRM6); leucine-rich repeat immunoglobulin-like transmembrane domains protein 3 (LRIT3); arrestin (s-antigen) (SAG); solute carrier family 24 (SLC24A1); transient receptor potential cation channel, subfamily M, member 1 (TRPM1); nyctalopin (NYX); green cone opsin (OPN1LW); red cone opsin (OPN1MW); blue cone opsin (OPN1SW); frataxin (FXN); inosine monophosphate dehydrogenase 1 (IMPDH1); orthodenticle homeobox 2 protein (OTX2); crumbs homolog 1 (CRB1); death domain containing protein 1 (DTHD1); growth differentiation factor 6 (GDF6); intraflagellar transport 140 Chlamydomonas homolog protein (IFT140); IQ motif containing B1 protein (IQCB1); lebercilin (LCA5); lecithin retinol acyltransferase (LRAT); nicotinamide nucleotide adenylyltransferase 1 (NMNAT1); RD3 protein (RD3); retinol dehydrogenase 12 (RDH12); retinal pigment epithelium-specific 65 kD protein (RPE65); spermatogenesis associated protein 7 (SPATA7); tubby-like protein 1 (TULP1); mitochondiral genes (KSS, LHON, MT-ATP6, MT-TH, MT-TL1, MT-TP, MT-TS2, mitochondrially encoded NADH dehydrogenases [MT-ND]); bestrophin 1 (BEST1); C1q and tumor necrosis-related protein 5 collagen (CIQTNF5); EGF-containing fibrillin-like extracellular matrix protein 1 (EFEMP1); elongation of very long fatty acids protein (ELOVL4); retinal fascin homolog 2, actin bundling protein (FSCN2); guanylate cyclase activating protein 1B (GUCA1B); hemicentin 1 (HMCN1); interphotoreceptor matrix proteoglycan 1 (IMPG1); retinitis pigmentosa 1-like protein 1 (RP1L1); tissue inhibitor of metalloproteinases-3 (TIMP3); complement factor H (CFH); complement factor D (CFD); complement component 2 (C2); complement component 3 (C3); complement factor B (CFB); DNA-damage regulated autophagy modulator 2 (DRAM2); chondroitin sulfate proteoglycan 2 (VCAN); mitofusin 2 (MFN2); nuclear receptor subfamily 2 group F member 1 (NR2F1); optic atrophy 1 (OPA1); transmembrane protein 126A (TMEM126A); inner mitochondrial membrane translocase 8 homolog A (TIMM8A); carbonic anhydrase IV (CA4); hexokinase 1 (HK1); kelch-like 7 protein (KLHL7); nuclear receptor subfamily 2 group E3 (NR2E3); neural retina lucine zipper (NRL); olfactory receptor family 2 subfamily W member 3 (OR2W3); pre-mRNA processing factor 3 (PRPF3); pre-mRNA processing factor 4 (PRPF4); pre-mRNA processing factor 6 (PRPF6); pre-mRNA processing factor 8 (PRPF8); pre-mRNA processing factor 31 (PRPF31); retinal outer segment membrane protein 1 (ROM1); retinitis pigmentosa protein 1 (RP1); PIM1-kinase associated protein 1 (RP9); small nuclear ribonucleoprotein 200 kDa (SNRNP200); secreted phosphoprotein 2 (SPP2); topoisomerase I binding arginine/serine rich protein (TOPORS); ADP-ribosylation factor-like 2 binding protein (ARL2BP); chromosome 2 open reading frame 71 (C2orf71); clarin-1 (CLRN1); rod cGMP-gated channel alpha subunit (CNGA1); rod cGMP-gated channel beta subunit (CNGB1); cytochrome P450 4V2 (CYP4V2); dehydrodolichyl diphosphate synthetase (DHDDS); DEAH box polypeptide 38 (DHX38); ER membrane protein complex subunit 1 (EMC1); eyes shut/spacemaker homolog (EYS); family with sequence similarity 161 member A (FAM161A); G protein-coupled receptor 125 (GPR125); heparan-alpha-glucosaminide N-acetyltransferase (HGSNAT); NAD(+)-specific isocitrate dehydrogenase 3 beta (IDH3B); interphotoreceptor matrix proteoglycan 2 (IMPG2); KIAA1549 protein (KIAA1549); kizuna centrosomal protein (KIZ); male germ-cell associated kinase (MAK); c-mer protooncogene receptor tyrosine kinase (MERTK); mevalonate kinase (MVK); NIMA (never in mitosis gene A)-related kinase 2 (NEK2); neuronal differentiation protein 1 (NEUROD); cGMP phosphodiesterase alpha subunit (PDE6A); phosphodiesterase 6G cGMP-specific rod gamma (PDE6G); progressive rod-cone degeneration protein (PRCD); retinol binding protein 3 (RBP3); retinaldehyde-binding protein 1 (RLBP1); solute carrier family 7 member 14 (SLC7A14); usherin (USH2A); zinc finger protein 408 (ZNF408); zinc finger protein 513 (ZNF513); oral-facial-digital syndrome 1 protein (OFD1); retinitis pigmentosa 2 (RP2); retinoschisin (RS1); abhydrolase domain containing protein 12 (ABHD12); cadherin-like gene 23 (CDH23); centrosomal protein 250 kDa (CEP250); calcium and integrin binding family member 2 (CIB2); whirlin (DFNB31); monogenic audiogenic seizure susceptibility 1 homolog (GPR98); histidyl-tRNA synthetase (HARS); myosin VIIA (MYO7A); protocadherin 15 (PCDH15); harmonin (USH1C); human homolog of mouse scaffold protein containing ankyrin repeats and SAM domain (USH1G); dystrophin (DMD); norrin (NDP); phosphoglycerate kinase (PGK1); calpain 5 (CAPN5); frizzled-4 Wnt receptor homolog (FZD4); integral membrane protein 2B (ITM2B); low density lipoprotein receptor-related protein 5 (LRP5); micro RNA 204 (MIR204); retinoblastoma protein 1 (RB1); tetraspanin 12 (TSPAN12); chromosome 12 open reading frame 65 (C12orf65); cadherin 3 (CDH3); membrane-type frizzled-related protein (MFRP); ornithine aminotransferase (OAT); phospholipase A2 group V (PLA2G5); retinol-binding protein 4 (RBP4); regulator of G-protein signaling 9 (RGS9); regulator of G-protein signaling 9-binding protein (RGS9BP); ARMS2; excision repair cross-complementing rodent repair deficiency complementation group 6 protein (ERCC6); fibulin 5 (FBLN5); HtrA serine peptidase 1 (HTRA1); toll-like receptor 3 (TLR3); and toll-like receptor 4 (TLR4).

Genes whose gene products induce or promote apoptosis are referred to herein as "pro-apoptotic genes" and the products of those genes (mRNA; protein) are referred to as "pro-apoptotic gene products." Pro-apoptotic targets include, e.g., Bax gene products; Bid gene products; Bak gene products; Bad gene products; Bcl-2; Bcl-X1. Anti-apoptotic gene products include X-linked inhibitor of apoptosis.

Genes whose gene products induce or promote angiogenesis are referred to herein as "pro-angiogenic genes" and the products of those genes (mRNA; protein) are referred to as "pro-angiogenic gene products." Pro-angiogenic targets include, e.g., vascular endothelial growth factor (VEGFa, VEGFb, VEGFc, VEGFd); vascular endothelial growth factor receptor 1 (VEGFR1); vascular endothelial growth factor receptor 2 (VEGFR2); Fms-Related Tyrosine Kinase 1 (Flt1); placenta growth factor (PGF); Platelet-derived growth factor (PDGF); angiopoietins; sonic hedgehog. Genes whose gene products inhibit angiogenesis are referred to herein as "anti-angiogenic genes" and the products of those genes (mRNA; protein) are referred to as "anti-angiogenic gene products." Anti-angiogenic gene products include endostatin; tumstatin; angiostatin; pigment epithelium-derived factor (PEDF), and fusion proteins or antibodies that are specific for pro-angiogenic targets and/or their receptors, e.g. the anti-VEGF fusion proteins sFLT1 or Eylea, the VEGF-specific antibodies Lucentis™ and Avastin™, etc.

Genes whose gene products function as immune modulators, e.g., complement factors, toll-like receptors, are called "immunomodulatory genes". Exemplary immunomodulatory genes include cytokines, chemokines, and the fusion proteins or antibodies that are specific for them and/or their receptors, e.g. the anti-IL -6 fusion protein Rilonacept™, the Complement Factor H-specific antibody lampamizumab, etc. Genes whose gene products function as neuroprotective factors, e.g., platelet derived growth factor receptor (PDGFR); glial derived neurotrophic factor (GDNF); rod-derived con viability factor (RdCVF); fibroblast growth factor (FGF); neurturin (NTN); ciliary neurotrophic factor (CNTF); nerve growth factor (NGF); neurotrophin-4 (NT4); brain derived neurotrophic factor (BDNF); epidermal growth factor. Genes whose gene products function as light responsive opsins, e.g., opsin; rhodopsin; channel rhodopsin; halo rhodopsin.

In some cases, a gene product of interest is a site-specific endonuclease that provide for site-specific knock-down of gene function, e.g., where the endonuclease knocks out an allele associated with a retinal disease. For example, where a dominant allele encodes a defective copy of a gene that, when wild-type, is a retinal structural protein and/or provides for normal retinal function, a site-specific endonuclease can be targeted to the defective allele and knock out the defective allele.

In addition to knocking out a defective allele, a site-specific nuclease can also be used to stimulate homologous recombination with a donor DNA that encodes a functional copy of the protein encoded by the defective allele. Thus, e.g., a subject rAAV virion can be used to deliver both a site-specific endonuclease that knocks out a defective allele, and can be used to deliver a functional copy of the defective allele, resulting in repair of the defective allele, thereby providing for production of a functional retinal protein (e.g., functional retinoschisin, functional RPE65, functional peripherin, etc.). See, e.g., Li et al. (2011) *Nature* 475:217. In some embodiments, a rAAV virion disclosed herein comprises a heterologous nucleotide sequence that encodes a site-specific endonuclease; and a heterologous nucleotide sequence that encodes a functional copy of a defective allele, where the functional copy encodes a functional retinal protein. Functional retinal proteins include, e.g., retinoschisin, RPE65, retinitis pigmentosa GTPase regulator (RGPR)-interacting protein-1, peripherin, peripherin-2, and the like.

Site-specific endonucleases that are suitable for use include, e.g., meganucleases; zinc finger nucleases (ZFNs); transcription activator-like effector nucleases (TALENs); and Clustered regularly interspaced short palindromic repeats/CRISPR-associated (Cas), where such site-specific endonucleases are non-naturally occurring and are modified to target a specific gene. Such site-specific nucleases can be engineered to cut specific locations within a genome, and non-homologous end joining can then repair the break while inserting or deleting several nucleotides. Such site-specific endonucleases (also referred to as "INDELs") then throw the protein out of frame and effectively knock out the gene. See, e.g., U.S. Patent Publication No. 2011/0301073.

In some embodiments of the variant rAAV vector disclosed herein, a nucleotide sequence encoding a gene product of interest is operably linked to a constitutive promoter. Suitable constitutive promoters include e.g. cytomegalovirus promoter (CMV) (Stinski et al. (1985) *Journal of Virology* 55(2): 431-441), CMV early enhancer/chicken β-actin (CBA) promoter/rabbit β-globin intron (CAG) (Miyazaki et al. (1989) *Gene* 79(2): 269-277, $CB^{SB}$ (Jacobson et al. (2006) *Molecular Therapy* 13(6): 1074-1084), human elongation factor 1α promoter (EF1α) (Kim et al. (1990) *Gene* 91(2): 217-223), human phosphoglycerate kinase promoter (PGK) (Singer-Sam et al. (1984) *Gene* 32(3): 409-417, mitochondrial heavy-strand promoter (Loderio et al. (2012) *PNAS* 109(17): 6513-6518), ubiquitin promoter (Wulff et al. (1990) *FEBS Letters* 261: 101-105). In other embodiments, a nucleotide sequence encoding a gene product of interest is operably linked to an inducible promoter. In some instances, a nucleotide sequence encoding a gene product of interest is operably linked to a tissue-specific or cell type-specific regulatory element. For example, in some instances, a nucleotide sequence encoding a gene product of interest is operably linked to a photoreceptor-specific regulatory element (e.g., a photoreceptor-specific promoter), e.g., a regulatory element that confers selective expression of the operably linked gene in a photoreceptor cell. Suitable photoreceptor-specific regulatory elements include, e.g., a rhodopsin promoter; a rhodopsin kinase promoter (Young et al. (2003) *Ophthalmol. Vis. Sci.* 44:4076); a beta phosphodiesterase gene promoter (Nicoud et al. (2007) *J. Gene Med.* 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) *Exp Eye Res.* 55:225), an opsin gene promoter (Tucker et al. (1994) *PNAS* 91:2611-2615), a retinoschisin gene promoter (Park et al. (2009) *Gene Therapy* 16(7): 916-926), a CRX homeodomain protein gene promoter (Furukawa et al. (2002) *The Journal of Neuroscience* 22(5): 1640-1647), a guanine nucleotide binding protein alpha transducing activity polypeptide 1 (GNAT1) gene promoter (Lee et al. (2010) *Gene Therapy* 17:1390-1399), a neural retina-specific leucine zipper protein (NRL) gene promoter (Akimoto et al. (2006) *PNAS* 103(10): 3890-3895), human cone arrestin (hCAR) promoter (Li et al. (2002) *Biochemistry and Molecular Biology* 43: 1375-1383), and the PR2.1, PR1.7, PR1.5, and PR1.1 promoters (Ye et al. (2016) *Human Gene Therapy* 27(1): 72-82)). In some instances, a nucleotide sequence encoding a gene product of interest is operably linked to a retinal pigment epithelia (RPE) cell-specific regulatory element (e.g., a RPE-specific promoter), e.g., a regulatory element that confers selective expression of the operably linked gene in a RPE cell. Suitable RPE-specific regulatory elements include, e.g., an RPE65 gene promoter (Meur et al. (2007) *Gene Therapy* 14: 292-303), a cellular retinaldehyde-binding protein (CRALBP) gene promoter (Kennedy et al. (1998) *Journal of Biological Chemistry* 273: 5591-5598), a pigment epithelium-derived factor (PEDF aka serpin F1) gene promoter (Kojima et al. (2006) *Molecular and Cellular Biochemistry* 293(1-2): 63-69), and a vitelliform macular dystrophy (VMD2) promoter (Esumi et al. (2004) *The Journal of Biological Chemistry* 279(18): 19064-19073). In some instances, a nucleotide sequence encoding a gene product of interest is operably linked to a Müller glia cell-specific regulatory element (e.g., a glial-specific promoter), e.g., a regulatory element that confers selective expression of the operably linked gene in a retinal glial cell. Suitable glial-specific regulatory elements include, e.g., a glial fibrillary acidic protein (GFAP) promoter (Besnard et al. (1991) *Journal of Biological Chemistry* 266(28): 18877-

18883). In some instances, a nucleotide sequence encoding a gene product of interest is operably linked to a bipolar cell-specific regulatory element (e.g., a bipolar-specific promoter), e.g., a regulatory element that confers selective expression of the operably linked gene in a bipolar cell. Suitable bipolar-specific regulatory elements include, e.g., a GRM6 promoter (Cronin et al. (2014) *EMBO Molecular Medicine* 6(9): 1175-1190).

For the purposes of the invention, the disclosure herein provides an isolated nucleic acid comprising a nucleotide sequence that encodes a variant AAV capsid protein as described above. An isolated nucleic acid can be an AAV vector, e.g., a recombinant AAV vector.

The disclosure herein also provides a method of treating a retinal disease, the method comprising administering to an individual in need thereof an effective amount of a rAAV variant virion comprising a transgene of interest as described above and disclosed herein. One of ordinary skill in the art would be readily able to determine an effective amount of the subject rAAV virion and that the disease had been treated by testing for a change in one or more functional or anatomical parameters, e.g. visual acuity, visual field, electrophysiological responsiveness to light and dark, color vision, contrast sensitivity, anatomy, retinal health and vasculature, ocular motility, fixation preference, and stability.

Nonlimiting methods for assessing retinal function and changes thereof include assessing visual acuity (e.g. best-corrected visual acuity [BCVA], ambulation, navigation, object detection and discrimination), assessing visual field (e.g. static and kinetic visual field perimetry), performing a clinical examination (e.g. slit lamp examination of the anterior and posterior segments of the eye), assessing electrophysiological responsiveness to all wavelengths of light and dark (e.g. all forms of electroretinography (ERG) [full-field, multifocal and pattern], all forms of visual evoked potential (VEP), electrooculography (EOG), color vision, dark adaptation and/or contrast sensitivity). Nonlimiting methods for assessing anatomy and retinal health and changes thereof include Optical Conherence Tomography (OCT), fundus photography, adaptive optics scanning laser ophthalmoscopy (AO-SLO), fluorescence and/or autofluorescence; measuring ocular motility and eye movements (e.g. nystagmus, fixation preference, and stability), measuring reported outcomes (patient-reported changes in visual and non-visually-guided behaviors and activities, patient-reported outcomes [PRO], questionnaire-based assessments of quality-of-life, daily activities and measures of neurological function (e.g. functional Magnetic Resonance Imaging (MRI)).

In some embodiments, an effective amount of the subject rAAV virion results in a decrease in the rate of loss of retinal function, anatomical integrity, or retinal health, e.g. a 2-fold, 3-fold, 4-fold, or 5-fold or more decrease in the rate of loss and hence progression of disease, for example, a 10-fold decrease or more in the rate of loss and hence progression of disease. In some embodiments, the effective amount of the subject rAAV virion results in a gain in visual function, retinal function, an improvement in retinal anatomy or health, and/or an improvement in ocular motility and/or improvement in neurological function, e.g. a 2-fold, 3-fold, 4-fold or 5-fold improvement or more in retinal function, retinal anatomy or health, and/or improvement in ocular motility, e.g. a 10-fold improvement or more in retinal function, retinal anatomy or health, and/or improvement in ocular motility. As will be readily appreciated by the ordinarily skilled artisan, the dose required to achieve the desired treatment effect will typically be in the range of $1 \times 10^8$ to about $1 \times 10^{15}$ recombinant virions, typically referred to by the ordinarily skilled artisan as $1 \times 10^8$ to about $1 \times 10^{15}$ "vector genomes".

A subject rAAV virion can be administered via intraocular injection, for example by intravitreal injection, by subretinal injection, by suprachoroidal injection, or by any other convenient mode or route of administration that will result in the delivery of the rAAV virion to the eye. Other convenient mancestodes or routes of administration include, without limitation, intravenous, intra-arterial, peri-ocular, intracameral, subconjunctival and sub-tenons injections and topical administration and intranasal. When administered via intravitreal injection, the subject rAAV virion is able to move through the vitreous and traverse the internal limiting membrane (also referred to herein as an inner limiting membrane, or "ILM"; a thin, transparent acellular membrane on the surface of the retina forming the boundary between the retina and the vitreous body, formed by astrocytes and the end feet of Müller cells), and/or moves through the layers of the retina more efficiently, compared to the capability of an AAV virion comprising the corresponding parental AAV capsid protein.

A variant capsid protein disclosed herein is isolated, e.g., purified. In some embodiments, a variant capsid protein disclosed herein is included in an AAV vector or a recombinant AAV (rAAV) virion. In other embodiments, such AAV variant vectors and/or AAV variant virions are used in an in vivo or ex vivo method of treating ocular disease in the primate retina.

The disclosure herein further provides host cells such as, without limitation, isolated (genetically modified) host cells comprising a subject nucleic acid. A host cell according to the invention disclosed herein, can be an isolated cell, such as a cell from an in vitro cell culture. Such a host cell is useful for producing a subject rAAV variant virion, as described herein. In one embodiment, such a host cell is stably genetically modified with a nucleic acid. In other embodiments, a host cell is transiently genetically modified with a nucleic acid. Such a nucleic acid is introduced stably or transiently into a host cell, using established techniques, including, but not limited to, electroporation, calcium phosphate precipitation, liposome-mediated transfection, and the like. For stable transformation, a nucleic acid will generally further include a selectable marker, e.g., any of several well-known selectable markers such as neomycin resistance, and the like. Such a host cell is generated by introducing a nucleic acid into any of a variety of cells, e.g., mammalian cells, including, e.g., murine cells, and primate cells (e.g., human cells). Exemplary mammalian cells include, but are not limited to, primary cells and cell lines, where exemplary cell lines include, but are not limited to, 293 cells, COS cells, HeLa cells, Vero cells, 3T3 mouse fibroblasts, C3H10T1/2 fibroblasts, CHO cells, and the like. Exemplary host cells include, without limitation, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. A host cell can also be made using a baculovirus to infect insect cells such as Sf9 cells, which produce AAV (see, e.g., U.S. Pat. No. 7,271,002; U.S. patent application Ser. No. 12/297,958). In some embodiments, a genetically modified host cell includes, in addition to a nucleic acid comprising a nucleotide sequence encoding a variant AAV capsid protein, as described above, a nucleic acid that comprises a nucleotide sequence encoding one or more AAV rep proteins. In other embodiments, a host cell further comprises an rAAV variant vector. An rAAV variant virion can be generated using such host cells. Methods of generating an rAAV virion are described in, e.g., U.S. Patent Publication No. 2005/0053922 and U.S. Patent Publication No. 2009/0202490.

The disclosure herein additionally provides a pharmaceutical composition comprising: a) the rAAV variant virion, as described above and disclosed herein; and b) a pharmaceutically acceptable carrier, diluent, excipient, or buffer. In some embodiments, the pharmaceutically acceptable carrier, diluent, excipient, or buffer is suitable for use in a human or non-human patient. Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, surfactants, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc. In some aspects of the present invention, the present invention provides a pharmaceutical composition comprising about $1 \times 10^8$ to about $1 \times 10^{15}$ recombinant viruses or $1 \times 10^8$ to about $1 \times 10^{15}$ vector genomes, wherein each said recombinant virus comprises a genome encoding one or more gene products.

The following examples are set forth to provide the ordinarily skilled artisan with a complete disclosure and description for guidance as to how to make and use the variant AAV capsids disclosed herein, and are not intended to limit the scope of the invention disclosed herein. In addition, the following examples are not intended to represent that the experiments below are all or the only experiments performed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Example 1

Intravitreal Injection and Tissue Harvesting. A single male cynomolgus macaque (*Macaca fascicularis*) age 4-10 years old and weighing at least 4 kg was dosed via intravitreal injection through the sclera (approximately 3 mm behind the limbus using a procedure and delivery device suitable for human use). The animal was anesthetized and given the topical anesthetic 100 μL of the library was administered to each eye Euthanasia was performed by trained veterinary staff using 100 mg/kg pentobarbital sodium intravenous injection on day 14±3. Eyes were nucleated and stored at 4° C. until dissection.

Figure 2:
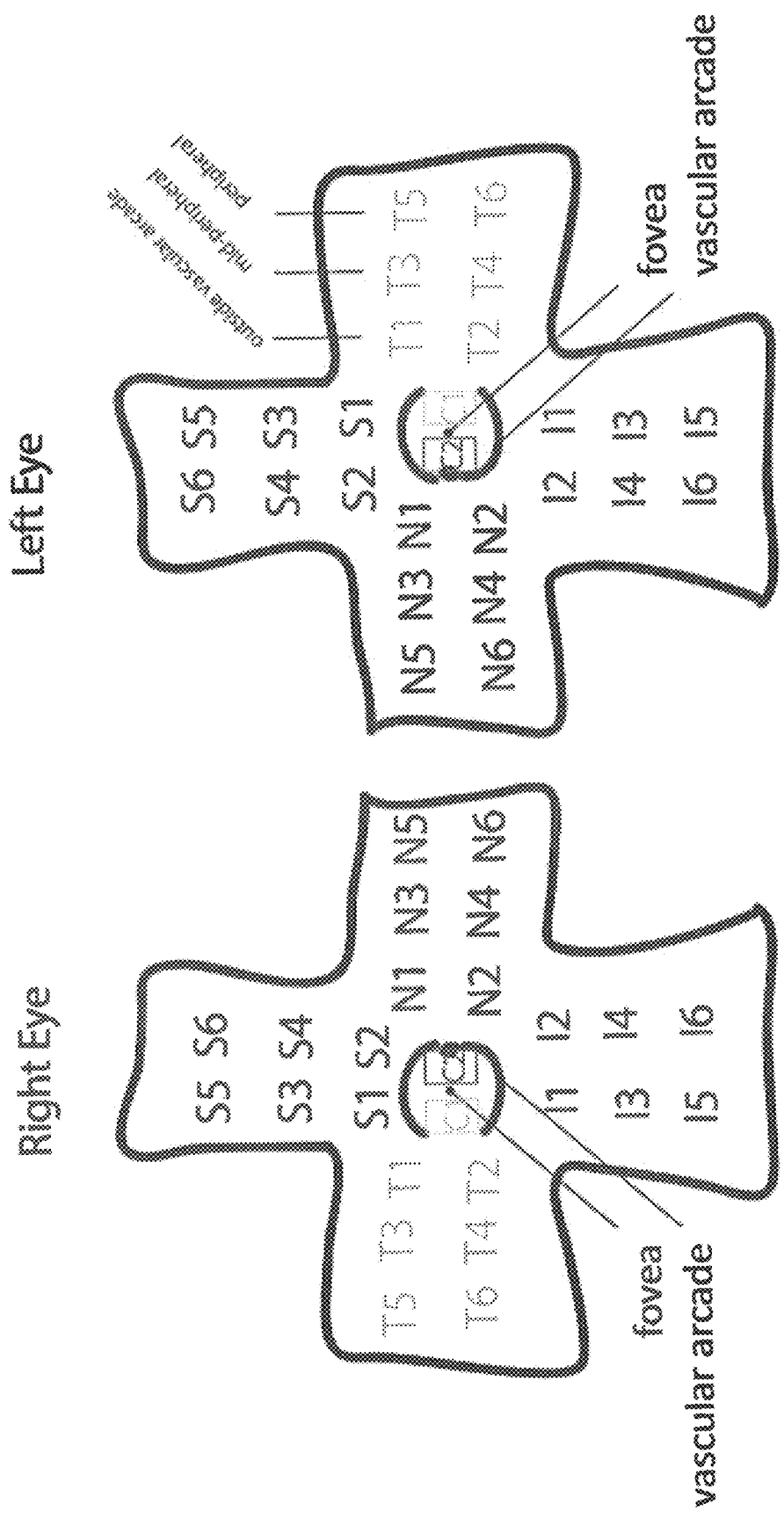
FIG. 2 provides a retinal flat mount schematic showing where samples from which viral genomes are amplified, are collected across a broad area of the retina.

Tissue Dissection. Eyes were cut along the *Ora serrata* with a scalpel, and the anterior segment was removed. Relief cuts were made into the retina around the fovea to enable flat mounting of the retina, and the vitreous was removed. Six samples of the retina from each quadrant (superior, inferior, nasal, and temporal) were collected, as shown in FIG. 2, and cellular material corresponding to RPE cells, photoreceptors, biopolar cells, amacrine cells, horizontal cells, and/or ganglion cells was isolated.

Directed Evolution. The directed evolution process is shown in FIG. 1A-1E. Briefly, a viral capsid library comprising 20+ proprietary combinations of DNA mutation technique and cap genes is created (FIG. 1A). Viruses are then packaged (FIG. 1B)—such that each particle is composed of a mutant capsid surrounding the cap gene encoding that capsid—and purified. The capsid library is placed under selective pressure in vivo. The tissue or cellular material of interest is harvested to isolate AAV variants that have successfully infected that target, and the successful viruses are recovered. Successful clones are enriched through repeated selection (Stage 1—FIG. 1D). Selected cap genes then undergo proprietary re-diversification and are enriched through further selection steps to iteratively increase viral fitness (Stage 2—FIG. 1D). Variants identified during Vector Selection Stages 1 and 2 demonstrate the ability to transduce primate retina cells (FIG. 1E).

Figure 3:
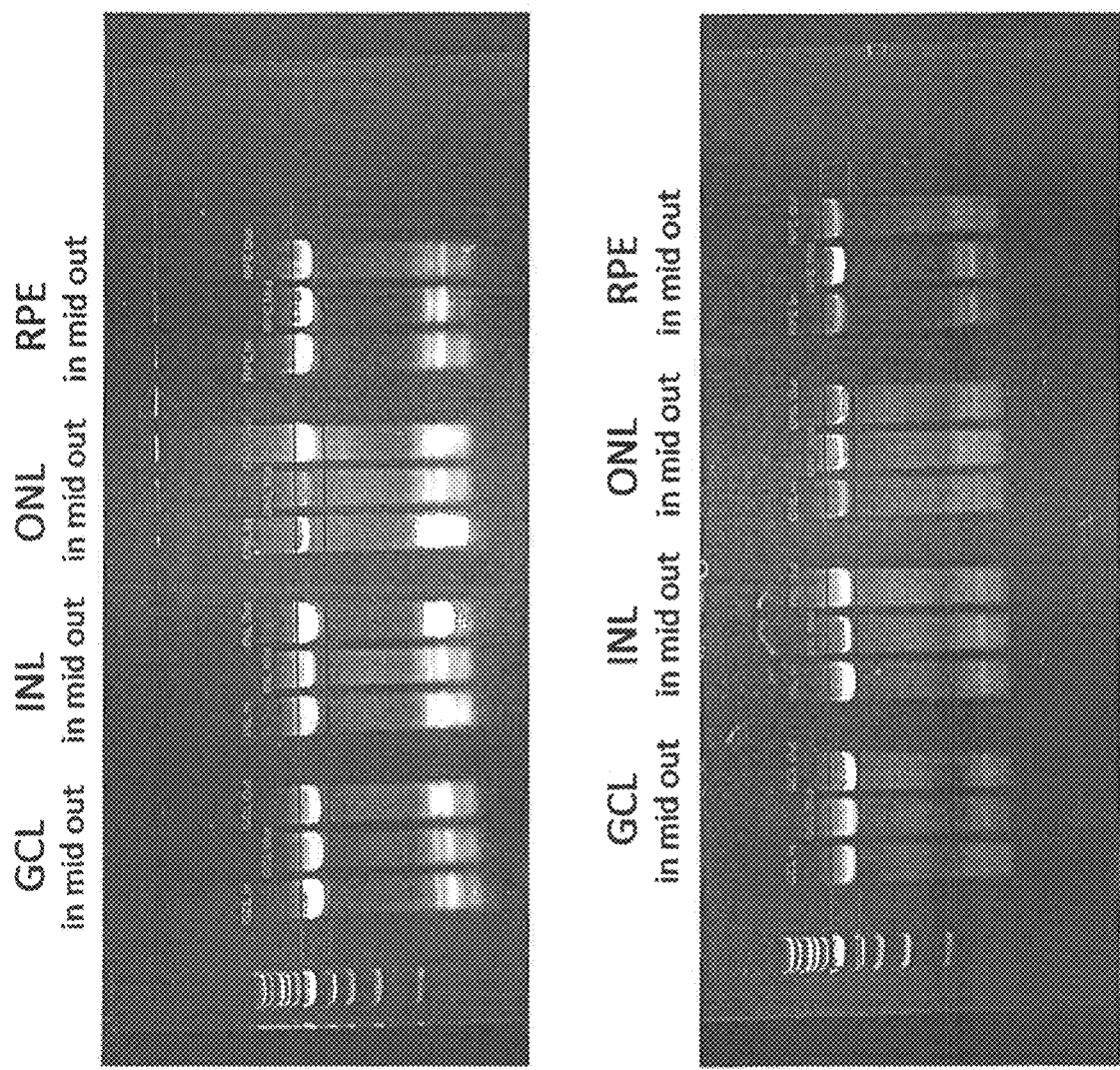
FIG. 3 shows a PCR amplification of viral genomes from the ganglion cell layer (GCL), inner nuclear layer (INL), photoreceptor/outer nuclear layer (ONL), and retinal pigment epithelia (RPE) layer retinal tissue from a representative round of selection. Both the right eye (top image) and left eye (bottom image) were injected with library. Inner retina (in), middle retina (mid), and outer/peripheral retina (out) were sampled. Bands within red boxes represent successful amplification of viral genomes.
Figure 5:
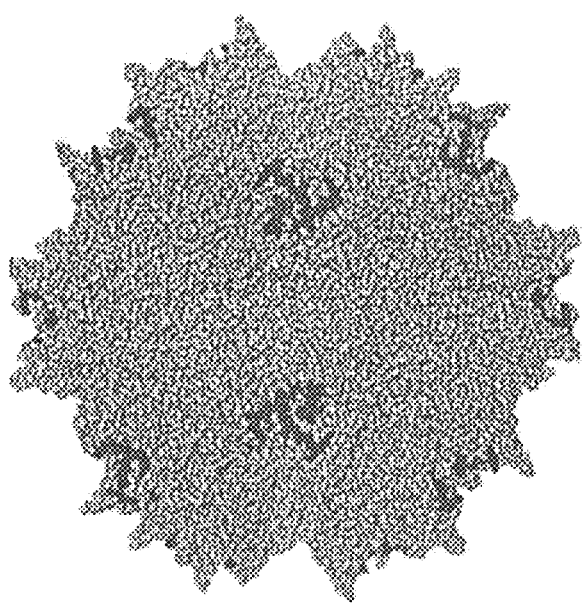
FIG. 5 provides a representative three-dimensional model of AAV2 containing a random heptamer following amino acid 587.

Successful Recovery of AAV Capsid Genomes: Rounds 1-6. The capsids recovered from each round of selection were used to package the library injected to initiate the subsequent round of selection. Recovery of capsid genes from tissue represents successful internalization of library vectors into the tissue of interest. Following Round 4, additional re-diversification of the library was incorporated prior to library packaging and injection for Round 5. Recovery of viral genomes from RPE, PR, inner nuclear layer (INL), and ganglion cell layer (GCL) retinal tissue from a representative round of selection are shown in FIG. 3. Bands within boxes represent successful recovery of viral genomes.

Sequencing Analysis: Rounds 3-6. During rounds 3-6, sequencing was performed on individual clones within the library to determine the frequency of variants within the population. Variants were evaluated for the presence of motifs within the sequencing data. Variants were grouped into motifs based on the presence of a unifying variation (for example, a specific point mutation or specific peptide insertion sequence in a consistent location within the capsid) that occurred in multiple sequences. Motifs representing at least 5% of the sequenced population in two or more rounds of the selection or at least 10% of the sequenced population in one or more rounds of the selection are represented in FIG. 4A (Round 3 sequencing analysis), 4B (Round 4 sequencing analysis), 4C (Round 5 sequencing analysis), and 4D (Round 6 sequencing analysis).

Several representative clones that were identified as conferring increased infectivity of retinal cells are listed in Table 1 below (each clone contains the identified substitution(s) and/or peptide insertion and is otherwise identical to SEQ ID NO:2; the selection round, number of sequences and frequency (in parentheses) are listed for each clone):

TABLE 1

Amino acid sequence modifications to the AAV VP1 capsid protein that confer increased infectivity of one or more cells of the retina. Substitutions listed in column 2 are based on the amino acid sequence for wild type AAV2, i.e. in the absence of inserted peptide.

| Insertion | Substitution | Pan-Retinal | RPE | Photoreceptor |
|---|---|---|---|---|
| 588~LAISDQTKHA~ (SEQ ID NO: 28) | None | Round 4, 5, 6 | Round 3, 5, 6 | Round 4, 5 |
| 588~LAISDQTKHA~ (SEQ ID NO: 28) | +M1L+L15P +P535S | Round 6 1 (1.61%) | | |
| 588~LAISDQTKHA~ (SEQ ID NO: 28) | +P34A | Round 5 1 (1.89%) | | |
| 588~LAISDQTKHA~ (SEQ ID NO: 28) | +P34A+S731L | | | Round 5 1 (1.82%) |
| 588~LAISDQTKHA~ (SEQ ID NO: 28) | +N57D | Round 4 1 (1.33%) | | |
| 588~LAISDQTKHA~ (SEQ ID NO: 28) | +N66K | | | Round 5 1 (1.82%) |
| 588~LAISDQTKHA~ (SEQ ID NO: 28) | +R81Q | Round 6 1 (1.61%) | | |
| 588~LAISDQTKHA~ (SEQ ID NO: 28) | +Q101R | | | Round 4 1 (2.27%) |
| 588~LAISDQTKHA~ (SEQ ID NO: 28) | +S109T | Round 3 1 (1.85%) | | |
| 588~LAISDQTKHA~ (SEQ ID NO: 28) | +R144K | | | Round 5 1 (1.82%) |
| 588~LAISDQTKHA~ (SEQ ID NO: 28) | +R144M | | | Round 5 1 (1.82%) |
| 588~LAISDQTKHA~ (SEQ ID NO: 28) | +Q164K | | | Round 4 1 (2.27%) |
| 588~LAISDQTKHA~ (SEQ ID NO: 28) | +Q164K+V708I | Rounds 3 and 4 2 (3.7%) 1 (1.33%) | | |
| 588~LAISDQTKHA~ (SEQ ID NO: 28) | +T176P | Round 4 1 (1.33%) | | |
| 588~LAISDQTKHA~ (SEQ ID NO: 28) | +L188I | | Round 5 1 (2.27%) | |
| 588~LAISDQTKHA~ (SEQ ID NO: 28) | +S196Y | Round 4 1 (1.33%) | | |
| 588~LAISDQTKHA~ (SEQ ID NO: 28) | +G226E | | | Round 4 1 (2.27%) |
| 588~LAISDQTKHA~ (SEQ ID NO: 28) | +G236V | Round 4 1 (1.33%) | | |

TABLE 1-continued Amino acid sequence modifications to the AAV VPI capsid protein that confer increased infectivity of one or more cells of the retina. Substitutions listed in column 2 are based on the amino acid sequence for wild type AAV2, i.e. in the absence of inserted peptide.

| Insertion | Substitution | Pan-Retinal | RPE | Photoreceptor |
|---|---|---|---|---|
| 588~LAISDQTKHA~ (SEQ ID NO: 28) | +I240T | Round 3 1 (1.85%) | | |
| 588~LAISDQTKHA~ (SEQ ID NO: 28) | +N312K | Round 4 1 (1.33%) | | |
| 588~LAISDQTKHA~ (SEQ ID NO: 28) | +P363L | Round 6 1 (1.61%) | | |
| 588~LAISDQTKHA~ (SEQ ID NO: 28) | +T456K | Round 6 1 (1.61%) | | |
| 588~LAISDQTKHA~ (SEQ ID NO: 28) | +I698V | Round 5 1 (1.89%) | | |
| 588~LAISDQTKHA~ (SEQ ID NO: 28) | +V708I | Round 4, 5, 6 | Round 3, 4, 5 | Round 4, 5 |
| 588~LAISDQTKHA~ (SEQ ID NO: 28) | +V708I+R484C | | Round 5 1 (2.27%) | |
| 588~LAISDQTKHA~ (SEQ ID NO: 28) | N312K+N449D+ N551S+I698V+L735Q | Engineered | | Engineered |
| 588~LGISDQTKHA~ (SEQ ID NO: 29) | None | Round 5 1 (1.89%) | | |
| 588~LAQADTTKNA~ (SEQ ID NO: 27) | None | Round 3, 4, 5, 6 | Round 3, 4, 5 | Round 4, 5 |
| 588~LAQADTTKNA~ (SEQ ID NO: 27) | +E36D | | Round 5 1 (2.27%) | |
| 588~LAQADTTKNA~ (SEQ ID NO: 27) | +P250S | Round 6 1 (1.61%) | | |
| 588~LAQADTTKNA~ (SEQ ID NO: 27) | +A524T | Round 3 1 (1.85%) | | |
| 588~LAQADTTKNA~ (SEQ ID NO: 27) | +A593E | Round 4 1 (1.33%) | | |
| 588~LAQADTTKNA~ (SEQ ID NO: 27) | +I698V | Rounds 5 and 6 1 (1.61%) 1 (1.89%) | | |
| 588~LAQADTTKNA~ (SEQ ID NO: 27) | +V708I | Round 3, 4, 5, 6 | Round 3, 4, 5 | |
| 588~LAQADTTKNA~ (SEQ ID NO: 27) | +V708I+V719M | | Rounds 3 and 4 1 (2.08%) 2 (4.55%) | |
| 588~LAQADTTKNA~ (SEQ ID NO: 27) | +V719M | | Round 4 1 (2.27%) | |
| 588~LAHQDTTKNA~ (SEQ ID NO: 34) | None | Round 5 2 (3.77%) | | |
| 588~LANQDYTKTA~ (SEQ ID NO: 31) | None | Rounds 3, 4 and 5 5 (9.26%) 1 (1.33%) 3 (5.66%) | Rounds 3, 4 and 5 2 (4.17%) 2 (4.55%) 2 (2.27%) | Round 5 1 (1.82%) |

TABLE 1-continued

Amino acid sequence modifications to the AAV VPI capsid protein that confer increased infectivity of one or more cells of the retina. Substitutions listed in column 2 are based on the amino acid sequence for wild type AAV2, i.e. in the absence of inserted peptide.

| Insertion | Substitution | Pan-Retinal | RPE | Photoreceptor |
|---|---|---|---|---|
| 588~LANQDYTKTA~ (SEQ ID NO: 31) | +S109T+S463Y | Round 3 1 (1.85%) | | |
| 588~LANQDYTKTA~ (SEQ ID NO: 31) | +D368H | Round 3 1 (1.85%) | | |
| 588~LANQDYTKTA~ (SEQ ID NO: 31) | +V708I | Round 4 1 (1.33%) | Round 3 1 (2.08%) | |
| 588~LAHDITKNIA~ (SEQ ID NO: 32) | None | Rounds 3, 4 5 and 6 1 (1.85%) 1 (1.33%) 1 (1.89%) 2 (3.23%) | | |
| 588~LAHDITKNIA~ (SEQ ID NO: 32) | +S109T | Round 4 1 (1.33%) | | |
| 588~LAHDITKNIA~ (SEQ ID NO: 32) | +R389S | Round 5 1 (1.89%) | | |
| 588~LAHDITKNIA~ (SEQ ID NO: 32) | +A593E | Round 3 1 (1.85%) | | |
| 588~LAHDITKNIA~ (SEQ ID NO: 32) | +V708I | Round 4, 5 | | |
| 588~IAHDITKNIA~ (SEQ ID NO: 60) | +V708I | | Round 3 1 (2.08%) | |
| 588~LAPNSTHGSA~ (SEQ ID NO: 40) | +V708I | Round 3 1 (1.85%) | | |
| 588~LANKTTNKDA~ (SEQ ID NO: 35) | None | | Round 5 1 (2.27%) | |
| 588~LANKTTNKDA~ (SEQ ID NO: 35) | +N449D | | | Round 4 1 (2.17%) |
| 588~LAHPDTTKNA~ (SEQ ID NO: 33) | | Round 6 1 (1.61%) | | |
| 588~LATNRTSPDA~ (SEQ ID NO: 39) | | Round 6 1 (1.61%) | | |
| 588~LPQANANENA~ (SEQ ID NO: 37) | | Round 5 1 (1.89%) | | |
| 588~LAASDSTKAA~ (SEQ ID NO: 30) | | Rounds 3 and 4 1 (1.85%) 1 (1.33%) | | |
| 588~LAKDRAPSTA~ (SEQ ID NO: 41) | | Round 3 1 (1.85%) | | |
| 588~LPISNENEHA~ (SEQ ID NO: 36) | | | | Round 4 1 (2.17%) |
| 588~LAGKSKVIDA~ (SEQ ID NO: 38) | | | | Round 5 1 (1.82%) |
| NONE | P34A | Round 5 1 (1.89%) | Rounds 4, 5 3 (6.82%) 1 (2.27%) | Round 4 1 (2.17%) |

TABLE 1-continued

Amino acid sequence modifications to the AAV VP1 capsid protein that confer increased infectivity of one or more cells of the retina. Substitutions listed in column 2 are based on the amino acid sequence for wild type AAV2, i.e. in the absence of inserted peptide.

| Insertion | Substitution | Pan-Retinal | RPE | Photoreceptor |
|---|---|---|---|---|
| NONE | P64S | Round 3<br>1 (1.85%) | Round 4<br>1 (2.27%) | |
| NONE | S109T | Round 4<br>2 (2.67%) | Rounds 3, 4, 5<br>4 (8.33%)<br>1 (2.27%)<br>1 (2.27%) | |
| NONE | S109T+P8L | | Round 3<br>1 (2.08%) | |
| NONE | S109T+Q120R | | Round 3<br>1 (2.08%) | |
| NONE | S109T+A493V+A593E+V708I | Round 3<br>1 (1.85%) | | |
| NONE | Q164K | Rounds 4 and 5<br>2 (2.67%)<br>1 (1.89%) | Round 4<br>1 (2.27%) | |
| NONE | Q175H | Round 3<br>1 (1.85%) | | Round 4<br>1 (2.17%) |
| NONE | S196Y | Round 3<br>1 (1.85%) | Round 4<br>1 (2.27%) | |
| NONE | A593E | Rounds 3, 4, 5<br>3 (5.56%)<br>7 (9.33%)<br>1 (1.89%) | Rounds 3, 4, 5<br>12 (25%)<br>7 (15.9%)<br>14 (31.8%) | Round 4<br>1 (2.17%) |
| NONE | A593E+Q464R | | Round 3<br>1 (2.08%) | |
| NONE | A593E+N596D | | Round 4<br>1 (2.27%) | |
| NONE | A593E+N596D+T491A | | Round 3<br>2 (4.17%) | |
| NONE | A593E+V708I | Rounds 3, 4<br>2 (3.7%)<br>2 (2.67%) | Rounds 3, 4, 5<br>4 (8.33%)<br>1 (2.27%)<br>1 (2.27%) | |
| NONE | I698V | Round 5<br>1 (1.89%) | Round 5<br>1 (2.27%) | |
| NONE | V708I | Rounds 3, 4<br>2 (3.7%)<br>5 (6.67%) | Rounds 3, 4, 5<br>1 (2.08%)<br>4 (9.09%)<br>4 (9.09%) | |
| NONE | V708I+V719M | | Round 4<br>2 (4.55%) | |
| NONE | V708I+G727D | | Round 5<br>1 (2.27%) | |
| NONE | V708I+R733C | | | Round 4<br>1 (2.17%) |

Also identified as a capsid having increased infectivity of one or more cells of the retina was a clone having the following ancestral VP1 capsid sequence:

(SEQ ID NO: 59)
```
MAADGYLPDWLEDNLSEGIREWWDLKPGAPKPKANQQKQDDGRGLVLPGYK

YLGPFNGLDKGEPVNAADAAALEHDKAYDQQLKAGDNPYLRYNHADAEFQE

RLQEDTSFGGNLGRAVFQAKKRVLEPLGLVEEGAKTAPGKKRPVEPSPQRS

PDSSTGIGKKGQQPAKKRLNFGQTGDSESVPDPQPLGEPPAGPSGLGSGTM

AAGGGAPMADNNEGADGVGNASGNWHCDSTWLGDRVITTSTRTWALPTYNN

HLYKQISSASAGSTNDNHYFGYSTPWGYFDFNRFHCHFSPRDWQRLINNNW

GFRPKRLNFKLFNIQVKEVTTNDGVTTIANNLTSTVQVFSDSEYQLPYVLG

SAHQGCLPPFPADVFMIPQYGYLTLNNGSQAVGRSSFYCLEYFPSQMLRTG

NNFTFSYTFEDVPFHSSYAHSQSLDRLMNPLIDQYLYYLARTQSTGGTAGT

RELLFSQAGPSNMSAQAKNWLPGPCYRQQRVSKTLSQNNNSNFAWTGATKY

HLNGRDSLVNPGVAMATHKDDEDRFFFSSGVLIFGKQGAGANNTALENVMM

TSEEEIKTTNPVATEQYGVVASNLQSSNTAPVTGTVNSQGALPGMVWQNRD

VYLQGPIWAKIPHTDGNFHPSPLMGGFGLKHPPPQILIKNTPVPANPPAVF

TPAKFASFITQYSTGQVSVEIEWELQKENSKRWNPEIQYTSNYAKSTNVDF

AVDNEGVYSEPRPIGTRYLTRNL.
```

This ancestral capsid variant is evolved from the ancestral capsid SEQ ID NO:58, in which the positions of degeneracy (residues 264, 266, 268, 448, 459, 460, 467, 470, 471, 474, 495, 516, 533, 547, 551, 555, 557, 561, 563, 577, 583, 593, 596, 661, 662, 664, 665, 710, 717, 718, 719, 723) evolved to comprise Alanine (A) at 264, Alanine (A) at 266, Serine (S) at 268, Alanine (A) at 448, Threonine (T) at 459, Arginine (R) at 460, Alanine (A) at 467, Serine (S) at 470, Asparagine (N) at 471, Alanine (A) at 474, Serine (S) at 495, Asparagine (D) at 516, Asparagine (D) at 533, Glutamine (Q) at 547, Alanine (A) at 551, Alaninet (A) at 555, Glutamic acid (E) at 557, Methionine (M) at 561, Serine (S) at 563, Glutamine (Q) at 577, Serine (S) at 583, Valine (V) at 593, Threonine (T) at 596, Alanine (A) at 661, Valine (V) at 662, Threonine (T) at 664, Proline (P) at 665, Threonine (T) at 710, Aspartic Acid (D) at 717, Asparagine (N) at 718, Glutamic acid (E) at 719, and Serine (S) at 723.

The AAV variant virions disclosed herein may incorporate reasonable rational design parameters, features, modifications, advantages, and variations that are readily apparent to those skilled in the art in the field of engineering AAV viral vectors.

Example 2

Directed evolution was employed to discover novel adeno-associated virus (AAV) variants with superior gene delivery to retinal cells following intravitreal (IVT) administration, a route of administration with significant advantages over other methods of gene delivery to the human eye (Example 1). The cell tropism following intravitreal administration of the novel AAV variant comprising a P34A substitution and the peptide LAISDQTKHA (SEQ ID NO:28) inserted at amino acid 588 (LAISDQTKHA+P34A) was assessed in vivo in non-human primates (NHP) as a representative example of the ability of ISDQTKH (SEQ ID NO:14)-containing AAV variants to transduce retinal cells.

Recombinant AAV virions comprising either an AAV2 capsid or the novel variant capsid LAISDQTKHA+P34A and a genome comprising a green fluorescent protein (GFP) transgene operably linked to a CMV promoter (AAV2.CMV.GFP and LAISDQTKHA+P34A.CMV.GFP, respectively) or a CAG promoter (AAV2.CAG.EGFP and LAISDQTKHA+P34A.CAG.EGFP, respectively) were manufactured using standard methods. African Green Monkeys (FIGS. 7, 8) or Cynomolgus macaques (FIG. 9) were injected intravitreally with various doses of vector ranging from $4\times10^{10}$ vg to $1\times10^{12}$ 1e12 vg per eye (see figure legends for details) and the transduction of retinal cells was assessed in life by fundus fluorescence imaging with a Heidelberg Spectralis™.

Figure 7:
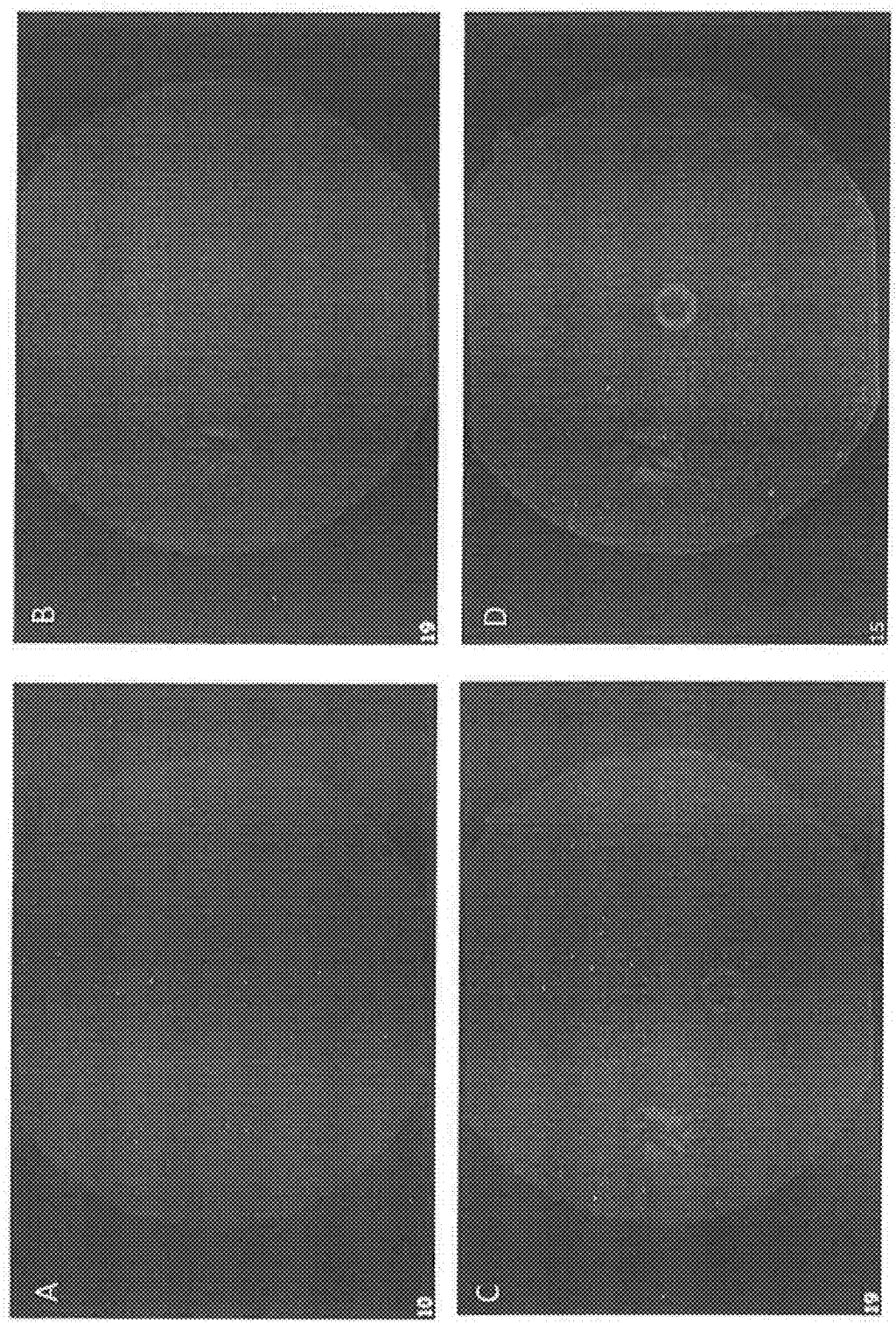
FIG. 7 provides fundus fluorescence images taken with a Heidelberg Spectralis™ of the retina of an African Green monkey following intravitreal administration of $2\times10^{11}$ vector genomes (vg) of AAV2 delivering a GFP transgene under the control of the CMV promoter (AAV2.CMV.GFP). Images were taken at baseline (A) and at 14 days (B), 28 days (C), and 42 days (D) after injection.
Figure 8:
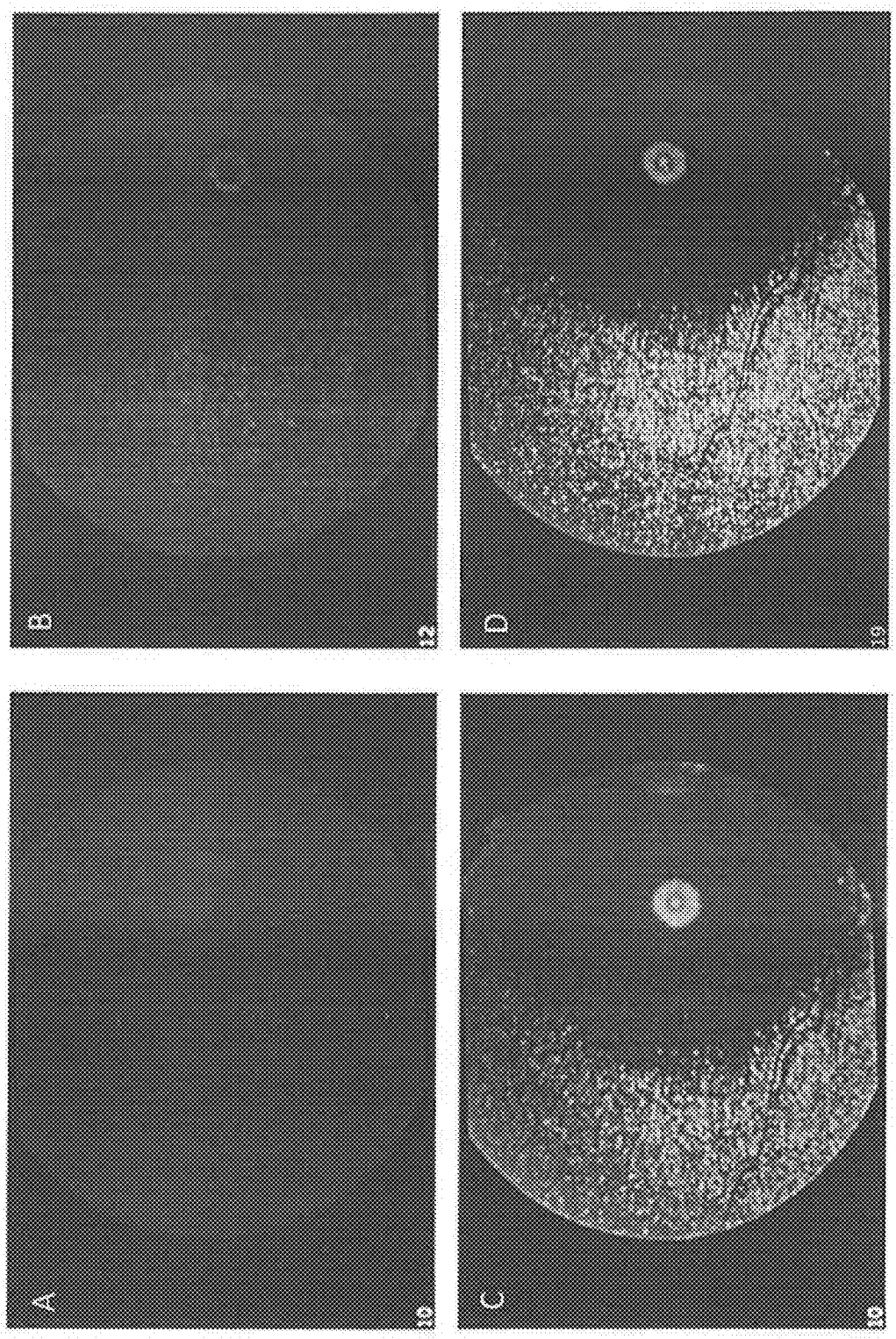
FIG. 8 provides fundus fluorescence images taken with a Heidelberg Spectralis™ the retina of an African Green monkey following intravitreal administration of $2\times10^{11}$ vector genomes (vg) of the novel AAV variant LAISDQTKHA+P34A delivering a GFP transgene under the control of the CMV promoter (LAISDQTKHA+P34A.CMV.GFP). Images taken at baseline (A) and at 14 days (B), 28 days (C), and 42 days (D) after injection.
Figure 9:
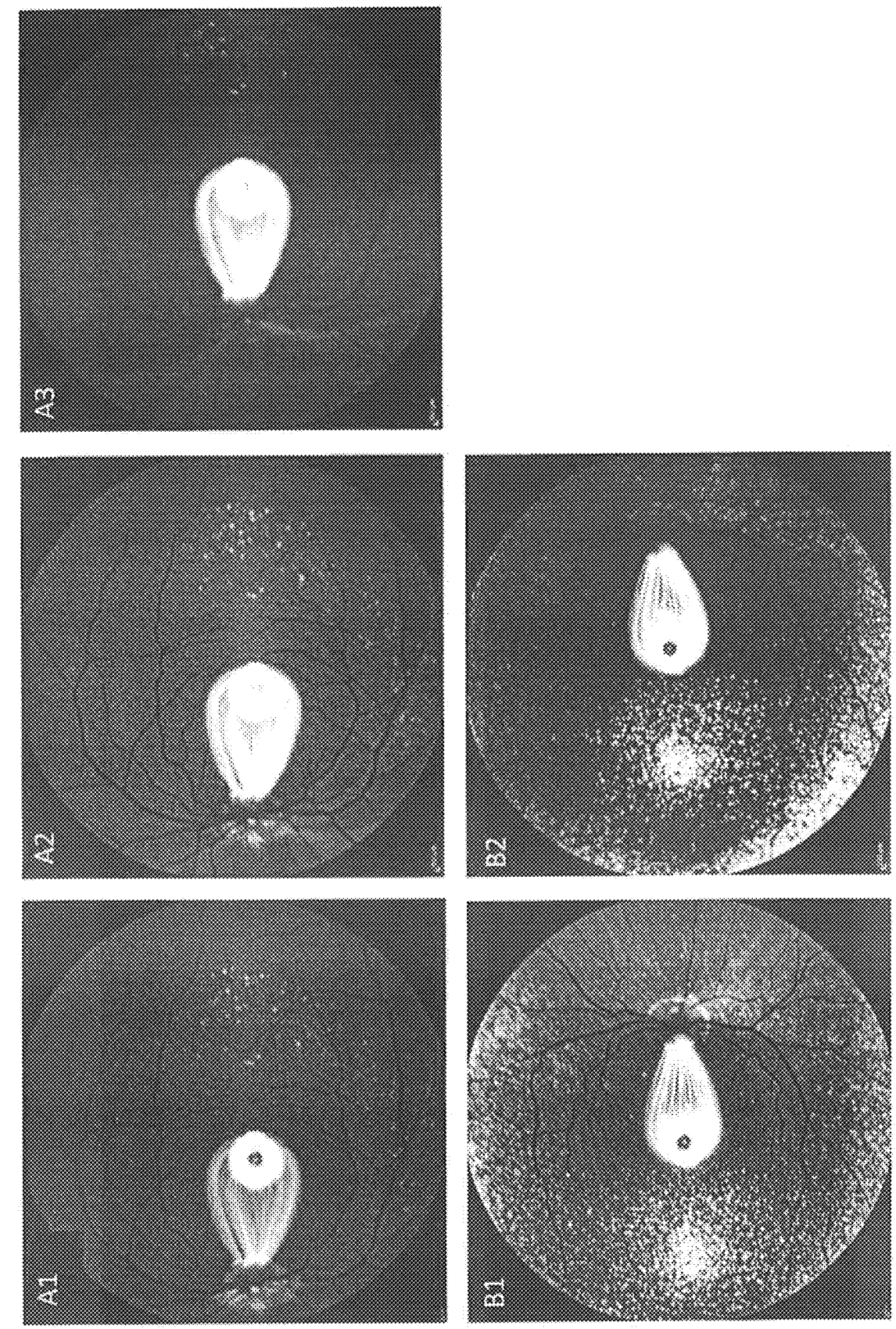
FIG. 9 provides fundus fluorescence images taken with a Heidelberg Spectralis™ of the retinas of Cynomolgus monkeys following intravitreal administration of the novel AAV variant LAISDQTKHA+P34A delivering a GFP transgene under the control of the CAG promoter (LAISDQTKHA+P34A.CAG.EGFP). (A) The retina of a monkey injected intravitreally with $2\times10^{11}$ vg of vector, imaged 14 days (A1), 21 days (A2), and 28 days (A3) after injection. (B) The retina of a monkey injected intravitreally with $1\times10^{12}$ vg of vector, imaged 14 days (B1) and 21 days (B2) after injection.
Figure 10A:
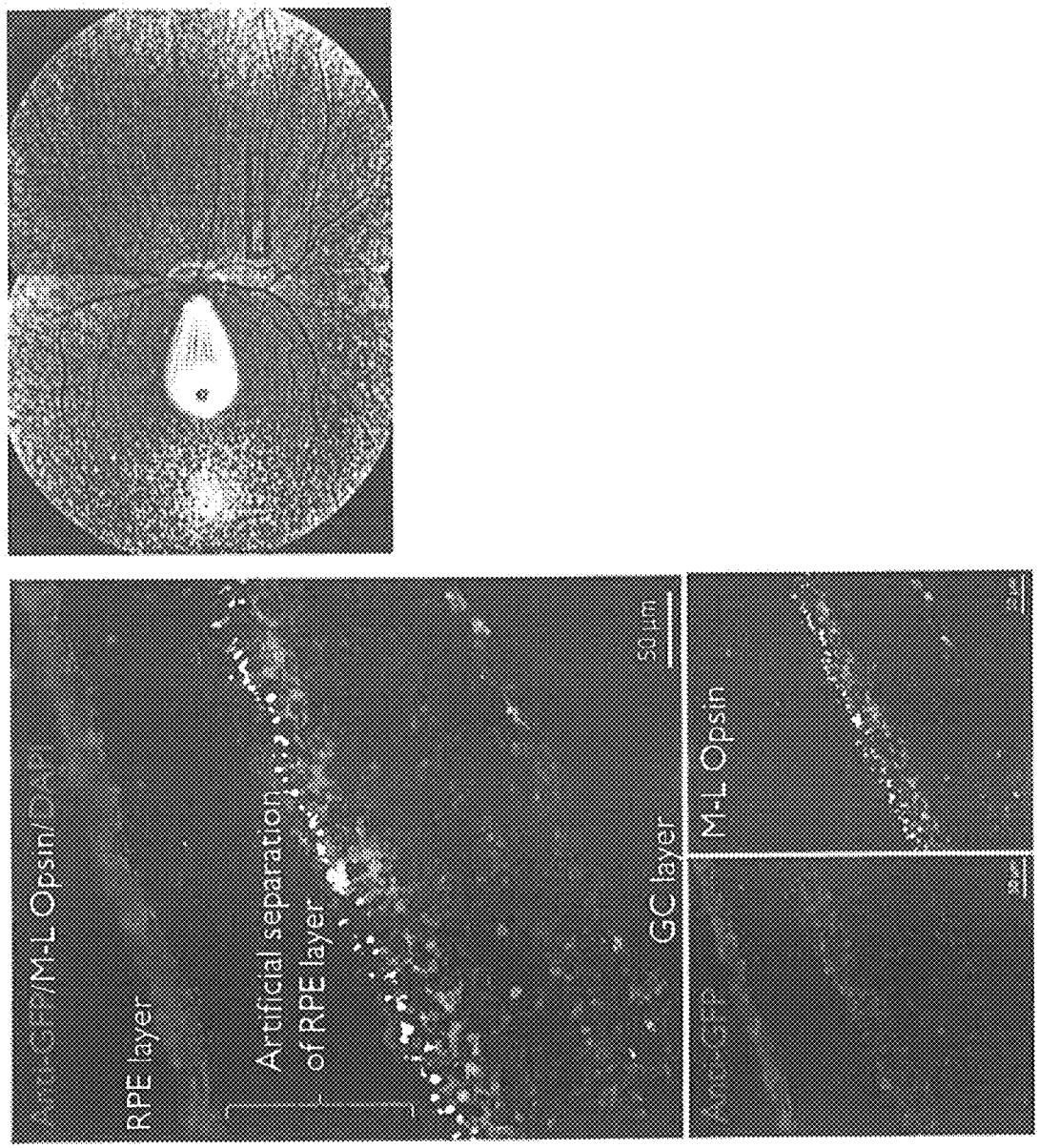
Figure 10D:
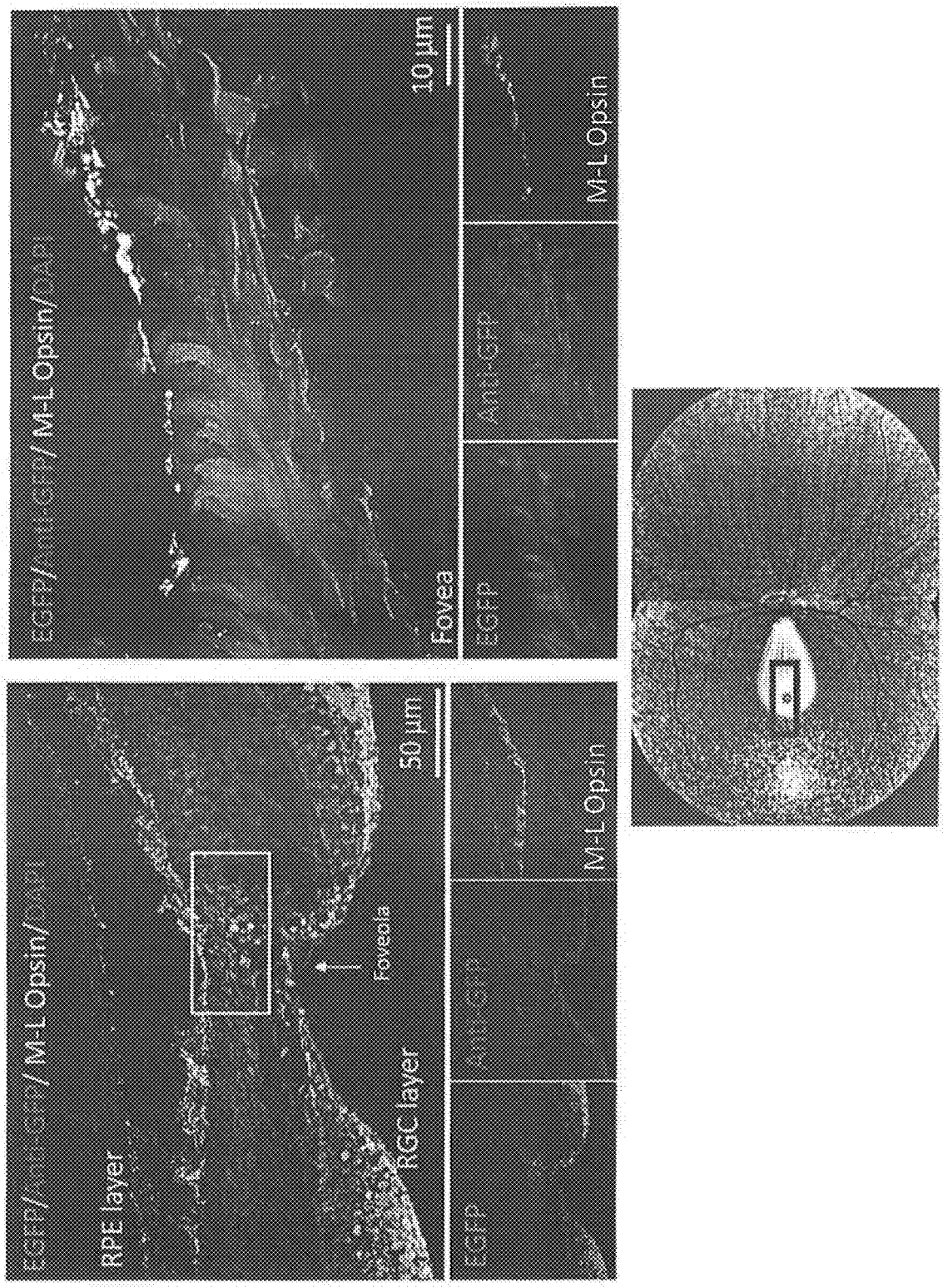
Figure 10E:
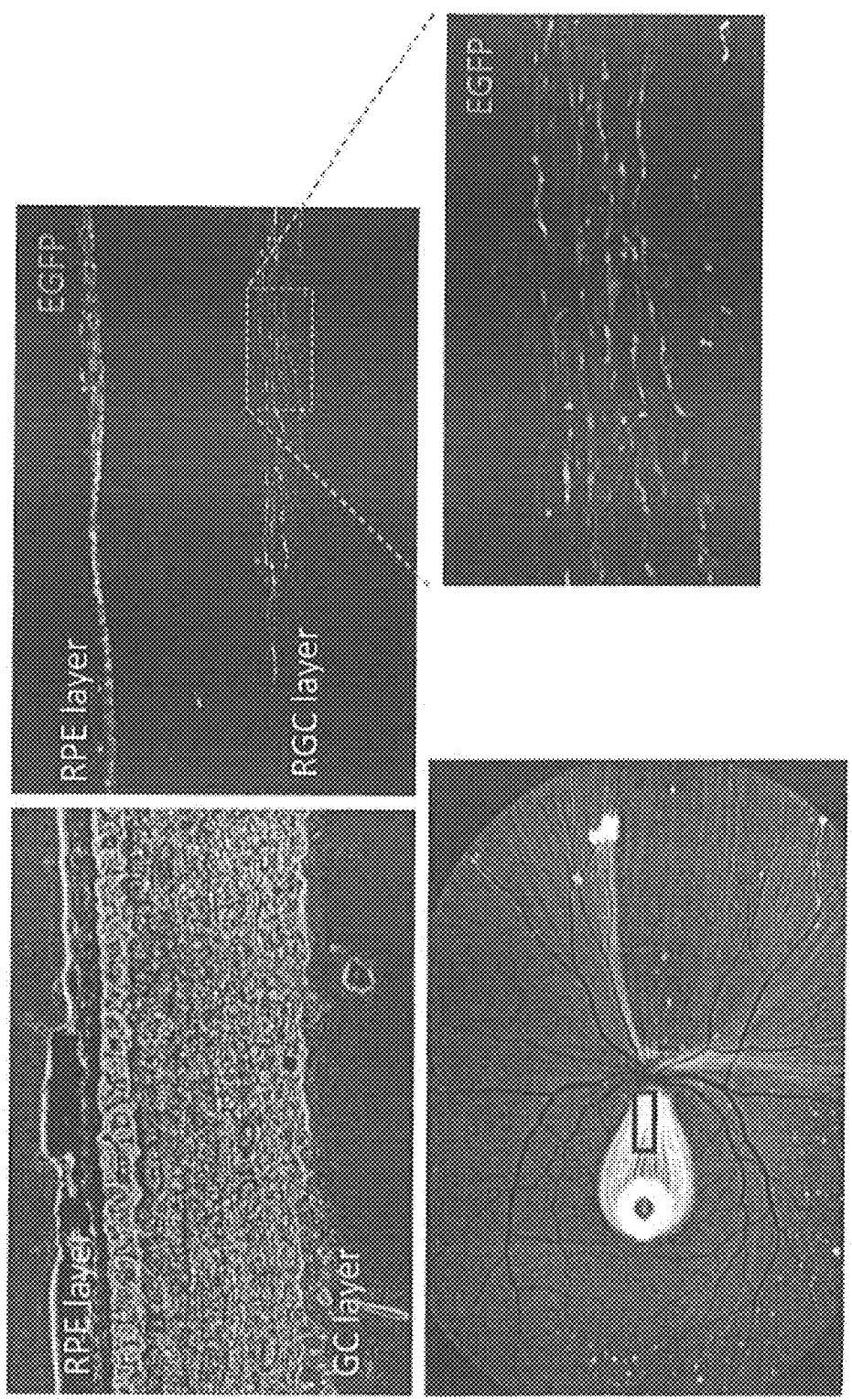

Intravitreal delivery of AAVs comprising the novel variant LAISDQTKHA+P34A resulted in broader and more robust transgenic expression across the NHP retina than AAV2 (FIGS. 7-9). Images reveal that the novel AAV variant capsid provides for robust expression within the center of the fovea (an area rich in cones); in the parafoveal ring (an area rich in retinal ganglion cells), and in the periphery (an area rich in many types of cells including rods, Muller glia, amacrine cells, bipolar cells) as early as 2 weeks after injection. In contrast, and consistent with results reported by others, wild type AAV2 provides for weaker expression that is primarily in the parafoveal ring and can only be detected at later time points. Immunohistochemical analysis of various regions of the retina performed 3 weeks after injection confirmed that many types of retinal cells, including retinal pigment epithelial cells, rod and cone photoreceptors, and retinal ganglion cells, had been successfully transduced throughout the retina (FIGS. 10A-10E).

This study in illustrates superior gene delivery by the ISDQTKH-comprising variant following a clinically preferred route of administration as compared to the clinically relevant AAV2. Similar efficacy is achievable with other variants comprising this peptide insertion motif. Likewise, similar efficacy is achievable with other variants disclosed herein that were identified using the same directed evolution approach.

Example 3

The cell tropism of the novel AAV variant LAISDQTKHA+P34A for retinal pigment epithelial (RPE) cells and photoreceptor (PR) cells was assessed in vitro in use RPE cells and PR cells generated from fibroblast-derived human induced pluripotent stem cells (FB-iPSC) or human embryonic stem cells (ESC).

AAV virions comprising either an AAV2 capsid or the novel variant capsid LAISDQTKHA+P34A and a genome comprising a green fluorescent protein (EGFP) transgene operably linked to a CAG promoter (AAV2.CAG.EGFP and LAISDQTKHA+P34A.CAG.EGFP, respectively) were manufactured using standard methods. Human RPE cell cultures were generated from the human embryonic stem cell line ESI-017 or human fibroblast-derived induced pluripotent stem cells ("FB-iPSC") using a 45-day differentiation protocol. Maturation into RPE cells was confirmed by detecting the expression of mature RPE markers including RPE65 and BEST1; the synthesis of VEGF and PEDF; and the ability to phagocytose rod outer segments. PR cultures were generated by a multi-step eye cup formation paradigm and confirmed to comprise PRs by detecting the expression of Recoverin and S Opsin after 179 days in culture.

Figure 11A:
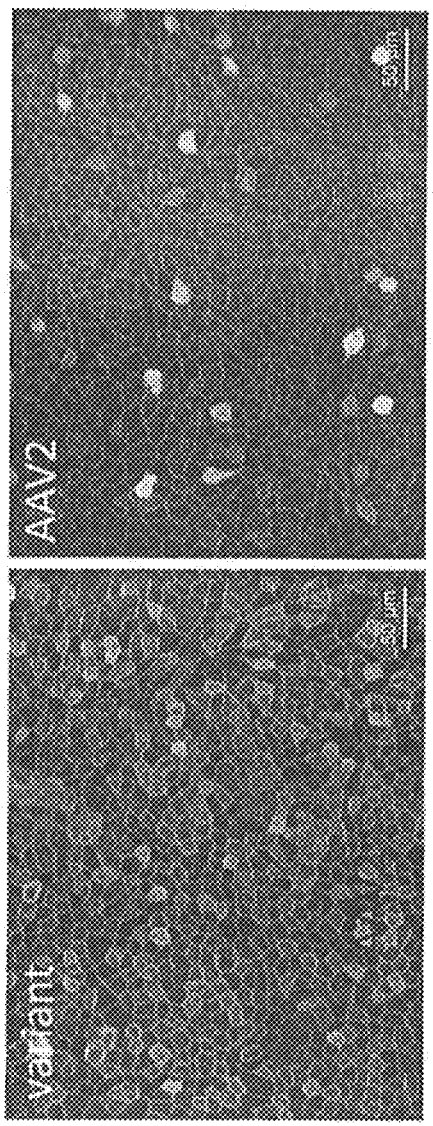
FIGS. 11A-11F provides data on the transduction of human retinal pigment epithelial (RPE) cells in vitro by recombinant AAV virus comprising the novel AAV variant LAISDQTKHA+P34A capsid and a GFP transgene under the control of the CAG promoter. Cells that were differentiated into RPE cells from a human embryonic stem cell line (FIGS. 11A and 11C) or from human fibroblast-derived induced pluripotent stem cells (FB-iPSC) (FIGS. 11B and 11D) were infected with novel AAV variant LAISDQTKHA+P34A.CAG.GFP or wild type control AAV2.CAG.GFP.
Figure 11B:
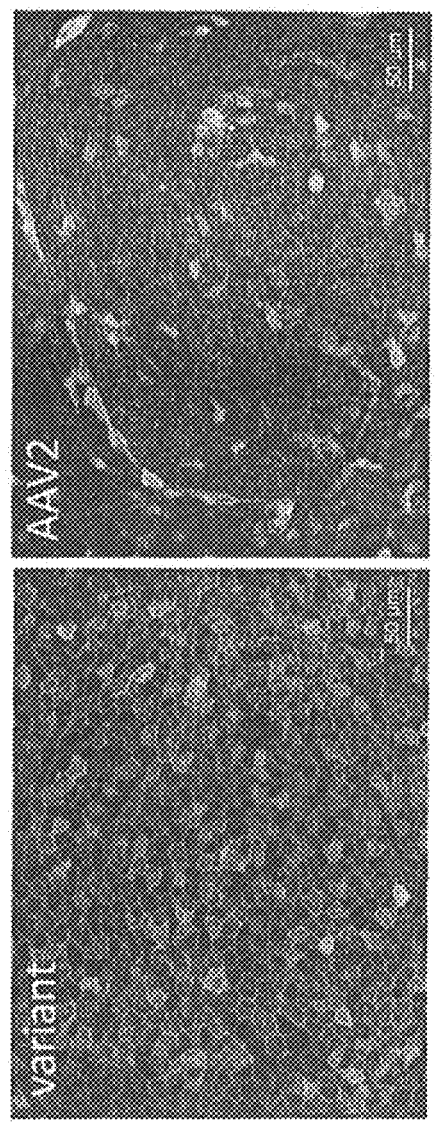
Figure 11C:
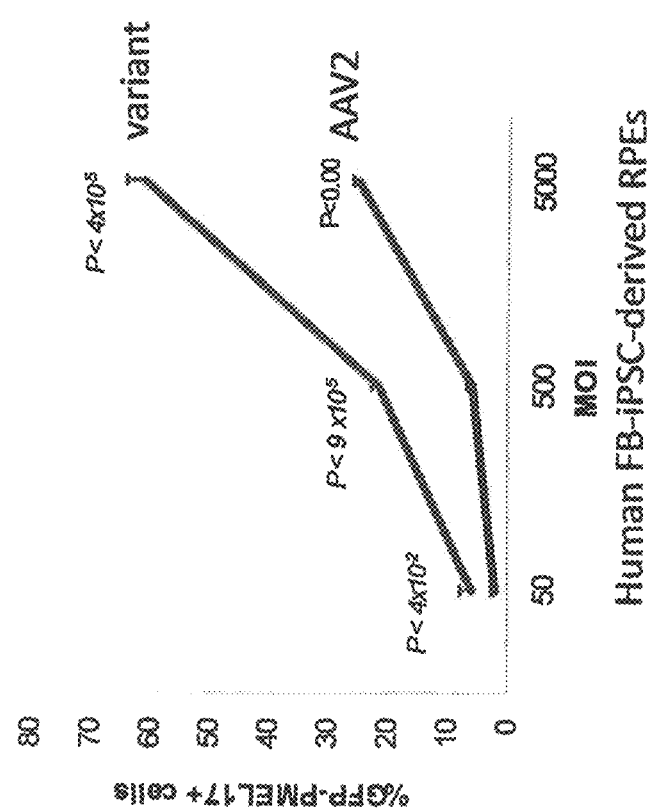
Figure 11D:
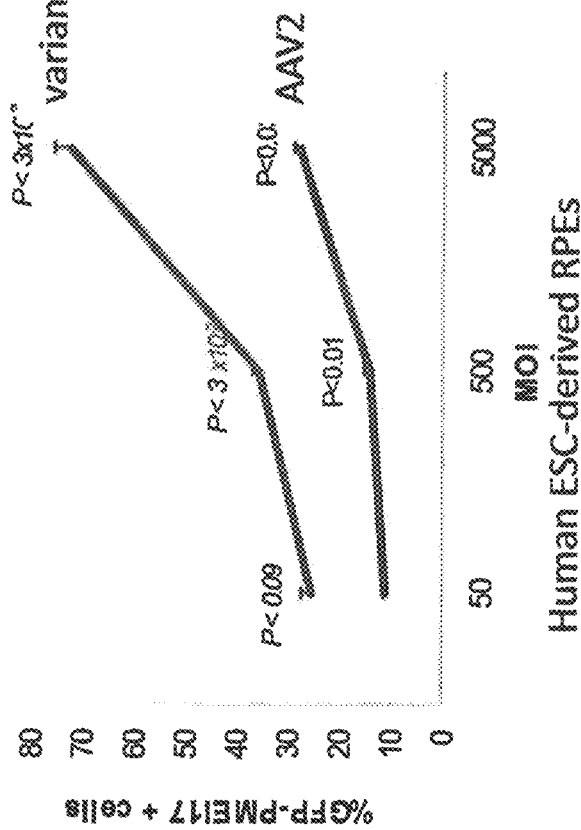
Figures 11E, 11F:
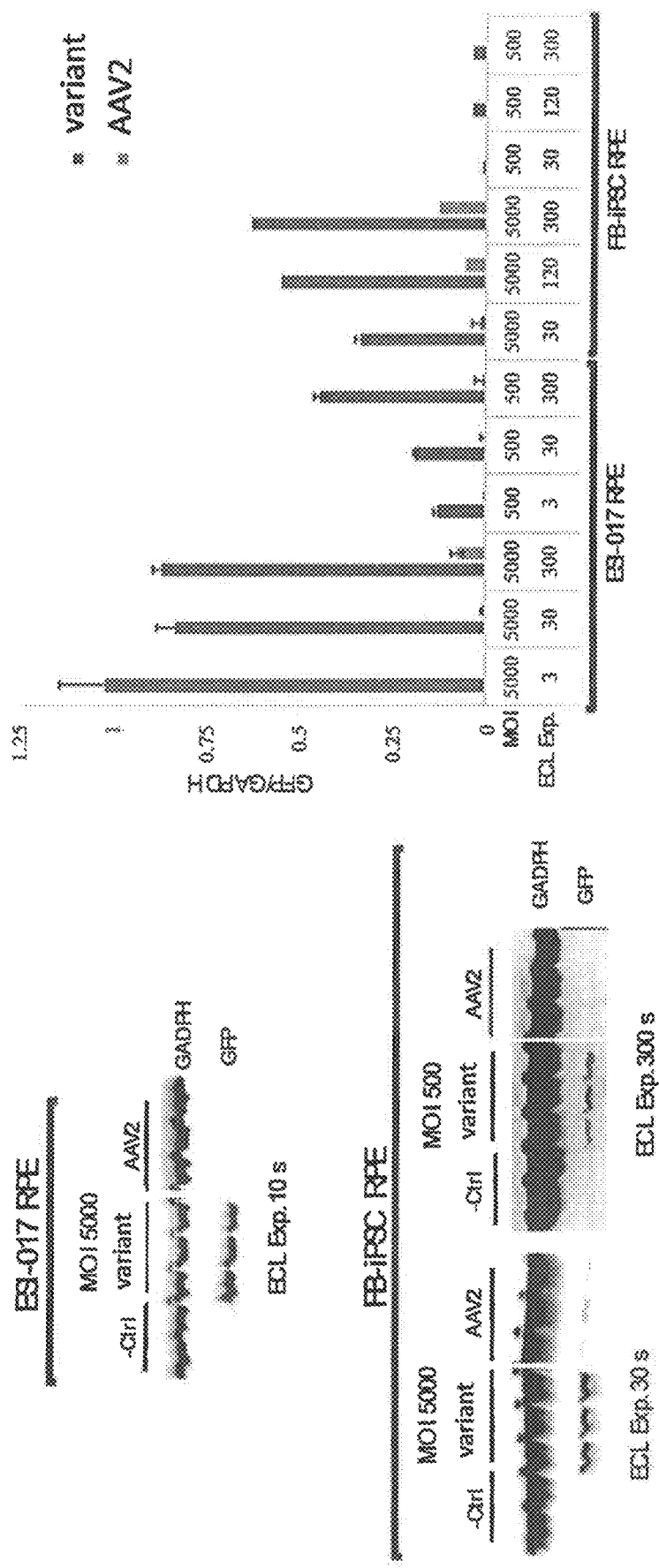

Relative to AAV2, LAISDQTKHA+P34A provided for significantly higher transduction efficiency of and transgene expression in human RPE cultures seven days post-infection as determined by immunofluorescence (FIGS. 11A-B), flow cytometry (2.7-fold increase; FIGS. 11C-D) and Western blot analysis (FIGS. 11E-F). Robust transduction and expression was likewise achieved using LAISDQTKHA+P34A.CAG.EGFP in human PR cultures by 32 days post-infection. This study illustrates the superior ability of ISDQTKH (SEQ ID NO:14)-comprising variants to deliver genes to retinal cells.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions.

Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

We claim:

1. A method for treating a human subject with X-linked retinitis pigmentosa, the method comprising
administering to the subject by intravitreal injection, a pharmaceutical composition comprising a therapeutically effective amount of an infectious recombinant adeno-associated virus (rAAV) virion comprising (i) a variant AAV capsid protein comprising the amino acid sequence set forth in SEQ ID NO:42 and (ii) a heterologous nucleic acid comprising a nucleotide sequence encoding a retinitis pigmentosa GTPase regulator protein, said nucleotide sequence operably linked to an ubiquitous promoter or a rhodopsin kinase promoter that directs expression of the retinitis pigmentosa GTPase regulator protein in one or more photoreceptor cells, thereby treating X-linked retinitis pigmentosa in said subject.

2. The method according to claim 1, wherein said nucleotide sequence is operably linked to a rhodopsin kinase promoter.

3. The method according to claim 1, comprising administering to the subject a pharmaceutical composition comprising from $10^{11}$ to $10^{15}$ vg of said rAAV and a pharmaceutically acceptable excipient.

4. A method for treating a human subject with X-linked retinitis pigmentosa, the method comprising
administering to the subject by subretinal injection, a pharmaceutical composition comprising a therapeutically effective amount of an infectious recombinant adeno-associated virus (rAAV) virion comprising (i) a variant AAV capsid protein comprising the amino acid sequence set forth in SEQ ID NO:42 and (ii) a heterologous nucleic acid comprising a nucleotide sequence encoding a retinitis pigmentosa GTPase regulator protein, said nucleotide sequence operably linked to an ubiquitous promoter or a rhodopsin kinase promoter that directs expression of the retinitis pigmentosa GTPase regulator protein in one or more photoreceptor cells, thereby treating X-linked retinitis pigmentosa in said subject.

5. The method according to claim 4, wherein said nucleotide sequence is operably linked to a rhodopsin kinase promoter.

6. The method according to claim 4, comprising administering to the subject a pharmaceutical composition comprising from $10^{11}$ to $10^{15}$ vg of said rAAV and a pharmaceutically acceptable excipient.

* * * * *